US012715981B2

(12) United States Patent
Kim et al.

(10) Patent No.: US 12,715,981 B2
(45) Date of Patent: Aug. 25, 2026

(54) COMPOSITIONS COMPRISING INSOLUBLE ALPHA-GLUCAN

(71) Applicant: Nutrition & Biosciences USA 4, Inc., Rochester, NY (US)

(72) Inventors: Kyle Hyun Chang Kim, Wilmington, DE (US); Natnael Behabtu, Oegstgeest (NL); Simon Eustace, Lincoln University, PA (US); John E. Crosier, Bear, DE (US); Frank Messick, Newark, DE (US)

(73) Assignee: NUTRITION & BIOSCIENCES USA 4, INC., Wilmington, DE (US)

( * ) Notice: Subject to any disclaimer, the term of this patent is extended or adjusted under 35 U.S.C. 154(b) by 359 days.

(21) Appl. No.: 18/557,617

(22) PCT Filed: May 3, 2022

(86) PCT No.: PCT/US2022/027452
§ 371 (c)(1),
(2) Date: Oct. 27, 2023

(87) PCT Pub. No.: WO2022/235655
PCT Pub. Date: Nov. 10, 2022

(65) Prior Publication Data
US 2024/0294737 A1 Sep. 5, 2024

Related U.S. Application Data

(60) Provisional application No. 63/183,825, filed on May 4, 2021.

(51) Int. Cl.

| | |
|---|---|
| ***C08L 5/00*** | (2006.01) |
| ***A61K 8/73*** | (2006.01) |
| ***A61Q 19/00*** | (2006.01) |
| ***C08J 3/00*** | (2006.01) |
| ***C08J 3/20*** | (2006.01) |
| ***C08K 3/20*** | (2006.01) |

(52) U.S. Cl.
CPC *C08L 5/00* (2013.01); *A61K 8/73* (2013.01); *A61Q 19/00* (2013.01); *C08J 3/005* (2013.01); *C08J 3/203* (2013.01); *A61K 2800/10* (2013.01); *A61K 2800/48* (2013.01); *C08J 2305/00* (2013.01); *C08J 2405/00* (2013.01)

(58) Field of Classification Search
None
See application file for complete search history.

(56) References Cited

U.S. PATENT DOCUMENTS

| | | | |
|---|---|---|---|
| 7,000,000 | B1 | 2/2006 | O'Brien |
| 7,022,352 | B2 | 4/2006 | Castro et al. |
| 8,871,474 | B2 | 10/2014 | Payne et al. |
| 10,301,604 | B2 | 5/2019 | Li et al. |
| 2009/0093543 | A1 | 4/2009 | Xue et al. |
| 2013/0244287 | A1 | 9/2013 | O'Brien et al. |
| 2014/0187767 | A1 | 7/2014 | Kasat et al. |
| 2015/0064748 | A1 | 3/2015 | Caimi et al. |
| 2015/0152196 | A1 | 6/2015 | Phanopoulos et al. |
| 2015/0191550 | A1 | 7/2015 | Mishra et al. |
| 2015/0232819 | A1 | 8/2015 | Paullin et al. |
| 2015/0239995 | A1 | 8/2015 | Landschutze et al. |
| 2015/0259439 | A1 | 9/2015 | Nambiar et al. |
| 2016/0122445 | A1 | 5/2016 | Nambiar et al. |
| 2016/0304629 | A1 * | 10/2016 | Kasat ........................ C08L 5/00 |
| 2016/0311935 | A1 | 10/2016 | Dennes et al. |
| 2016/0347978 | A1 | 12/2016 | Thompson et al. |
| 2017/0002335 | A1 | 1/2017 | Payne et al. |
| 2017/0362345 | A1 | 12/2017 | Behabtu et al. |
| 2018/0021238 | A1 | 1/2018 | Huh et al. |
| 2018/0022834 | A1 | 1/2018 | Paullin et al. |
| 2018/0079832 | A1 | 3/2018 | Paullin et al. |
| 2018/0155455 | A1 | 6/2018 | Paullin et al. |
| 2018/0230241 | A1 | 8/2018 | Johnson et al. |
| 2018/0237816 | A1 | 8/2018 | Paullin et al. |
| 2018/0258590 | A1 | 9/2018 | Behabtu et al. |
| 2018/0273731 | A1 | 9/2018 | Opietnik et al. |
| 2018/0340199 | A1 * | 11/2018 | Nagy ...................... C12P 19/04 |
| 2019/0078062 | A1 | 3/2019 | Li et al. |
| 2019/0078063 | A1 | 3/2019 | Li et al. |
| 2019/0112456 | A1 | 4/2019 | Bell et al. |
| 2019/0144897 | A1 | 5/2019 | Zhu et al. |
| 2019/0153674 | A1 | 5/2019 | Behabtu |
| 2019/0185893 | A1 | 6/2019 | Guan et al. |

(Continued)

FOREIGN PATENT DOCUMENTS

| | | |
|---|---|---|
| WO | 2016196022 A1 | 12/2016 |
| WO | 2018081263 A1 | 5/2018 |

(Continued)

OTHER PUBLICATIONS

Simpson et al., Microbiology 141:1451-1460, 1995.
International Preliminary Report on Patentability for PCT/US2022/027452 issued Oct. 24, 2023.

*Primary Examiner* — Dominic Lazaro

(57) ABSTRACT

Disclosed herein are compositions comprising (i) an insoluble alpha-glucan and soluble alpha-glucan derivative, or (ii) an insoluble alpha-glucan and additive. These compositions can be in the form of particles, for example, such as particles comprising insoluble alpha-glucan coated with a soluble alpha-glucan derivative and/or additive. Methods are further disclosed for preparing these compositions, as well as various applications of using them.

20 Claims, No Drawings

(56) References Cited

U.S. PATENT DOCUMENTS

| | | | |
|---|---|---|---|
| 2019/0225737 | A1 | 7/2019 | Behabtu et al. |
| 2020/0002646 | A1 | 1/2020 | Huang et al. |
| 2020/0131281 | A1 | 4/2020 | Guan et al. |
| 2020/0165360 | A1 | 5/2020 | Behabtu et al. |
| 2020/0263026 | A1 | 8/2020 | Lenges et al. |
| 2020/0308371 | A1 | 10/2020 | Briegel et al. |

FOREIGN PATENT DOCUMENTS

| | | | |
|---|---|---|---|
| WO | 2018200437 | A1 | 11/2018 |
| WO | 2019246228 | A1 | 12/2019 |
| WO | 2021247810 | A1 | 12/2021 |
| WO | 2021252569 | A1 | 12/2021 |
| WO | 2021252575 | A1 | 12/2021 |
| WO | 2021257786 | A1 | 12/2021 |

* cited by examiner

COMPOSITIONS COMPRISING INSOLUBLE ALPHA-GLUCAN

This application claims the benefit of U.S. Provisional Appl. No. 63/183,825 (filed May 4, 2021), which is incorporated herein by reference in its entirety.

FIELD

The present disclosure is in the field of polysaccharides. For example, the disclosure pertains to compositions comprising insoluble alpha-glucan and at least one additive, and use of this material in various applications.

BACKGROUND

Driven by a desire to use polysaccharides in various applications, researchers have explored for polysaccharides that are biodegradable and that can be made economically from renewably sourced feedstocks. One such polysaccharide is alpha-1,3-glucan, an insoluble glucan polymer characterized by having alpha-1,3-glycosidic linkages. This polymer has been prepared, for example, using a glucosyltransferase enzyme isolated from *Streptococcus salivarius* (Simpson et al., Microbiology 141:1451-1460, 1995). Also for example, U.S. Pat. No. 7,000,000 disclosed the preparation of a spun fiber from enzymatically produced alpha-1,3-glucan. Various other glucan materials have also been studied for developing new or enhanced applications. For example, U.S. Patent Appl. Publ. No. 2015/0232819 discloses enzymatic synthesis of several insoluble glucans having mixed alpha-1,3 and -1,6 linkages.

New forms of insoluble alpha-glucan are desired to enhance the economic value and performance characteristics of this material in various applications. Addressing this need, described herein are compositions comprising insoluble alpha-glucan and one or more additives.

SUMMARY

In one embodiment, the present disclosure concerns a composition comprising insoluble alpha-glucan and a soluble alpha-glucan derivative, wherein at least about 50% of the glycosidic linkages of the insoluble alpha-glucan are alpha-1,3 glycosidic linkages, and the weight-average degree of polymerization (DPw) of the insoluble alpha-glucan is at least 15, wherein at least about 50% of the glycosidic linkages of the soluble alpha-glucan derivative are alpha-1,3 glycosidic linkages, and the DPw of the alpha-glucan portion of the soluble alpha-glucan derivative is at least 15.

In another embodiment, the present disclosure concerns a method of producing the foregoing composition, the method comprising: (a) blending together at least water, the insoluble alpha-glucan, and the soluble alpha-glucan derivative to provide a blended product, and (b) optionally drying the blended product.

In another embodiment, the present disclosure concerns a method of producing a composition comprising at least insoluble alpha-glucan and an additive, the method comprising: (a) blending (i) an additive and (ii) a composition comprising about 10 to 80 wt % of insoluble alpha-glucan and a balance of water or aqueous solution up to 100 wt %, thereby providing a blended product, optionally wherein the mass of the additive is within about 25% of the mass of the water or aqueous solution, and the additive does not chemically react with insoluble alpha-glucan, and wherein at least about 50% of the glycosidic linkages of the insoluble alpha-glucan are alpha-1,3 glycosidic linkages, and the weight-average degree of polymerization (DPw) of the insoluble alpha-glucan is at least 15, and (b) drying the blended product, wherein most of (e.g., ≥90 wt %), or all of, the water that was present in the composition of (ii) is replaced with the additive. A composition produced by this method is another embodiment herein.

In another embodiment, the present disclosure concerns a composition comprising insoluble alpha-glucan that is coated by at least one additive, wherein the additive does not chemically react with the insoluble alpha-glucan, wherein at least about 50% of the glycosidic linkages of the insoluble alpha-glucan are alpha-1,3 glycosidic linkages, and the weight-average degree of polymerization (DPw) of the insoluble alpha-glucan is at least 15.

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" (i.e., 1-5) is recited, the recited range should be construed as including ranges "1 to 4", "1 to 3", "1-2", "1-2 & 4-5", "1-3 & 5", and the like. The numerical values of the various ranges in the present disclosure, unless expressly indicated otherwise, are stated as approximations as though the minimum and maximum values within the stated ranges were both proceeded by the word "about". In this manner, slight variations above and below the stated ranges can typically be used to achieve substantially the same results as values within the ranges. Also, the disclosure of these ranges is intended as a continuous range including each and every value between the minimum and maximum values.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

It is to be appreciated that certain features of the present disclosure, which are, for clarity, described above and below in the context of aspects/embodiments, may also be provided in combination in a single element. Conversely, various features of the disclosure that are, for brevity, described in the context of a single aspect/embodiment, can also be provided separately or in any sub-combination.

The term "polysaccharide" (or "glycan") means a polymeric carbohydrate molecule composed of long chains of monosaccharide units bound together by glycosidic linkages and on hydrolysis gives the polysaccharide's constituent monosaccharides and/or oligosaccharides. A polysaccharide herein can be linear or branched, and/or can be a homopolysaccharide (comprised of only one type of constituent monosaccharide) or heteropolysaccharide (comprised of two or more different constituent monosaccharides). Examples of polysaccharides herein include glucan (polyglucose), fructan (polyfructose), galactan (polygalactose), mannan (polymannose), arabinan (polyarabinose), xylan (polyxylose), and soy polysaccharide.

The term "saccharide" and other like terms herein refer to monosaccharides and/or disaccharides/oligosaccharides, unless otherwise noted. A "disaccharide" herein refers to a carbohydrate having two monosaccharides joined by a glycosidic linkage. An "oligosaccharide" herein can refer to a carbohydrate having 3 to 15 monosaccharides, for example, joined by glycosidic linkages. An oligosaccharide can also be referred to as an "oligomer". Monosaccharides (e.g., glucose and/or fructose) comprised within disaccharides/oligosaccharides can be referred to as "monomeric units", "monosaccharide units", or other like terms.

A "glucan" herein is a type of polysaccharide that is a polymer of glucose (polyglucose). A glucan can be comprised of, for example, about, or at least about, 90%, 91%, 92%, 93%, 94%, 95%, 96%, 97%, 98%, 99%, or 100% by weight glucose monomeric units. Examples of glucans herein include alpha-glucans.

The terms "alpha-glucan", "alpha-glucan polymer" and the like are used interchangeably herein. An alpha-glucan is a polymer comprising glucose monomeric units linked together by alpha-glycosidic linkages. In typical aspects, the glycosidic linkages of an alpha-glucan herein are about, or at least about, 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages. Examples of an alpha-glucan polymer herein include alpha-1,3-glucan.

The terms "alpha-1,3-glucan", "poly alpha-1,3-glucan", "alpha-1,3-glucan polymer" and the like are used interchangeably herein. Alpha-1,3-glucan is an alpha-glucan comprising glucose monomeric units linked together by glycosidic linkages, wherein at least about 50% of the glycosidic linkages are alpha-1,3. Alpha-1,3-glucan in some aspects comprises about, or at least about, 90%, 95%, or 100% alpha-1,3 glycosidic linkages. Most or all of the other linkages, if present, in alpha-1,3-glucan herein typically are alpha-1,6, though some linkages may also be alpha-1,2 and/or alpha-1,4. Alpha-1,3-glucan herein is typically water-insoluble.

The terms "dextran", "dextran polymer", "dextran molecule", "alpha-1,6-glucan" and the like in some aspects herein refer to a water-soluble alpha-glucan comprising at least 50%, 60%, 70%, 80%, 90%, 95%, 96%, 97%, 98%, 99%, or 99.5% alpha-1,6 glycosidic linkages (with the balance of the linkages typically being all or mostly alpha-1,3).

The term "copolymer" herein refers to a polymer comprising at least two different types of alpha-glucan, such as dextran and alpha-1,3-glucan. The terms "graft copolymer", "branched copolymer" and the like herein generally refer to a copolymer comprising a "backbone" (or "main chain") and side chains branching from the backbone. The side chains are structurally distinct from the backbone. Examples of graft copolymers herein comprise a dextran backbone (or dextran backbone that has been modified with about 1%-35% alpha-1,2 and/or alpha-1,3 branches, e.g.), and at least one side chain of alpha-1,3-glucan comprising at least about 50% alpha-1,3 glycosidic linkages. An alpha-1,3-glucan side chain herein can have a linkage and molecular weight of alpha-1,3-glucan as disclosed herein, for example. In some aspects, a dextran backbone can have an alpha-1,3-glucan extension, since the non-reducing end(s) of dextran can prime alpha-1,3-glucan synthesis by a glucosyltransferase enzyme.

The terms "linkage", "glycosidic linkage", "glycosidic bond" and the like refer to the covalent bonds connecting the sugar monomers within a saccharide compound (oligosaccharides and/or polysaccharides). Examples of glycosidic linkages include 1,6-alpha-D-glycosidic linkages (herein also referred to as "alpha-1,6" linkages) and 1,3-alpha-D-glycosidic linkages (herein also referred to as "alpha-1,3" linkages).

The glycosidic linkage profile of a polysaccharide or derivative thereof can be determined using any method known in the art. For example, a linkage profile can be determined using methods using nuclear magnetic resonance (NMR) spectroscopy (e.g., $^{13}C$ NMR and/or $^{1}H$ NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, F L, 2005), which is incorporated herein by reference.

An "alpha-1,2 branch" (and like terms) as referred to herein typically comprises a glucose that is alpha-1,2-linked to a dextran backbone; thus, an alpha-1,2 branch herein can also be referred to as an alpha-1,2,6 linkage. An alpha-1,2 branch herein typically has one glucose group (can optionally be referred to as a pendant glucose).

An "alpha-1,3 branch" (and like terms) as referred to herein typically comprises a glucose that is alpha-1,3-linked to a dextran backbone; thus, an alpha-1,3 branch herein can also be referred to as an alpha-1,3,6 linkage. An alpha-1,3 branch herein typically has one glucose group (can optionally be referred to as a pendant glucose).

The percent branching in a polysaccharide herein refers to that percentage of all the linkages in the polysaccharide that represent branch points. For example, the percent of alpha-1,3 branching in an alpha-glucan herein refers to that percentage of all the linkages in the glucan that represent alpha-1,3 branch points. Except as otherwise noted, linkage percentages disclosed herein are based on the total linkages of a polysaccharide, or the portion of a polysaccharide for which a disclosure specifically regards.

The "molecular weight" of a polysaccharide or polysaccharide derivative herein can be represented as weight-average molecular weight (Mw) or number-average molecular weight (Mn), the units of which are in Daltons (Da) or grams/mole. Alternatively, molecular weight can be represented as DPw (weight average degree of polymerization) or DPn (number average degree of polymerization). The molecular weight of smaller polysaccharide polymers such as oligosaccharides can optionally be provided as "DP" (degree of polymerization), which simply refers to the number of monomers comprised within the polysaccharide; "DP" can also characterize the molecular weight of a polymer on an individual molecule basis. Various means are known in the art for calculating these various molecular weight measurements such as with high-pressure liquid chromatography (HPLC), size exclusion chromatography (SEC), or gel permeation chromatography (GPC).

As used herein, Mw can be calculated as $Mw=\Sigma NiMi^2/\Sigma NiMi$; where Mi is the molecular weight of an individual chain i and Ni is the number of chains of that molecular weight. Besides SEC, the Mw of a polymer can be determined by other techniques such as static light scattering, mass spectrometry, MALDI-TOF (matrix-assisted laser desorption/ionization time-of-flight), small angle X-ray or neutron scattering, or ultracentrifugation. As used herein, Mn can be calculated as $Mn=\Sigma NiMi/\Sigma Ni$ where Mi is the molecular weight of a chain i and Ni is the number of chains of that molecular weight. Besides SEC, the Mn of a polymer can be determined by various colligative property methods such as vapor pressure osmometry, end-group determination by spectroscopic methods such as proton NMR, proton FTIR, or UV-Vis. As used herein, DPn and DPw can be calculated from Mw and Mn, respectively, by dividing them by molar mass of the one monomer unit Mi. In the case of unsubstituted glucan polymer, $M_1=162$. In the case of a substituted (derivatized) glucan polymer, $M_1=162+M_f\times$ DoS, where $M_f$ is molar mass of the substituting group, and DoS is degree of substitution (average number of substituted groups per one glucose unit of the glucan polymer).

The terms "crystalline", "crystalline solid", "crystal" and like terms herein refer to a solid material whose constituents are arranged in a regularly ordered structure forming a lattice; such material typically is a portion of a larger composition having both crystalline and amorphous regions. An "amorphous" material is non-crystalline in that its constituents are not organized in a definite lattice pattern, but rather are randomly organized. Crystalline materials, but not amorphous materials, usually have a characteristic geometric shape (e.g., plate). The terms "crystallinity", "crystallinity index" (CI), "degree of crystallinity" and the like herein refer to the fractional amount (mass fraction or volume fraction) of an insoluble alpha-glucan that is crystalline, and can be referred to in decimal or percentage form (e.g., a crystallinity of 0.65 corresponds to a crystallinity of 65%). This fractional amount is of a total amount or volume that includes the amorphous content of the insoluble alpha-glucan. Crystallinity herein can be as measured using techniques such as differential scanning calorimetry (DSC), X-ray diffraction (XRD), small angle X-ray scattering (SAXS), infrared spectroscopy, and/or density measurements according to, for example, Struszczyk et al. (1987, *J. Appl. Polym. Sci.* 33:177-189), U.S. Patent Appl. Publ. Nos. 2015/0247176, 2010/0233773, or 2015/0152196, or International Patent Appl. Publ. No. WO2018/081263, which are all incorporated herein by reference. In some aspects, the crystallinity of insoluble alpha-1,3-glucan herein can be as determined according to the methodology disclosed in the below Examples (Materials/Methods).

The terms "particle", "particulate" and like terms are interchangeably used herein, and refers to the smallest identifiable unit in a particulate system. The term "particulated" and like terms can be used to characterize particles of insoluble alpha-glucan herein; particulated insoluble alpha-glucan in typical aspects of the present disclosure is as this material exists when dispersed under aqueous conditions. Particle size in some aspects can refer to particle diameter and/or the length of the longest particle dimension. The average size can be based on the average of diameters and/or longest particle dimensions of at least 50, 100, 500, 1000, 2500, 5000, or 10000 or more particles, for example. Particles herein can be in plate form, for instance. Particle size herein can be measured by a process comprising light scattering or electrical impedance change (e.g., using a Coulter Counter), for example, such as described in any of U.S. Pat. Nos. 6,091,492, 6,741,350, or 9297737 (each incorporated herein by reference). Particle size and/or distributions can be as measured for particles comprised in an aqueous dispersion, for example. Particle size herein can optionally be expressed by a "$D_{10}$", "$D_{50}$", "$D_{90}$", etc. value; for example, a $D_{50}$ value is the diameter for which 50% by weight of the particles in a composition (e.g., dispersion) have a diameter under that diameter, and 50% by weight of the particles have a diameter greater than that diameter.

A "cake" of insoluble alpha-glucan herein refers to a preparation in condensed, compacted, packed, squeezed, and/or compressed form that comprises at least (i) about 50%-90% by weight water or an aqueous solution, and (ii) about 10%-50% by weight insoluble alpha-glucan. In some aspects, a cake of insoluble alpha-glucan herein can comprise at least (i) about 20%-90% by weight water or an aqueous solution, and (ii) about 10%-80% by weight insoluble alpha-glucan. A cake in some aspects can be referred to as a "filter cake" or a "wet cake". A cake herein typically has a soft, solid-like consistency.

The term "fibrids", "alpha-1,3-glucan fibrids", "fibrillated glucan" and the like as used herein can refer to nongranular, fibrous, or film-like particles with at least one of their three dimensions being of minor magnitude relative to the largest dimension. In some aspects, an alpha-1,3-glucan fibrid can have a fiber-like and/or a sheet-like structure with a relatively large surface area when compared to an alpha-1,3-glucan fiber. The surface area of fibrids herein can be about 5 to 50 $meter^2$/gram of material, with the largest dimension of about 10 to 1000 microns and the smallest dimension of 0.05 to 0.25 microns (aspect ratio of largest to smallest dimension of 40 to 20000.

A composition herein comprising insoluble alpha-glucan that is "dry" or "dried" typically has less than 12, 11, 10, 9, 8, 7, 6, 5, 4, 3, 2, 1, 0.5, or 0.1 wt % water comprised therein.

The terms "aqueous liquid", "aqueous fluid", "aqueous conditions", "aqueous reaction conditions", "aqueous setting", "aqueous system" and the like as used herein can refer to water or an aqueous solution. An "aqueous solution" herein can comprise one or more dissolved salts, where the maximal total salt concentration can be about 3.5 wt % in some aspects. Although aqueous liquids herein typically comprise water as the only solvent in the liquid, an aqueous liquid can optionally comprise one or more other solvents (e.g., polar organic solvent) that are miscible in water. Thus, an aqueous solution can comprise a solvent having at least about 10 wt % water.

An "aqueous composition" herein has a liquid component that comprises about, or at least about, 10, 20, 30, 40, 50, 60, 70, 80, 90, 95, 99, or 100 wt % water, for example. Examples of aqueous compositions include mixtures, solutions, dispersions (e.g., colloidal dispersions), suspensions and emulsions, for example.

As used herein, the term "colloidal dispersion" refers to a heterogeneous system having a dispersed phase and a dispersion medium, i.e., microscopically dispersed insoluble particles are suspended throughout another substance (e.g., an aqueous composition such as water or aqueous solution). An example of a colloidal dispersion herein is a hydrocolloid. All, or a portion of, the particles of a colloidal dispersion such as a hydrocolloid can comprise insoluble alpha-glucan as presently disclosed. The terms "dispersant" and "dispersion agent" are used interchangeably herein to refer to a material that promotes the formation and/or stabilization of a dispersion. "Dispersing" herein refers to the act of preparing a dispersion of a material in an aqueous liquid. As used herein, the term "latex" (and like terms) refers to a dispersion of one or more types of polymer particles in water or aqueous solution; typically, at least particles herein are in a latex composition as a dispersed polymer component. In some aspects, a latex is an emulsion that comprises a dispersion of at least particles herein. An "emulsion" herein is a dispersion of minute droplets of one liquid in another liquid in which the droplets are not soluble or miscible (e.g., a non-polar substance such as oil or other organic liquid such as an alkane, in a polar liquid such as water or aqueous solution). An emulsion can further comprise dispersed alpha-glucan herein, for example, which optionally can stabilize the emulsion. In some aspects, however, an emulsion herein can be a "dry emulsion". A dry emulsion is typically produced by removing all or most (e.g. >95%, >99%, or >99.5%) of the water of a liquid emulsion, such as by freeze-drying or spray-drying.

An alpha-glucan that is "insoluble", "aqueous-insoluble", "water-insoluble" (and like terms) (e.g., alpha-1,3-glucan with a DP of 8 or higher) herein does not dissolve (or does not appreciably dissolve) in water or other aqueous conditions, optionally where the aqueous conditions are further characterized to have a pH of 4-9 (e.g., pH 6-8) and/or temperature of about 1 to 130° C. (e.g., 20-25° C.). In some aspects, less than 1.0 gram (e.g., no detectable amount) of an aqueous-insoluble alpha-glucan herein dissolves in 1000 milliliters of such aqueous conditions (e.g., water at 23° C.). In contrast, glucans such as certain oligosaccharides herein that are "soluble", "aqueous-soluble", "water-soluble" and the like (e.g., alpha-1,3-glucan with a DP less than 8) appreciably dissolve under these conditions.

The term "viscosity" as used herein refers to the measure of the extent to which a fluid (aqueous or non-aqueous) resists a force tending to cause it to flow. Various units of viscosity that can be used herein include centipoise (cP, cps) and Pascal-second (Pa-s), for example. A centipoise is one one-hundredth of a poise; one poise is equal to 0.100 $kg \cdot m^{-1}s^{-1}$. Viscosity can be reported as "intrinsic viscosity" (IV, $\eta$, units of dL/g) in some aspects; this term refers to a measure of the contribution of a glucan polymer to the viscosity of a liquid (e.g., solution) comprising the glucan polymer. IV measurements herein can be obtained, for example, using any suitable method such as disclosed in U.S. Pat. Appl. Publ. Nos. 2017/0002335, 2017/0002336, or 2018/0340199, or Weaver et al. (*J. Appl. Polym. Sci.* 35:1631-1637) or Chun and Park (*Macromol. Chem. Phys.* 195:701-711), which are all incorporated herein by reference. IV can be measured, in part, by dissolving glucan polymer (optionally dissolved at about 100° C. for at least 2, 4, or 8 hours) in DMSO with about 0.9 to 2.5 wt % (e.g., 1, 2, 1-2 wt %) LiCl, for example. IV herein can optionally be used as a relative measure of molecular weight.

Particles of the present disclosure can provide stability to a dispersion or emulsion, for example. The "stability" (or the quality of being "stable") of a dispersion or emulsion herein is, for example, the ability of dispersed particles of a dispersion, or liquid droplets dispersed in another liquid (emulsion), to remain dispersed (e.g., about, or at least about, 70, 75, 80, 85, 90, 95, 96, 97, 98, 99, or 100 wt % of the particles of the dispersion or liquid droplets of the emulsion are in a dispersed state) for a period of about, or at least about, 2, 4, 6, 9, 12, 18, 24, 30, or 36 months following initial preparation of the dispersion or emulsion. A stable dispersion or emulsion can resist total creaming, sedimentation, flocculation, and/or coalescence of dispersed/emulsified material.

The term "zeta potential" as used herein refers to the electrical potential difference between a dispersion medium and the stationary layer of fluid attached to a particle dispersed in the dispersion medium. In general, a dispersed particle herein with a high zeta potential (negative or positive) is more electrically stabilized compared to a dispersed material with low zeta potentials (closer to zero). Since the repulsive forces of a high zeta potential material in a dispersion tend to exceed its attractive forces, such a dispersion is relatively more stable than a dispersion of low zeta potential material, which tends to more easily flocculate/coagulate. Zeta potential herein can be measured as disclosed, for example, in U.S. patent. Nos. 6109098 or 4602989, U.S. Patent Appl. Publ. No. 2020/0131281, or Int. Patent Appl. Publ. Nos. WO2014/097402 or EP0869357, which are incorporated herein by reference.

A "polysaccharide derivative" (and like terms) herein (e.g., a glucan derivative such as an alpha- or beta-glucan derivative) typically refers to a polysaccharide that has been substituted with at least one type of organic group. The degree of substitution (DoS) of a polysaccharide derivative herein can be up to about 3.0 (e.g., about 0.001 to about 3.0). An organic group can be linked to a polysaccharide derivative herein via an ether, ester, carbamate/carbamoyl, or sulfonyl linkage, for example. A precursor of a polysaccharide derivative herein refers to the non-derivatized polysaccharide used to make the derivative (can also be referred to as the polysaccharide portion of the derivative). An organic group herein typically is charged (anionic or cationic); generally, such charge can be as it exists when the organic group is in an aqueous composition herein, further taking into account the pH of the aqueous composition (in some aspects, the pH can be 4-10 or 5-9, or any pH as disclosed herein).

The term "degree of substitution" (DoS, or DS) as used herein refers to the average number of hydroxyl groups that are substituted with organic groups (e.g., via an ether, ester, or other linkage herein) in each monomeric unit of a polysaccharide derivative. The DoS of a polysaccharide derivative herein can be stated with reference to the DoS of a specific substituent, or the overall DoS, which is the sum of the DoS values of different substituent types (e.g., if a mixed ether or mixed ester). Unless otherwise disclosed, when DoS is not stated with reference to a specific substituent type, the overall DoS is meant.

Terms used herein regarding "ethers" (e.g., polysaccharide ether derivative) can be as disclosed, for example, in U.S. Patent Appl. Publ. Nos. 2014/179913, 2016/0304629, 2016/0311935, 2015/0239995, 2018/0230241, 201810237816, or 2020/0002646, U.S. Appl. No. 63/037,076, or Int. Pat. Appl. Publ. Nos. WO2021/252569, WO2021/257786, or WO2021/247810, which are each incorporated herein by reference. The terms "polysaccharide ether derivative", "polysaccharide ether compound", "polysaccharide ether", and the like are used interchangeably herein. A polysaccharide ether derivative herein is polysaccharide that has been etherified with one or more organic groups (e.g., charged organic group such as anionic or cationic group) such that the derivative has a DoS with one or more organic groups of up to about 3.0. A polysaccharide ether derivative is termed an "ether" herein by virtue of comprising the substructure $-C_G-O-C-$, where "$-C_G-$" represents a carbon atom of a monomeric unit (e.g., glucose) of the polysaccharide ether derivative (where such carbon atom was bonded to a hydroxyl group [—OH] in the polysaccharide precursor of the ether), and where "—C—" is a carbon atom of an organic group. Examples of polysaccharide ethers herein include glucan ethers (e.g., alpha- or beta-glucan ether).

A "carboxy alkyl" group herein refers to a substituted alkyl group in which one or more hydrogen atoms of the alkyl group are substituted with a carboxyl group. A "hydroxy alkyl" group herein refers to a substituted alkyl group in which one or more hydrogen atoms of the alkyl group are substituted with a hydroxyl group. A carboxy alkyl group (e.g., carboxymethyl) is typically anionic in aqueous conditions.

An organic group can refer to a "positively charged organic group". A positively charged organic group as used herein refers to a chain of one or more carbons ("carbon chain") that has one or more hydrogens substituted with another atom or functional group (i.e., a "substituted alkyl group"), where one or more of the substitutions is with a positively charged group. Where a positively charged organic group has a substitution in addition to a substitution with a positively charged group, such additional substitution may be with one or more hydroxyl groups, oxygen atoms (thereby forming an aldehyde or ketone group), alkyl groups, and/or additional positively charged groups. A positively charged organic group has a net positive charge since it comprises one or more positively charged groups. The terms "positively charged group", "positively charged ionic group", "cationic group" and the like are used interchangeably herein. A positively charged group comprises a cation (a positively charged ion). Examples of positively charged groups include substituted ammonium groups, carbocation groups and acyl cation groups.

The terms "substituted ammonium group", "substituted ammonium ion" and "substituted ammonium cation" are used interchangeably herein. A substituted ammonium group herein comprises Structure I:

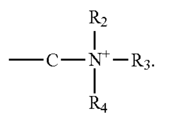

(I)

$R_2$, $R_3$ and $R_4$ in Structure I each independently represent a hydrogen atom or an alkyl, aryl, cycloalkyl, aralkyl, or alkaryl group. The carbon atom (C) in Structure I is part of the chain of one or more carbons ("carbon chain") of the positively charged organic group. The carbon atom is either directly ether-linked to a glucose monomeric unit of an alpha-glucan herein, or is part of a chain of two or more carbon atoms ether-linked to the glucose monomeric unit. The carbon atom in Structure I can be —$CH_2$—, —CH— (where an H is substituted with another group such as a hydroxy group), or —C— (where both H's are substituted).

A substituted ammonium group can be a "primary ammonium group", "secondary ammonium group", "tertiary ammonium group", or "quaternary ammonium" group, depending on the composition of $R_2$, $R_3$ and $R_4$ in Structure I. A primary ammonium group herein refers to Structure I in which each of $R_2$, $R_3$ and $R_4$ is a hydrogen atom (i.e., —C—$NH_3^+$). A secondary ammonium group herein refers to Structure I in which each of $R_2$ and $R_3$ is a hydrogen atom and $R_4$ is an alkyl, aryl, cycloalkyl, aralkyl, or alkaryl group. A tertiary ammonium group herein refers to Structure I in which $R_2$ is a hydrogen atom and each of $R_3$ and $R_4$ is an alkyl, aryl, cycloalkyl, aralkyl, or alkaryl group. A quaternary ammonium group herein refers to Structure I in which each of $R_2$, $R_3$ and $R_4$ is an alkyl, aryl, cycloalkyl, aralkyl, or alkaryl group (i.e., none of $R_2$, $R_3$ and $R_4$ is a hydrogen atom).

A quaternary ammonium alpha-glucan ether herein can comprise a trialkyl ammonium group (where each of $R_2$, $R_3$ and $R_4$ is an alkyl group), for example. A trimethylammonium group is an example of a trialkyl ammonium group, where each of $R_2$, $R_3$ and $R_4$ is a methyl group. It would be understood that a fourth member (i.e., $R_1$) implied by "quaternary" in this nomenclature is the chain of one or more carbons of the positively charged organic group that is ether-linked to a glucose monomeric unit of the alpha-glucan.

An example of a quaternary ammonium alpha-glucan ether is trimethylammonium hydroxypropyl alpha-glucan. The positively charged organic group of this ether compound can be represented as Structure II:

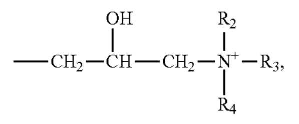

(II)

where each of $R_2$, $R_3$ and $R_4$ is a methyl group. Structure II is an example of a quaternary ammonium hydroxypropyl group.

Terms used herein regarding "esters" (e.g., polysaccharide ester derivative) can be as disclosed, for example, in U.S. Patent Appl. Publ. Nos. 2014/0187767, 2018/0155455, or 2020/0308371, U.S. Appl. No. 63/037,184, or Int. Pat. Appl. Publ. No. WO2021252575, each of which are incorporated herein by reference. The terms "polysaccharide ester derivative", "polysaccharide ester compound", "polysaccharide ester", and the like are used interchangeably herein. A polysaccharide ester derivative herein is polysaccharide that has been esterified with one or more organic groups (i.e., acyl groups) (e.g., charged organic group such as anionic or cationic) such that the derivative has a DoS with one or more organic groups of up to about 3.0. A polysaccharide ester derivative is termed an "ester" herein by virtue of comprising the substructure —$C_G$—O—CO—C—, where "—$C_G$-" represents a carbon atom of a monomeric unit (e.g., glucose) of the polysaccharide ester derivative (where such carbon atom was bonded to a hydroxyl group [—OH] in the polysaccharide precursor of the ester), and where "—CO—C—" is comprised in the acyl group. Examples of polysaccharide esters herein include glucan esters (e.g., alpha- or beta-glucan ester).

The terms "polysaccharide carbamate derivative", "polysaccharide carbamate", "carbamoyl polysaccharide" and the like are used interchangeably herein. A polysaccharide carbamate derivative contains the linkage moiety —OCONH— or

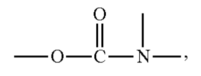

and thus comprises the substructure —$C_G$—OCONH—$C_R$— or —$C_G$—OCON—$C_{R2}$—, where "—$C_G$—" represents a carbon of a monomer unit (e.g., glucose) of the polysaccharide carbamate derivative, and "—$C_R$—" is comprised in the organic group. In some aspects, the nitrogen atom of a carbamate/carbamoyl moiety is linked to a hydrogen atom and an organic group. In some aspects, however, the nitrogen atom of a carbamate/carbamoyl moiety is linked to two organic groups (as indicated by "—$C_{R2}$" above), which can be the same (e.g., two methyl groups, two ethyl groups) or different (e.g., a methyl group and an ethyl group). Examples of polysaccharide carbamates herein include glucan carbamates (e.g., alpha- or beta-glucan carbamate).

The terms "polysaccharide sulfonyl derivative", "sulfonyl polysaccharide" and the like are used interchangeably herein. A polysaccharide sulfonyl derivative contains the linkage moiety —$OSO_2$—, and thus comprises the substructure —$C_G$—O—$SO_2$—$C_R$—, where "—$C_G$—" represents a carbon of a monomer unit (e.g., glucose) of the polysaccharide sulfonyl derivative, and "—$C_R$—" is comprised in the organic group. A sulfonyl linkage herein is not ionizable. Sulfonyl groups of a polysaccharide sulfonyl derivative herein can be as disclosed, for example, in U.S. Appl. No. 63/037,076 or Int. Pat. Appl. Publ. No. WO2021/252569, which are incorporated herein by reference.

A "sulfonate" group herein can be as disclosed, for example, in Int. Pat. Appl. Publ. No. WO2019/246228, which is incorporated herein by reference.

The terms "fiber", "fibers" and the like herein refer to staple fibers (staple length fibers) and continuous fibers, in some aspects. Fibers herein can comprise alpha-1,3-glucan, natural fiber (e.g., cellulose, cotton, wool, silk), or synthetic fiber (e.g., polyester), or any other type of material disclosed herein that can form a fiber.

The terms "fabric", "textile", "cloth" and the like are used interchangeably herein to refer to a woven material having a network of natural and/or artificial fibers. Such fibers can be in the form of thread or yarn, for example.

The terms "non-woven", "non-woven product", "non-woven web" and the like herein refer to a web of individual fibers or filaments that are interlaid, typically in a random or unidentifiable manner. This contrasts with a knitted or woven fabric, which has an identifiable network of fibers or filaments. In some aspects, a non-woven product comprises a non-woven web that is bound or attached to another material such as a substrate or backing. A non-woven in some aspects can further contain a binder or adhesive (strengthening agent) that binds adjacent non-woven fibers together. A non-woven binder or adhesive agent can be applied to the non-woven in the form of a dispersion/latex, solution, or solid, for example, and then the treated non-woven is typically dried.

The terms "household care product", "home care product", and like terms typically refer to products, goods and services relating to the treatment, cleaning, caring, and/or conditioning of a home and its contents. The foregoing includes, for example, chemicals, compositions, products, or combinations thereof having application in such care.

A "fabric care composition", "laundry care composition", and like terms refer to any composition suitable for treating fabric, non-wovens, and/or any similar material in some manner. Examples of such a composition include laundry detergents and fabric softeners.

A "detergent composition" herein typically comprises at least a surfactant (detergent compound) and/or a builder. A "surfactant" herein refers to a substance that tends to reduce the surface tension of a liquid in which the substance is dissolved. A surfactant may act as a detergent, wetting agent, emulsifier, foaming agent, and/or dispersant, for example.

The terms "heavy duty detergent", "all-purpose detergent" and the like are used interchangeably herein to refer to a detergent useful for regular washing of white and colored textiles at any temperature. The terms "low duty detergent", "fine fabric detergent" and the like are used interchangeably herein to refer to a detergent useful for the care of delicate fabrics such as viscose, wool, silk, microfiber or other fabric requiring special care. "Special care" can include conditions of using excess water, low agitation, and/or no bleach, for example.

The terms "builder", "builder agent" and the like herein refer to compositions that, for example, can complex with hard water cations such as calcium and magnesium cations. Such complex formation is believed to prevent the formation of water-insoluble salts and/or other complexes by the cation(s). In the context of a detergent composition for cleaning or maintenance applications, a builder added thereto typically can enhance or maintain the cleaning efficiency of a surfactant present in the detergent composition. The terms "builder capacity", "builder activity" and the like are used interchangeably herein and refer to the ability of an aqueous composition to exhibit features endowed by one or more builders present in the aqueous composition. A composition herein in some aspects can be used as a builder.

The terms "fabric softener", "fabric conditioner" and the like herein refer to compositions, such as in liquid or solid form, that deposit lubricants and/or other surface-modifying ingredients onto fabric to, for example, help maintain softness of the fabric and/or provide other beneficial features to fabric (e.g., lubricity, anti-static, anti-cling, and/or anti-wrinkling). A fabric softener herein typically is applied to fabric following fabric washing with a laundry detergent, usually while rinsing the fabric.

The term "personal care product" and like terms typically refer to products, goods and services relating to the treatment, cleaning, cleansing, caring or conditioning of a person. The foregoing include, for example, chemicals, compositions, products, or combinations thereof having application in such care.

The term "medical product" and like terms typically refer to products, goods and services relating to the diagnosis, treatment, and/or care of patients.

The term "industrial product" and like terms typically refer to products, goods and services used in industrial or institutional settings, but typically not by individual consumers.

The terms "ingestible product", "ingestible composition" and the like refer to any substance that, either alone or together with another substance, may be taken orally (i.e., by mouth), whether intended for consumption or not. Thus, an ingestible product includes food/beverage products. "Food/beverage products" refer to any edible product intended for consumption (e.g., for nutritional purposes) by humans or animals, including solids, semi-solids, or liquids. A "food" herein can optionally be referred to as a "foodstuff", "food product", or other like term, for example. "Non-edible products" ("non-edible compositions") refer to any composition that can be taken by the mouth for purposes other than food or beverage consumption. Examples of non-edible products herein include supplements, nutraceuticals, functional food products, pharmaceutical products, oral care products (e.g., dentifrices, mouthwashes), and cosmetic products such as sweetened lip balms. A "pharmaceutical product", "medicine", "medication", "drug" or like term herein refers to a composition used to treat disease or injury, and can be administered enterally or parenterally.

The terms "film", "sheet" and like terms herein refer to a generally thin, visually continuous material. A film can be comprised as a layer or coating on a material, or can be alone (e.g., not attached to a material surface; free-standing). A "coating" (and like terms) as used herein refers to a layer covering a surface of a material. The term "uniform thickness" as used to characterize a film or coating herein can refer to a contiguous area that (i) is at least 20% of the total film/coating area, and (ii) has a standard deviation of thickness of less than about 50 nm, for example. The term "continuous layer" means a layer of a composition applied to at least a portion of a substrate, wherein a dried layer of the composition covers 299% of the surface to which it has been applied and having less than 1% voids in the layer that expose the substrate surface. The 299% of the surface to which the layer has been applied excludes any area of the substrate to which the layer has not been applied. A coating herein can make a continuous layer in some aspects. A coating composition (and like terms) herein refers to all the solid components that form a layer on a substrate, such as particles herein and, optionally, pigment, surfactant, dispersing agent, binder, crosslinking agent, and/or other additives.

The term "paint" (and like terms) herein is a type of coating composition that is a dispersion of a pigment in a suitable liquid (e.g., aqueous liquid) that can be used to form an adherent coating when spread on a surface in a thin coat. Paint as applied to a surface can provide coloration/decoration, protection, and/or treatment (e.g., primer) to the surface. A paint herein, by virtue of further comprising dispersed particles herein, can optionally be characterized as a latex or latex paint.

A "composite" herein comprises two or more components including a composition (e.g., particles) of the present disclosure. Typically, the components of a composite resist separation and one or more of the components display enhanced and/or different properties as compared to its properties alone, outside the composite (i.e., a composite is not simply an admixture, which generally is easily separable to its original components). A composite herein generally is a solid material, and can be made via an extrusion or molding process, for example.

The terms "flocculant", "flocculation agent", "flocculation composition", "agglomeration agent", and the like herein refer to substances that can promote agglomeration/clumping/coalescence of insoluble particles suspended in water or other aqueous liquid, thereby rendering the particles more easy to remove by settling/sedimentation, filtration, pelleting, and/or other suitable means. Flocculation of particles typically can be performed in a process of removing/separating particles from an aqueous suspension. A composition herein in some aspects can be used as a flocculant.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "weight/volume percent", "w/v %" and the like are used interchangeably herein. Weight/volume percent can be calculated as: ((mass [g] of material)/(total volume [mL] of the material plus the liquid in which the material is placed))×100%. The material can be insoluble in the liquid (i.e., be a solid phase in a liquid phase, such as with a dispersion), or soluble in the liquid (i.e., be a solute dissolved in the liquid).

The term "isolated" means a substance (or process) in a form or environment that does not occur in nature. A non-limiting example of an isolated substance includes any alpha-glucan composition disclosed herein. It is believed that the embodiments disclosed herein are synthetic/man-made (could not have been made or practiced except for human intervention/involvement), and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

Some aspects of the present disclosure concern a composition comprising at least an insoluble alpha-glucan and a soluble alpha-glucan derivative, wherein at least about 50% of the glycosidic linkages of the insoluble alpha-glucan are alpha-1,3 glycosidic linkages, and the weight-average degree of polymerization (DPw) of the insoluble alpha-glucan is at least 15 (or at least 10), and wherein at least about 50% of the glycosidic linkages of the soluble alpha-glucan derivative are alpha-1,3 glycosidic linkages, and the DPw of the alpha-glucan portion of the soluble alpha-glucan derivative is at least 15 (or at least 10). Such compositions as presently disclosed have several advantageous features. For example, as compared to insoluble alpha-1,3-glucan dispersed alone in an aqueous dispersion, dispersing the presently disclosed composition, which has both insoluble alpha-1,3-glucan and soluble alpha-1,3-glucan derivative components, results in the aqueous composition having a lower viscosity. Thus, the presently disclosed compositions offer enhanced processing benefits due to the ease in which lower viscosity compositions can be handled. Another advantage of the disclosed compositions is that the microstructure of the insoluble alpha-1,3-glucan is preserved and protected from agglomeration and other denaturing effects typically observed when drying dispersed (or other wet forms of) insoluble alpha-1,3-glucan alone.

A composition of the present disclosure comprises insoluble alpha-glucan, wherein at least about 50% of the glycosidic linkages of the insoluble alpha-glucan are alpha-1,3 glycosidic linkages. In some aspects, about, or at least about, 50%, 60%, 70%, 80%, 85%, 90%, 91%, 92%, 93%, 94%, 95%, 96%, 97%, 98%, 99%, 99.5%, or 100% of the glycosidic linkages of insoluble alpha-glucan are alpha-1,3 glycosidic linkages. Typically, the glycosidic linkages that are not alpha-1,3 are mostly or entirely alpha-1,6. It should be understood that the higher the percentage of alpha-1,3 linkages present in an insoluble alpha-glucan, the greater the probability that the glucan is linear, since there are lower occurrences of certain linkages that might be part of branch points. In some aspects, insoluble alpha-glucan has no branch points or less than about 5%, 4%, 3%, 2%, or 1% branch points as a percent of the glycosidic linkages in the alpha-glucan.

Insoluble alpha-glucan of the disclosed composition can have a DPw of at least about 15. In some aspects, the DPw, DPn, or DP of insoluble alpha-glucan can be about, less than about, at least about, or over about, 10, 15, 20, 25, 30, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 125, 150, 200, 300, 400, 500, 600, 700, 800, 900, 1000, 1100, 1200, 1300, 1400, 1500, 1600, 1700, 1800, 1900, 2000, 2500, 3000, 3500, or 4000. DPw, DPn, or DP can optionally be expressed as a range between any two of these values. Merely as examples, the DPw, DPn, or DP of insoluble alpha-glucan herein can be about 15-1600, 50-1600, 100-1600, 200-1600, 300-1600, 400-1600, 500-1600, 600-1600, 700-1600, 15-1250, 50-1250, 100-1250, 200-1250, 300-1250, 400-1250, 500-1250, 600-1250, 700-1250, 15-1000, 50-1000, 100-1000, 200-1000, 300-1000, 400-1000, 500-1000, 600-1000, 700-1000, 15-900, 50-900, 100-900, 200-900, 300-900, 400-900, 500-900, 600-900, 700-900, 600-800, or 600-750. Merely as further examples, the DPw, DPn, or DP of insoluble alpha-glucan herein can be about 15-100, 25-100, 35-100, 15-80, 25-80, 35-80, 15-60, 25-60, 35-60, 15-55, 25-55, 35-55, 15-50, 25-50, 35-50, 35-45, 35-40, 40-100, 40-80, 40-60, 40-55, 40-50, 45-60, 45-55, 45-50, 15-35, 20-35, 15-30, or 20-30. In some aspects, an insoluble alpha-glucan can have a high molecular weight as reflected by high intrinsic viscosity (IV); e.g., IV can be about, or at least about 6, 7, 8, 9, 10, 11, 12, 13, 14, 15, 16, 17, 18, 19, 20, 21, 22, 6-8, 6-7, 6-22, 6-20, 6-17, 6-15, 6-12, 10-22, 10-20, 10-17, 10-15, 10-12, 12-22, 12-20, 12-17, or 12-15 dL/g. For comparison purposes, note that the IV of alpha-glucan with at least 90% (e.g., about 99% or 100%) alpha-1,3 linkages and a DPw of about 800 has an IV of about 2-2.5 dL/g. IV herein can be as measured with alpha-glucan polymer dissolved in DMSO with about 0.9 to 2.5 wt % (e.g., 1, 2, 1-2 wt %) LiCl, for example.

Insoluble alpha-glucan herein can be as disclosed (e.g., molecular weight, linkage profile, and/or production method), for example, in U.S. Pat. Nos. 7,000,000, 8,871, 474, 10,301,604, or 10,260,053, or U.S. Patent Appl. Publ. Nos. 2019/0112456, 2019/0078062, 2019/0078063, 2018/0340199, 2018/0021238, 2018/0273731, 2017/0002335, 2015/0232819, 2015/0064748, 2020/0165360, 2020/0131281, or 2019/0185893, which are each incorporated herein by reference. Insoluble alpha-glucan can be produced, for example, by an enzymatic reaction comprising at least water, sucrose and a glucosyltransferase enzyme that synthesizes the insoluble alpha-glucan. Glucosyltransferases, reaction conditions, and/or processes contemplated to be useful for producing insoluble alpha-glucan can be as disclosed in any of the foregoing references.

In some aspects, a glucosyltransferase enzyme for producing an insoluble alpha-glucan can comprise an amino acid sequence that is 100% identical to, or at least 90%, 91%, 92%, 93%, 94%, 95%, 96%, 97%, 98%, 98.5%, 99%, or 99.5% identical to, SEQ ID NO:2, 4, 6, 8, 10, 12, 14, 16, 18, 20, 26, 28, 30, 34, or 59, or amino acid residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20, and have glucosyltransferase activity; these amino acid sequences are disclosed in U.S. Patent Appl. Publ. No. 2019/0078063, which is incorporated herein by reference. It is noted that a glucosyltransferase enzyme comprising SEQ ID NO:2, 4, 8, 10, 14, 20, 26, 28, 30, 34, or amino acid residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20, can synthesize insoluble alpha-glucan comprising at least about 90% (~100%) alpha-1,3 linkages.

In some aspects, insoluble alpha-glucan can be in the form of an insoluble graft copolymer such as disclosed in Int. Patent Appl. Publ. Nos. WO2017/1079595 or WO2021/247810, or U.S. Patent Appl. Publ. Nos. 2020/0165360, 2019/0185893, or 2020/0131281, which are incorporated herein by reference. A graft copolymer can comprise dextran (as backbone) and alpha-1,3-glucan (as one or more side chains), where the latter component has been grafted onto the former component; typically, this graft copolymer is produced by using dextran or alpha-1,2- and/or alpha-1,3-branched dextran as a primer for alpha-1,3-glucan synthesis by an alpha-1,3-glucan-producing glucosyltransferase as described above. Alpha-1,3-glucan side chain(s) of an alpha-glucan graft copolymer herein can be alpha-1,3-glucan as presently disclosed. Dextran backbone of an alpha-glucan graft copolymer herein can comprise about 100% alpha-1,6 glycosidic linkages (i.e., completely linear dextran backbone), or about, or at least about, 90%, 95%, 96%, 97%, 98%, 99%, or 99.5% alpha-1,6 glycosidic linkages (i.e., substantially linear dextran backbone), and/or have a DP or DPw of about, at least about, or less than about, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 85, 90, 95, 100, 105, 110, 150, 200, 250, 300, 400, 500, 8-20, 8-30, 8-100, 8-500, 3-4, 3-5, 3-6, 3-7, 3-8, 4-5, 4-6, 4-7, 4-8, 5-6, 5-7, 5-8, 6-7, 6-8, 7-8, 90-120, 95-120, 100-120, 105-120, 110-120, 115-120, 90-115, 95-115, 100-115, 105-115, 110-115, 90-110, 95-110, 100-110, 105-110, 90-105, 95-105, 100-105, 90-100, 95-100, 90-95, 85-95, or 85-90, for example. The molecular weight of a dextran backbone in some aspects can be about, or at least about, 0.1, 0.125, 0.15, 0.175, 0.2, 0.24, 0.25, 0.5, 0.75, 1, 2, 3, 4, 5, 6, 7, 8, 9, 10, 20, 30, 40, 50, 60, 70, 80, 90, 100, 110, 120, 130, 140, 150, 160, 170, 180, 190, 200, 0.1-0.2, 0.125-0.175, 0.13-0.17, 0.135-0.165, 0.14-0.16, 0.145-0.155, 10-80, 20-70, 30-60, 40-50, 50-200, 60-200, 70-200, 80-200, 90-200, 100-200, 110-200, 120-200, 50-180, 60-180, 70-180, 80-180, 90-180, 100-180, 110-180, 120-180, 50-160, 60-160, 70-160, 80-160, 90-160, 100-160, 110-160, 120-160, 50-140, 60-140, 70-140, 80-140, 90-140, 100-140, 110-140, 120-140, 50-120, 60-120, 70-120, 80-120, 90-120, 90-110, 100-120, 110-120, 50-110,60-110, 70-110, 80-110, 90-110, 100-110, 50-100, 60-100, 70-100, 80-100, 90-100, or 95-105 million Daltons. In some aspects, a dextran backbone (before being integrated into a graft copolymer) has been alpha-1,2- and/or alpha-1,3-branched; the percent alpha-1,2 and/or alpha-1,3 branching of a backbone of a graft copolymer herein can be about, at least about, or less than about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 2-25%, 2-20%, 2-15%, 2-10%, 5-25%, 5-20%, 5-15%, 5-10%, 7-13%, 8-12%, 9-11%, 10-25%, 10-20%, 10-15%, 10-22%, 12-20%, 12-18%, 14-20%, 14-18%, 15-18%, or 15-17%, for example. The dextran portion of a graft copolymer herein can be as disclosed (e.g., molecular weight, linkage/branching profile, production method), for example, in U.S. Patent Appl. Publ. Nos. 2016/0122445, 2017/0218093, 2018/0282385, 2020/0165360, or 2019/0185893, which are each incorporated herein by reference. In some aspects, a dextran can be one produced in a suitable reaction comprising glucosyltransferase (GTF) 0768 (SEQ ID NO:1 or 2 of US2016/10122445), GTF 8117, GTF 6831, or GTF 5604 (these latter three GTF enzymes are SEQ ID NOs:30, 32 and 33, respectively, of US2018/0282385), or a GTF comprising an amino acid sequence that is at least 90%, 91%, 92%, 93%, 94%, 95%, 96%, 97%, 98%, or 99% identical to the amino acid sequence of GTF 0768, GTF 8117, GTF 6831, or GTF 5604. In some aspects, an alpha-glucan graft copolymer can comprise: (A) an alpha-1,6-glucan backbone (100% alpha-1,6-linked before alpha-1,2 and/or alpha-1,3 branching) that (i) has been branched with about 10-22% (e.g., about 12-20%, 12-18%, 14-20%, 14-18%, 15-18%, 15-17%, or 16%) alpha-1,2 and/or alpha-1,3 linkages (i.e., alpha-1,2,6 and/or alpha-1,3,6) (e.g., the backbone in total comprises about 82-86% or 84% alpha-1,6 linkages and about 14-18% or 16% alpha-1,2 and/or alpha-1,3 linkages) and (ii) has an Mw of about 15-25, 15-22.5, 17-25, 17-22.5, 18-22, or 20 kDa, and (B) one or more (e.g., two, three, four, five, or six) alpha-1,3-glucan side chains that have been extended from one or more of the alpha-1,2 and/or alpha-1,3 branches; such a graft copolymer typically is water-insoluble.

Insoluble alpha-glucan for use in preparing a composition of the present disclosure can be in the form of particles in some aspects. As comprised in an aqueous composition such as a dispersion, about 40-60%, 40-55%, 45-60%, 45-55%, 47-53%, 48-52%, 49-51%, or 50% by weight of such insoluble alpha-glucan particles have a diameter (i.e., $D_{50}$)

of about, less than about, or at least about, 1, 2, 3, 4, 5, 6, 7, 8, 9, 10, 11, 12, 13, 14, 15, 16, 17, 18, 19, 20, 21, 22, 23, 24, 25, 1-25, 1-22, 1-20, 1-18, 5-25, 5-22, 5-20, 5-18, 15-22, 15-20, 15-18, 16-22, 16-20, or 16-18 microns, for example.

Insoluble alpha-glucan herein typically does not have any chemical derivatization (e.g., etherification, esterification, phosphorylation, sulfation, oxidation, carbamation) (e.g., no substitution of hydrogens of glucan hydroxyl groups with a non-sugar chemical group). However, in some aspects, insoluble alpha-glucan can be a charged (e.g., cationic or anionic) derivative of an alpha-glucan as disclosed herein. The DoS of such a derivative typically is less than about 0.3, 0.25, 0.2, 0.15, 0.1, or 0.05. The type of derivative can be any of the derivatives disclosed herein (e.g., ether, ester). Typically, insoluble alpha-glucan herein is enzymatically derived in an inert vessel (typically under cell-free conditions) and is not derived from a cell wall (e.g., fungal cell wall).

Insoluble alpha-glucan of the disclosed composition can be in the form of fibrids in some aspects. The alpha-glucan of fibrids can have a linkage profile and/or molecular weight as disclosed above, for example. Alpha-glucan fibrids herein can be as disclosed and/or produced in U.S. Pat. Appl. Publ. No. 2018/0119357, for example, which is incorporated herein by reference. Fibrids herein typically comprise insoluble alpha-glucan as disclosed herein, which is non-derivatized. However, in some aspects, fibrids can comprise an insoluble, charged (e.g., cationic or anionic) derivative (e.g., ether) of an alpha-glucan as disclosed herein. The DoS of such a derivative typically is less than about 0.3, 0.25, 0.2, 0.15, 0.1, or 0.05.

A composition of the present disclosure can, in some aspects, comprise insoluble alpha-glucan that is in the form of particles having a degree of crystallinity of at least about 0.65. The degree of crystallinity (or crystallinity index [CI]) of insoluble alpha-glucan particles herein can be about, or at least about, 0.55, 0.60, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.60-0.83, 0.65-0.83, 0.67-0.83, 0.69-0.83, 0.60-0.81, 0.65-0.81, 0.67-0.81, 0.69-0.81, 0.60-0.78, 0.65-0.78, 0.67-0.78, 0.69-0.78, 0.60-0.76, 0.65-0.76, 0.67-0.76, or 0.69-0.76, for example. In general, that portion of insoluble alpha-glucan herein that is not crystalline is amorphous. Flowing from the foregoing crystallinity values, the wt % of particles that is amorphous is about, or less than about, 45%, 40%, 35%, 30%, 25%, 20%, or 15%, for example. The degree of crystallinity of alpha-glucan particles herein can be as when measured according to any suitable method, such as follows. A sample of insoluble alpha-glucan herein is dried for at least about 2 hours (e.g., 8-12 hours) in a vacuum oven set at about 55-65° C. (e.g., 60° C.). The sample is then be packed into a stainless steel holder with a well of about 1-2 cm wide by 3-5 cm long by 3-5 mm deep, after which the holder is loaded into a suitable diffractometer (e.g., X'PERT MPD POWDER diffractometer, PANalytical B.V., The Netherlands) set in reflection mode to measure the X-ray diffraction pattern of the sample. The X-ray source is a Cu X-ray tube line source with an optical focusing mirror and a ~1/16° narrowing slit. X-rays are detected with a 1-D detector and an anti-scatter slit set at ~1/8°. Data are collected in the range of about 4 to 60 degrees of two-theta at about 0.1 degrees per step. The resulting X-ray pattern is then analyzed by subtracting a linear baseline from about 7.2 to 30.5 degrees, subtracting the XRD pattern of a known amorphous alpha-1,3-glucan sample that has been scaled to fit the data, and then fitting the remaining crystal peaks in that range with a series of Gaussian curves corresponding to known dehydrated alpha-1,3-glucan crystal reflections. The area corresponding to the crystal peaks is then divided by the total area under the baseline-subtracted curve to yield a crystallinity index. Insoluble alpha-glucan with any of the foregoing degrees of crystallinity can have a DP, DPw, or DPn of about 15 to 100 (e.g., any molecular weight disclosed herein falling in this range), for example.

At least about 80 wt % of particles of insoluble alpha-glucan having any of the foregoing degrees of crystallinity can be in the form of plates, for example. In some aspects, about, or at least about, 60, 65, 70, 75, 80, 81, 82, 83, 84, 85, 86, 87, 88, 89, 90, 91, 92, 93, 94, 95, 96, 97, 98, 99, 60-85, 60-80, 60-75, 60-70, 65-85, 65-80, 65-75, 65-70, 70-85, 70-80, or 70-75 wt % of the particles of insoluble alpha-glucan are in the form of plates. Plates of insoluble alpha-glucan herein can be visually appreciated when viewed by electron microscopy such as TEM or SEM, for example. Typically, the balance of particles of insoluble alpha-glucan are of non-plate form. In some aspects, the balance of the particles that are of non-plate form can be characterized as being fibrillar and/or striated in appearance. However, in some aspects, about, or at least about, 10, 20, 30, 40, 50, 60, or 70 wt % of the particles of insoluble alpha-glucan in a composition herein are in the form of plates.

In some aspects, at least about 65% by weight of insoluble alpha-glucan particles having any of the foregoing degrees of crystallinity have a diameter of less than 1.0 micron. Yet, in some aspects, about, or at least about, 65%, 70%, 75%, 80%, 85%, 90%, 95%, 65-95%, 70-95%, 75-95%, 80-95%, 85-95%, 65-90%, 70-90%, 75-90%, 80-90%, 85-90%, 65-85%, 70-85%, 75-85%, or 80-85% by weight of insoluble alpha-glucan particles have a diameter of less than about 1.0 micron. In some aspects, about 40-60%, 40-55%, 45-60%, 45-55%, 47-53%, 48-52%, 49-51%, or 50% by weight of the insoluble alpha-glucan particles have a diameter of about, or less than about, 1.0, 0.9, 0.8, 0.7, 0.6, 0.5, 0.4, 0.35, 0.34, 0.32, 0.30, 0.28, 0.26, 0.25, 0.24, 0.23, 0.22, 0.21, 0.20, 0.19, 0.18, 0.17, 0.16, 0.15, 0.14, 0.13, 0.12, 0.11, 0.10, 0.10-1.0, 0.10-0.80, 0.10-0.60, 0.10-0.40, 0.10-0.35, 0.10-0.30, 0.10-0.25, 0.10-0.20, 0.15-0.35, 0.15-0.30, 0.15-0.25, or 0.15-0.20 micron. In some aspects, about 40-60%, 40-55%, 45-60%, 45-55%, 47-53%, 48-52%, 49-51%, or 50% by weight of insoluble alpha-glucan particles are aggregates of the foregoing smaller diameter particles, and have a diameter of about, less than about, or at least about, 10, 25, 50, 100, 150, 200, 250, 300, 350, 400, 450, 500, 550, 600, 10-600, 10-550, 10-500, 50-600, 50-550, 50-500, 100-600, 100-550, 100-500, 150-600, 150-550, 150-500, 200-600, 200-550, 200-500, 250-600, 250-550, or 250-500 microns. Alpha-glucan particles having any of the foregoing degrees of crystallinity can have a thickness of about 0.010, 0.015, 0.020, 0.025, 0.030, or 0.010-0.030 micron, for example; such a thickness can optionally be in conjunction with any of the foregoing diameter aspects. The foregoing particle size and/or distributions for crystalline particles herein can be as measured for particles comprised in an aqueous dispersion, and/or as measured using a light scatter technique, for example.

Insoluble alpha-glucan in the form of particles having a degree of crystallinity of at least about 0.65 can be produced, for example, by a method comprising the following steps: (a) providing insoluble alpha-glucan (precursor) as produced in an enzymatic reaction comprising at least water, sucrose and a glucosyltransferase enzyme that synthesizes the insoluble alpha-glucan, wherein the insoluble alpha-glucan has a DPw or DPn of at least about, or over about, 100, 150, or 200, and at least 50% of its glycosidic linkages are alpha-1,3 glycosidic linkages; (b) hydrolyzing the insoluble alpha-glucan (precursor) to insoluble alpha-glucan particles with a DPw or DPn, for example, of about 10 to 100 (e.g., any DPw or DPn value herein falling in this range), wherein the hydrolyzing is performed under aqueous conditions at a pH of 2.0 or less, and (c) optionally isolating the insoluble alpha-glucan particles produced in step (b). Step (b) of this method can optionally be characterized as an "acid hydrolysis" method or reaction. Insoluble alpha-glucan precursor herein for entry into acid hydrolysis is itself insoluble alpha-glucan, but has a molecular weight that is greater than that of the insoluble alpha-glucan produced by the hydrolysis method. An insoluble alpha-glucan precursor can have a glycosidic linkage profile as disclosed above (e.g., at least about 50%, 60%, 70%, 80%, 90%, 95%, 99%, 99.5%, or 100% alpha-1,3 glycosidic linkages) and a DPw or DPn of about, at least about, or over about, 200 (e.g., any such DPw or DPn as disclosed above). An acid hydrolysis herein can be performed as described in the Examples below, for example.

A composition of the present disclosure can comprise at least one soluble alpha-glucan derivative, wherein at least about 50% of the glycosidic linkages of the soluble alpha-glucan derivative are alpha-1,3 glycosidic linkages, and the soluble alpha-glucan has a DPw of at least about 15. Such a derivative can be that of any insoluble alpha-glucan as disclosed elsewhere herein, for example, just so long as the derivative is aqueous-soluble. For example, the alpha-glucan portion of a soluble alpha-glucan derivative herein can have a molecular weight (e.g., DP, DPw, or DPn) and/or glycosidic linkage profile as disclosed herein for an insoluble alpha-glucan. Merely as examples, an insoluble alpha-glucan herein that can be derivatized to be a soluble alpha-glucan derivative can comprise (i) alpha-glucan (e.g., with ≥ about 50%, 90%, 95%, 99%, or 100% alpha-1,3 linkages) with a DPw over 15 (e.g., ≥100,400, 600) or (ii) an alpha-glucan graft copolymer herein. A composition in some aspects comprises one, two, three, four, or more different types of soluble alpha-glucan derivative. Typically herein, it is the derivatization of an insoluble alpha-glucan that renders it to be soluble.

A soluble alpha-glucan derivative in some aspects can have a degree of substitution (DoS) up to about 3.0 (e.g., 0.3 to 3.0) with at least one organic group/substituent as presently disclosed. An organic group herein can be charged, for example; i.e., the organic group can be cationic (positively charged) or anionic (negatively charged). The DoS can be about, or at least about, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 (DoS can optionally be expressed as a range between any two of these values), for example. Some examples of DoS ranges herein for a soluble alpha-glucan derivative include 0.3-3.0, 0.3-2.5, 0.3-2.0, 0.3-1.75, 0.3-1.5, 0.3-1.25, 0.3-1.0, 0.3-0.9, 0.3-0.8, 0.3-0.7, 0.3-0.6, 0.3-0.5, 0.4-3.0, 0.4-2.5, 0.4-2.0, 0.4-1.75, 0.4-1.5, 0.4-1.25, 0.4-1.0, 0.4-0.9, 0.4-0.8, 0.4-0.7, 0.4-0.6, 0.4-0.5, 0.5-3.0, 0.5-2.5, 0.5-2.0, 0.5-1.75, 0.5-1.5, 0.5-1.25, 0.5-1.0, 0.5-0.9, 0.5-0.8, 0.5-0.7, 0.5-0.6, 0.6-3.0, 0.6-2.5, 0.6-2.0, 0.6-1.75, 0.6-1.5, 0.6-1.25, 0.6-1.0, 0.6-0.9, 0.6-0.8, 0.6-0.7, 0.8-3.0, 0.8-2.5, 0.8-2.0, 0.8-1.75, 0.8-1.5, 0.8-1.25, 0.8-1.0, and 0.8-0.9. It would be understood by those skilled in the art that, since a soluble alpha-glucan derivative herein has a DoS (e.g., about 0.3 to about 3.0) with at least one type of organic group, all the substituents of a glucan derivative cannot only be hydroxyl.

A soluble alpha-glucan derivative in some aspects is substituted with at least one organic group herein via an ether linkage, ester linkage, carbamate linkage, or sulfonyl linkage. Thus, a soluble alpha-glucan derivative herein can be a soluble alpha-glucan ether, ester, carbamate, or sulfonyl derivative, for example. All the various linked groups disclosed herein are examples of organic groups; an organic group can be considered to comprise at least one carbon atom and at least one hydrogen atom, for example.

A soluble alpha-glucan derivative is an ether derivative in some aspects. Such a derivative can be termed as a soluble alpha-glucan ether, for example.

An organic group that is in ether-linkage to an alpha-glucan herein can be a positively charged (cationic) group, for example. A positively charged group can be, for example, any of those disclosed in U.S. Pat. Appl. Publ. Nos. 2016/0311935, 2018/0237816, or 2020/10002646, or Int. Pat. Appl. Publ. No. WO2021/257786, which are incorporated herein by reference. A positively charged group can comprise a substituted ammonium group, for example. Examples of substituted ammonium groups are primary, secondary, tertiary and quaternary ammonium groups, such as can be represented by Structures I and 11. An ammonium group can be substituted with alkyl group(s) and/or aryl group(s), for example. There can be one, two, or three types of alkyl and/or aryl groups in some aspects of a substituted ammonium group. An alkyl group of a substituted ammonium group herein can be a $C_1$-$C_{30}$ alkyl group, for example, such as a methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, $C_{25}$, $C_{26}$, $C_{27}$, $C_{21}$, $C_{29}$, or $C_{30}$ group; each alkyl group can be the same or different in aspects with two or three alkyl substitutions. An alkyl group can be $C_1$-$C_{24}$, $C_1$-$C_{18}$, $C_6$-$C_{20}$, $C_{10}$-$C_{16}$, or $C_1$-$C_4$ in some aspects. An aryl group can be a $C_6$, $C_6$-$C_{24}$, $C_6$-$C_{24}$, or $C_6$-$C_{18}$ aryl group, for example, that is optionally substituted with one or more alkyl substituents (e.g., any alkyl group disclosed herein).

A secondary ammonium alpha-glucan ether herein can comprise a monoalkylammonium group in some aspects (e.g., based on Structure 1). A secondary ammonium alpha-glucan ether can be a monoalkylammonium alpha-glucan ether in some aspects, such as a monomethyl-, monoethyl-, monopropyl-, monobutyl-, monopentyl-, monohexyl-, monoheptyl-, monooctyl-, monononyl-, monodecyl-, monoundecyl-, monododecyl-, monotridecyl-, monotetradecyl-, monopentadecyl-, monohexadecyl-, monoheptadecyl-, or monooctadecyl-ammonium alpha-glucan ether. These alpha-glucan ethers can also be referred to as methyl-, ethyl-, propyl-, butyl-, pentyl-, hexyl-, heptyl-, octyl-, nonyl-, decyl-, undecyl-, dodecyl-, tridecyl-, tetradecyl-, pentadecyl-, hexadecyl-, heptadecyl-, or octadecyl-ammonium alpha-glucan ethers, respectively.

A tertiary ammonium alpha-glucan ether herein can comprise a dialkylammonium group in some aspects (e.g., based on Structure 1). A tertiary ammonium alpha-glucan ether can be a dialkylammonium alpha-glucan ether in some aspects, such as a dimethyl-, diethyl-, dipropyl-, dibutyl-, dipentyl-, dihexyl-, diheptyl-, dioctyl-, dinonyl-, didecyl-, diundecyl-, didodecyl-, ditridecyl-, ditetradecyl-, dipentadecyl-, dihexadecyl-, diheptadecyl-, or dioctadecyl-ammonium alpha-glucan ether.

A quaternary ammonium alpha-glucan ether herein can comprise a trialkylammonium group in some aspects (e.g., based on Structure 1). A quaternary ammonium alpha-glucan ether compound can be a trialkylammonium alpha-glucan ether in some aspects, such as trimethyl-, triethyl-, tripropyl-, tributyl-, tripentyl-, trihexyl-, triheptyl-, trioctyl-, trinonyl-, tridecyl-, triundecyl-, tridodecyl-, tritridecyl-, tritetradecyl-, tripentadecyl-, trihexadecyl-, triheptadecyl-, or trioctadecyl-ammonium alpha-glucan ether.

One of the groups of a substituted ammonium group comprises one carbon, or a chain of carbons (e.g., up to 30), in ether linkage to an alpha-glucan. A carbon chain in this context can be linear, for example. Such a carbon or carbon chain can be represented by $—CH_2—$, $—CH_2CH_2—$, $—CH_2CH_2CH_2—$, $—CH_2(CH_2)_2CH_2—$, $—CH_2(CH_2)_3CH_2—$, $—CH_2CH_2)_4CH_2—$, $—CH_2CH_2)_5CH_2—$, $—CH_2(CH_2)_6CH_2—$, $—CH_2(CH_2)_7CH_2—$, $—CH_2(CH_2)_8CH_2—$, $—CH_2CH_2)_9CH_2—$, or $—CH_2(CH_2)_{10}CH_2—$, for example. In some aspects, a carbon chain in this context can be branched, such as by being substituted with one or more alkyl groups (e.g., any as disclosed above such as methyl, ethyl, propyl, or butyl). The point(s) of substitution can be anywhere along the carbon chain. Examples of branched carbon chains include $—CH(CH_3)CH_2—$, $—CH(CH_3)CH_2CH_2—$, $—CH_2CH(CH_3)CH_2—$, $—CH(CH_2CH_3)CH_2—$, $—CH(CH_2CH_3)CH_2CH_2—$, $—CH_2CH(CH_2CH_3)CH_2—$, $—CH(CH_2CH_2CH_3)CH_2—$, $—CH(CH_2CH_2CH_3)CH_2CH_2—$ and $—CH_2CH(CH_2CH_2CH_3)CH_2—$; longer branched carbon chains can also be used, if desired. In some aspects, a chain of one or more carbons (e.g., any of the above linear or branched chains) is further substituted with one or more hydroxyl groups. Examples of hydroxy- or dihydroxy (diol)-substituted chains include $—CH(OH)—$, $—CH(OH)CH_2—$, $—C(OH)_2CH_2—$, $—CH_2CH(OH)CH_2—$, $—CH(OH)CH_2CH_2—$, $—CH(OH)CH(OH)CH_2—$, $—CH_2CH_2CH(OH)CH_2—$, $—CH_2CH(OH)CH_2CH_2—$, $—CH(OH)CH_2CH_2CH_2—$, $—CH_2CH(OH)CH(OH)CH_2—$, $—CH(OH)CH(OH)CH_2CH_2—$ and $—CH(OH)CH_2CH(OH)CH_2—$. In each of the foregoing examples, the first carbon atom of the chain is ether-linked to a glucose monomer of the alpha-glucan, and the last carbon atom of the chain is linked to a positively charged group (e.g., a substituted ammonium group as disclosed herein). One or more positively charged organic groups in some aspects can comprise trimethylammonium hydroxypropyl groups (Structure 11, when each of $R_2$, $R_3$ and $R_4$ is a methyl group).

In aspects in which a carbon chain of a positively charged organic group has a substitution in addition to a substitution with a positively charged group, such additional substitution can be with one or more hydroxyl groups, oxygen atoms (thereby forming an aldehyde or ketone group), alkyl groups (e.g., methyl, ethyl, propyl, butyl), and/or additional positively charged groups, for example. A positively charged group is typically bonded to the terminal carbon atom of the carbon chain. A positively charged group can also comprise imidazoline ring-containing compounds in some aspects.

A counter ion for a positively charged organic group herein can be any suitable anion, such as an acetate, borate, bromate, bromide, carbonate, chlorate, chloride, chlorite, dihydrogen phosphate, fluoride, hydrogen carbonate, hydrogen phosphate, hydrogen sulfate, hydrogen sulfide, hydrogen sulfite, hydroxide, hypochlorite, iodate, iodide, nitrate, nitride, nitrite, oxalate, oxide, perchlorate, permanganate, phosphate, phosphide, phosphite, silicate, stannate, stannite, sulfate, sulfide, sulfite, tartrate, or thiocyanate anion.

An organic group that is in ether-linkage to an alpha-glucan herein can be a negatively charged (anionic) group, for example. A anionic group can be, for example, any of those disclosed in U.S. Pat. Appl. Publ. Nos. 2016/0311935 or 2020/0002646, or Int. Pat. Appl. Publ. No. WO2021/252569, which are incorporated herein by reference. An anionic group herein can comprise a substituted alkyl group, where the alkyl group has one, two, or more substitutions with at least one anionic group. A substituted alkyl group can be a substituted methyl, ethyl, propyl, butyl, pentyl, hexyl, heptyl, octyl, nonyl, decyl, undecyl, dodecyl, tridecanyl, tetradecanyl, pentadecanyl, hexadecanyl, heptadecanyl, or octadecanyl group. An anionic group of a substituted alkyl group can be a carboxy group, for example; i.e., an anionic group herein can comprise a carboxy alkyl group. Examples of suitable carboxy alkyl groups herein include carboxymethyl ($—CH_2COOH$), carboxyethyl (e.g., $—CH_2CH_2OOOH$, $—CH(COOH)CH_3$), carboxypropyl (e.g., $—CH_2CH_2CH_2OOOH$, $—CH_2CH(COOH)CH_3$, $—CH(COOH)CH_2CH_3$), carboxybutyl and carboxypentyl groups. Aside from being substituted with at least one anionic group, a substituted alkyl group can optionally be further substituted with at least one other group such as an alkyl group or hydroxyl group.

A soluble alpha-glucan ether in some aspects can contain one type of etherified organic group. Examples of such ether compounds contain a carboxy alkyl group (e.g., carboxymethyl) as the only etherified organic group. Yet, in some aspects, a soluble alpha-glucan ether can contain two or more different types of etherified organic groups (i.e., mixed ether of the alpha-glucan). Examples of such alpha-glucan ethers contain (i) an alkyl group and a carboxy alkyl group as etherified organic groups (alkyl carboxyalkyl alpha-glucan), (ii) a hydroxy alkyl group and a carboxy alkyl group as etherified organic groups (hydroxyalkyl carboxyalkyl alpha-glucan), (iii) two different carboxy alkyl groups as etherified organic groups, and (iv) a carboxy alkyl group and an aryl (e.g., benzyl) group. Non-limiting examples of some of these types of mixed ethers include carboxymethyl hydroxyethyl alpha-glucan, carboxymethyl hydroxypropyl alpha-glucan, and carboxymethyl benzyl alpha-glucan. In some aspects, a mixed alpha-glucan contains a carboxyl alkyl group (e.g., carboxymethyl) and another group as disclosed in U.S. Patent Appl. Publ. No. 2020/0002646, which is incorporated herein by reference.

A soluble alpha-glucan derivative is an ester, carbamate, sulfonyl, or sulfonate derivative in some aspects. For example, a soluble alpha-glucan derivative can comprise one or more charged organic groups (e.g., cationic or anionic) in ester, carbamate, or sulfonyl linkage to the alpha-glucan. Acyl groups of a soluble alpha-glucan derivative herein can be as disclosed, for example, in U.S. Patent Appl. Publ. Nos. 2014/0187767, 2018/0155455, or 2020/0308371, U.S. Appl. No. 63/037,184, or Int. Pat. Appl. Publ. No. WO2021252575, which are each incorporated herein by reference. Carbamate groups of a soluble alpha-glucan derivative herein can be as disclosed, for example, in Int. Pat. Appl. Publ. No. WO2020/131711, U.S. Appl. No. 63/037,076, or Int. Pat. Appl. Publ. No. WO2021/252569, which are each incorporated herein by reference.

A soluble alpha-glucan derivative in some aspects can be negatively charged by virtue of having carboxylate (carboxylic acid) groups. A carboxylic acid group can exist by itself (e.g., carbon 6 of glucose can be $—COOH$), or via an organic group that is (i) ether-, ester-, carbamate, or sulfonyl-linked to an alpha-glucan and (ii) comprises a carboxylic acid group (e.g., a carboxy alkyl group such as carboxymethyl), for example. In some aspects, a carboxylic group can be introduced (e.g., at carbon 6 of glucose and/or at a carbon of a substituent group) by oxidizing alpha-glucan or an alpha-glucan derivative; oxidation can be performed via a process as disclosed, for example, in Canadian Patent Publ.

Nos. 2028284 or 2038640, or U.S. Pat. Nos. 4,985,553, 2,894,945, 5,747,658, or 7595392, or U.S. Pat. Appl. Publ. Nos. 2015/0259439, 2018/0022834, or 2018/0079832, all of which are incorporated herein by reference.

A composition as presently disclosed comprising insoluble alpha-glucan and a soluble alpha-glucan derivative can be in the form of particles (typically insoluble particles) comprising these components, for example. As comprised in an aqueous composition such as a dispersion, about 40-60%, 40-55%, 45-60%, 45-55%, 47-53%, 48-52%, 49-51%, or 50% by weight of such particles have a diameter (i.e., $D_{50}$) of about, less than about, or at least about, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 1-50, 1-40, 1-30, 1-25, 1-22, 1-20, 1-18, 5-40, 5-30, 5-25, 5-22, 5-20, 5-18, 15-22, 15-20, 15-18, 16-22, 16-20, or 16-18 microns, for example.

A composition herein can comprise about 0.1 to about 200 wt % of one or more soluble alpha-glucan derivatives, wherein this wt % is based on the weight of the one or more insoluble alpha-glucans in the composition. In some aspects, a composition comprises about 0.1, 1, 2, 3, 4, 5, 6, 7, 8, 9, 10, 11, 12, 13, 14, 15, 16, 17, 18, 19, 20, 25, 30, 35, 40, 45, 50, 75, 100, 125, 150, 175, 200, 1-200, 1-175, 1-150, 1-125, 25-200, 25-175, 25-150, 25-125, 50-200, 50-175, 50-150, 50-125, 75-200, 75-175, 75-150, 75-125, 100-200, 100-175, 100-150, 100-125, 0.1-50, 1-30, 1-25, 1-20, 1-15, 1-10, 3-30, 3-25, 3-20, 3-15, 3-10, 10-30, 10-25, 10-20, or 10-15 wt % of one or more soluble alpha-glucan derivatives, wherein this wt % is based on the weight of the one or more insoluble alpha-glucans in the composition.

Particles herein can comprise insoluble alpha-glucan that is coated by one or more soluble alpha-glucan derivatives. Thus, particles can optionally be characterized to have a core comprising insoluble alpha-glucan and an outer coat (shell, outer layer) of soluble alpha-glucan derivative(s). The outer coat typically is continuous, covering (encapsulating) the entirety of the insoluble alpha-glucan component(s), but in some aspects coats at least about 50%, 60%, 70%, 80%, 90%, 95%, 96%, 97%, 98%, 99%, or 99.5% of the insoluble alpha-glucan component(s). The average core diameter of the particles can be as described herein for particles of insoluble alpha-glucan, for example. The thickness of the outer coat in some aspects can be one, two, three, four, five, or six molecules of soluble alpha-glucan derivative(s) thick. Yet, in some aspects, the thickness of the outer coat can be about, less than about, or at least about, 0.005, 0.01, 0.05, 0.1, 0.2, 0.3, 0.4, 0.5, 1, 5, 10, 25, or 50 microns. Particles herein can optionally be characterized to comprise insoluble alpha-glucan that has been "surface-exchanged" or "surface-modified" with one or more soluble alpha-glucan derivatives. The outer coat of soluble alpha-glucan derivative(s) is not chemically/covalently bonded to the insoluble alpha-glucan core.

Particles can have a positive surface charge or negative surface charge in some aspects. Typically, such a surface charge is due to the charge (or average charge) of the one or more soluble alpha-glucan derivatives coating the insoluble alpha-glucan core. The zeta-potential of such particles in an aqueous composition (e.g., dispersion) in some aspects can be about, or over about, ±30 mV, ±35 mV, ±37.5 mV, ±40 mV, ±42.5 mV, ±45 mV, or ±50 mV. Simply for illustration purposes, it should be understood that a zeta potential over ±30 mV, for example, excludes zeta potentials ranging from −30 mV to +30 mV. In some aspects, the zeta potential is ±30 to ±50 mV, ±30 to ±45 mV, ±30 to ±40 mV, ±35 to ±50 mV, ±35 to ±45 mV, or ±35 to ±40 mV. In general, it is contemplated that the zeta potential of particles herein comprising an anionic soluble alpha-glucan derivative shell has a greater negative value than −30 mV, and that the zeta potential of particles comprising a cationic soluble alpha-glucan derivative shell has a greater positive value than +30 mV. The foregoing zeta potential values can in some aspects be associated with aqueous compositions having a pH of about 6-8, 5-9, or 4-9.

Some aspects of the present disclosure concern a method of producing a composition herein comprising insoluble alpha-glucan and a soluble alpha-glucan derivative. Such a method can comprise: (a) blending/mixing together at least water, insoluble alpha-glucan, and at least one soluble alpha-glucan derivative (in a suitable container) to provide a blended product, and (b) optionally drying the blended/mixed product. Such a method can optionally be characterized as a method or process of surface-exchanging insoluble alpha-glucan with at least one soluble alpha-glucan derivative.

Insoluble alpha-glucan of a surface-exchange method herein can be as disclosed elsewhere herein, for example. Thus, insoluble alpha-glucan can be in the form of, and/or have one or more features of (e.g., glycosidic linkage profile, molecular weight, and/or production method), insoluble alpha-glucan as comprised in a composition herein comprising insoluble alpha-glucan and a soluble alpha-glucan derivative. A soluble alpha-glucan derivative of a surface-exchange method herein can be as disclosed elsewhere herein, for example. Thus, a soluble alpha-glucan derivative can be in the form of, and/or have one or more features of (e.g., glycosidic linkage profile, molecular weight, derivatization profile [e.g., substituent(s), DoS]), a soluble alpha-glucan derivative as comprised in a composition herein comprising insoluble alpha-glucan and a soluble alpha-glucan derivative.

In some aspects, blending step (a) of a surface-exchange method herein can be performed by blending (i) a dry powder of the soluble alpha-glucan derivative (e.g., having s 12, 11, 10, 9, 8, 7, 6, 5, 4, 3, 2, 1, 0.5, or 0.1 wt/o water) ("component i") and (ii) a composition comprising about 10 to 80 wt % (or 5 to 80 wt %) of the insoluble alpha-glucan and a balance of water or aqueous solution up to 100 wt % ("component ii"). The composition of (ii) can comprise about 5, 7.5, 10, 15, 20, 25, 30, 35, 40, 45, 50, 55, 60, 65, 70, 75, 80, 10-50, 10-45, 10-40, 20-50, 20-45, 20-40 or 5-15 wt % of the insoluble glucan, for example, where the balance is of water or aqueous solution up to 100 wt %. The composition of (ii) can optionally be characterized as a wet cake, and/or its insoluble alpha-glucan may have never been dried ("never-dried") since its enzymatic synthesis with glucansucrase. However, in some aspects, the insoluble alpha-glucan of the composition of (ii) may have been dried at least once since its synthesis. The resulting blend can comprise, for example, about 10, 15, 20, 25, 30, 40, 50, 60, 70, 80, 10-80, 10-70, 10-60, 20-80, 20-70, 20-60, 30-80, 30-70, or 30-60 wt % solids. Such a blending strategy can optionally be characterized as a "solid state" blending method.

In some aspects, blending step (a) of a surface-exchange method herein can be performed by blending (i) a dry powder of said soluble alpha-glucan derivative (e.g., having ≥10, 9, 8, 7, 6, 5, 4, 3, 2, 1, 0.5, or 0.1 wt % water), (ii) a composition comprising about 10 to 80 wt % (or 5 to 80 wt %) of said insoluble alpha-glucan and a balance of water or aqueous solution up to 100 wt %, and (iii) water or aqueous solution ("component iii"), wherein the total solids of the blended product is about 1 to 30 wt %. The composition of (ii) can optionally be characterized as a wet cake, and/or be never-dried. However, in some aspects, the insoluble alpha-glucan of the composition of (ii) may have been dried at least once since its synthesis. The resulting blend can comprise, for example, about 1, 2, 5, 10, 15, 20, 25, 30, 1-30, 1-25, 1-20, 1-15, 2-30, 2-25, 2-20, 2-15, 5-30, 5-25, 5-20, or 5-15 wt % solids. Such a blending strategy can optionally be characterized as a dispersion blending method.

Blending of components i and ii, or i, ii and iii, in step (a) of a surface-exchange method herein can entail one or more of stirring, shaking, vortexing, agitation, blending, paddling, rotating, sonication, comminuting, and/or shearing, for example. In some aspects, blending can be performed by, or further include, using a sonicator (e.g., ultrasonicator) (e.g., 40-60 W, ~50 W), homomixer, high shear mixer or homogenizer (e.g., rotary or piston, rotor-stator [in-line rotor-stator], Waring® blender), planetary mixer, colloid mill, jet mill, vortex, and/or any other suitable methodology. Yet, in some aspects, blending can be performed by simple means only such as shaking or stirring, or otherwise by comminuting the components (i and ii, or i, ii and iii above) into a mixture without the aid of a high energy homogenizer or equivalent device. Blending in some aspects can comprise using at least one device that mixes/blends/stirs/agitates solid/solid-like/non-liquid materials (e.g., components i and ii above) such as an extruder (e.g., paddle extruder; screw extruder such as a single screw or twin screw extruder; co-rotating or counter-rotating extruder), injection molder, compounder, or kneader. Blending of components i, ii and iii in some aspects can be done until such time that a feature (e.g., zeta potential, viscosity, particle size [e.g., $D_{50}$]) is observed/measured that is different from what would be observed/measured if components ii and iii are blended without component i. Blending can be conducted at room temperature or at about, at least about, or no more than about, 15, 20, 25, 30, 35, 40, 45, 50, 55, 60, 65, 70, 15-70, 15-60, 15-50, 15-40, 15-30, 15-25, 20-70, 20-60, 20-50, 20-40, 20-30, or 20-25° C., for example. In some aspects, the number of times a sample being blended (e.g., components i and ii, or i, ii and iii) is circulated/passed in its entirety (or at least about 95% or 98% of its entirety) through a blending device herein ("passes") can be 1, 2, 3, 4, 5, 6, 7, 8, 9, 10, 15, 20, 1-4, 1-3, 2-4, 2-3, 1-5, 1-10, 1-20, or more times, for example. Blending in some aspects can be as described in the below Examples, but with components i and ii (or i, ii and iii) as generally described here. Blending herein can optionally further include addition of an additive as disclosed elsewhere herein (an additive that is different from a soluble alpha-glucan derivative as disclosed).

Following a solid state blending process (above), a blend can optionally be dispersed (e.g., to a solids wt/o in water/aqueous solution as disclosed herein) and/or dried. However, in some aspects, a solid state blend can be used as it exists following its preparation (i.e., no dispersion and/or drying). Following a dispersion blending process (above), a blend can optionally be dried, or it can be used as a dispersion as it exists following its preparation (i.e., no drying).

A surface-exchange method herein can optionally comprise a step (b) of drying the blended product resulting from step (a) (or the product of step [a] that has then been dispersed). Drying can be done using an oven, freeze drying, spray drying, distillation, and/or by agitated air drying (e.g., agitated filter/film drying such as that under vacuum, fluidized bed drying, rotary drying such as drum drying, rotary evaporation). Drying in some aspects can be at a temperature of about, or at least about, 20, 25, 30, 40, 50, 60, 70, 80, 90, 100, 110, 120, 130, 140, 20-140, 20-130, 30-50, 35-45, 90-110, or 95-105° C., for example. In some aspects, a dried product can be ground up, or otherwise comminuted, into powder or other particulate form (e.g., as disclosed herein) after being dried. Optionally, a solid state blend herein can be broken down to particles before being dried, such as described in U.S. Patent Appl. Publ. No. 2019/0112456, which is incorporated herein by reference.

In some aspects, insoluble alpha-glucan that is blended with a soluble alpha-glucan derivative exhibits a viscosity when in an aqueous dispersion that is reduced as compared to the same insoluble alpha-glucan but which has not been blended with the soluble alpha-glucan derivative. Such a reduction in viscosity can be by about, or at least about, 10%, 20%, 30%, 40%, 50%, 60%, 70%, 80%, or 90%, for example. Yet, in some aspects, such as with insoluble alpha-glucan having a crystallinity index over ~0.65 and/or a particle size over ~200 microns ($D_{50}$) as dispersed, insoluble alpha-glucan that is blended with a soluble alpha-glucan derivative exhibits a viscosity when in an aqueous dispersion that is increased as compared to the same insoluble alpha-glucan but which has not been blended with the soluble alpha-glucan derivative. Such an increase in viscosity can be by about, or at least about, 50%, 100%, 500%, 1000%, 2500%, 5000%, or 6000%, for example.

In some aspects, blending insoluble alpha-glucan with a soluble charged alpha-glucan derivative herein prevents or reduces the micro-structural effects typically observed (e.g., irreversible agglomeration, which increases particle size) when insoluble alpha-glucan is dried and then dispersed to an aqueous dispersion. For example, insoluble alpha-glucan that has been blended with a soluble charged alpha-glucan derivative, dried, and then dispersed to an aqueous dispersion can exhibit a particle size (e.g., $D_{90}$) that is about the same as, or is no more than 5%, 10%, or 20% larger than, the particle size (e.g., $D_{90}$) of the same blended material but which has not been dried.

A composition herein comprising insoluble alpha-glucan and at least one soluble alpha-glucan derivative can be as produced by a method herein for producing such a composition, for example.

Some aspects of the present disclosure concern a composition comprising insoluble alpha-glucan that is coated by at least one additive, wherein at least about 50% of the glycosidic linkages of the insoluble alpha-glucan are alpha-1,3 glycosidic linkages, and the weight-average degree of polymerization (DPw) of the insoluble alpha-glucan is at least 15 (or at least 10). An additive in such compositions can optionally be referred to as a second ingredient, second component, phase modifier, or phase-modifying additive, for example. An additive in typical aspects does not chemically react with insoluble alpha-glucan and so does not chemically modify or derivatize the insoluble alpha-glucan in any way that results in a compound that is different from the insoluble alpha-glucan (e.g., such an additive does not serve to substitute any hydrogens of glucose monomeric unit hydroxyl groups of the insoluble alpha-glucan; such an additive does not change the molecular formula of the insoluble alpha-glucan). A composition comprising insoluble alpha-glucan coated by at least one additive can be as produced by a method herein for producing such a composition, for example. There can be one, two, three, four, or more additives in some aspects. An additive can be aqueous-soluble or aqueous-insoluble. Yet, in some other aspects, insoluble alpha-glucan herein can be coated by one or more additive(s) by virtue of the insoluble alpha-glucan being comprised in a composition that also comprises the additive(s).

Insoluble alpha-glucan of a composition herein comprising insoluble alpha-glucan coated by at least one additive can be as disclosed elsewhere herein, for example. Thus, it can be in the form of, and/or have one or more features of (e.g., glycosidic linkage profile, molecular weight, and/or production method), insoluble alpha-glucan as comprised in a composition herein comprising insoluble alpha-glucan and a soluble alpha-glucan derivative.

A composition as presently disclosed comprising insoluble alpha-glucan and an additive can be, for example, in the form of particles (typically insoluble particles) comprising these components. Such a composition can comprise particles of the insoluble alpha-glucan coated by the additive, for example. As comprised in an aqueous composition such as a dispersion, about 40-60%, 40-55%, 45-60%, 45-55%, 47-53%, 48-52%, 49-51%, or 50% by weight of such particles have a diameter (i.e., $D_{50}$) of about, less than about, or at least about, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 1-50, 1-40, 1-30, 1-25, 1-22, 1-20, 1-18, 5-40, 5-30, 5-25, 5-22, 5-20, 5-18, 15-22, 15-20, 15-18, 16-22, 16-20, or 16-18 microns, for example.

A composition as presently disclosed comprising insoluble alpha-glucan and an additive can comprise about 0.1 to about 200 wt % of one or more additives, wherein this wt % is based on the weight of the one or more insoluble alpha-glucans in the composition. In some aspects, a composition comprises about 0.1, 1, 2, 3, 4, 5, 6, 7, 8, 9, 10, 11, 12, 13, 14, 15, 16, 17, 18, 19, 20, 25, 30, 35, 40, 45, 50, 75, 100, 125, 150, 175, 200, 250, 300, 350, 400, 450, 500, 550, 600, 650, 700, 750, 800, 850, 900, 1-200, 1-175, 1-150, 1-125, 25-200, 25-175, 25-150, 25-125, 50-200, 50-175, 50-150, 50-125, 75-200, 75-175, 75-150, 75-125, 100-200, 100-175, 100-150, 100-125, 0.1-50, 1-30, 1-25, 1-20, 1-15, 1-10, 3-30, 3-25, 3-20, 3-15, 3-10, 10-30, 10-25, 10-20, 10-15, 400-800, 400-750, 400-700, 400-650, 400-600, 400-550, 450-800, 450-750, 450-700, 450-650, 450-600, 450-550, 500-800, 500-750, 500-700, 500-650, 500-600, or 500-550 wt % of one or more additives, wherein this wt % is based on the weight of the one or more insoluble alpha-glucans in the composition.

Particles herein can comprise insoluble alpha-glucan that is coated by one or more additives. Thus, particles can optionally be characterized to have a core comprising insoluble alpha-glucan and an outer coat (shell, outer layer) comprising one or more additives. The outer coat typically is continuous, covering (encapsulating) the entirety of the insoluble alpha-glucan component(s), but in some aspects coats at least about 50%, 60%, 70%, 80%, 90%, 95%, 96%, 97%, 98%, 99%, or 99.5% of the insoluble alpha-glucan component(s). The average core diameter of the particles can be as described herein for particles of insoluble alpha-glucan, for example. The thickness of the outer coat in some aspects can be one, two, three, four, five, or six molecules of additive(s) thick. Yet, in some aspects, the thickness of the outer coat can be about, less than about, or at least about, 0.005, 0.01, 0.05, 0.1, 0.2, 0.3, 0.4, 0.5, 1, 5, 10, 25, or 50 microns. Particles herein can optionally be characterized to comprise insoluble alpha-glucan that has been "surface-exchanged" or "surface-modified" with one or more additives. The outer coat of soluble alpha-glucan derivative(s) is not chemically/covalently bonded to the insoluble alpha-glucan core.

Particles herein of insoluble alpha-glucan coated by one or more additives can have a positive surface charge or negative surface charge in some aspects. Typically, such a surface charge is due to the charge (or average charge) of the one or more additives coating the insoluble alpha-glucan core. The zeta-potential of such particles in an aqueous composition (e.g., dispersion) in some aspects can be about, or over about, ±5 mV, ±10 mV, ±15 mV, ±20 mV, ±25 mV, ±30 mV, ±35 mV, ±40 mV, ±45 mV, or ±50 mV. Simply for illustration purposes, it should be understood that a zeta potential over ±5 mV, for example, excludes zeta potentials ranging from −5 mV to +5 mV. The foregoing zeta potential values can in some aspects be associated with aqueous compositions having a pH of about 6-8, 5-9, or 4-9.

An additive of a composition herein comprising insoluble alpha-glucan and an additive can be any compound of the present disclosure that is not an insoluble alpha-glucan having at least 50% alpha-1,3 glycosidic linkages. While water can optionally be present in such a composition, there must be at least one additive present that is not water. In some aspects, an additive comprises or consists of a non-aqueous liquid and/or a hydrophobic or non-polar liquid or composition. A non-aqueous liquid can be polar or non-polar (apolar), for example. An additive in some aspects can comprise or consist of a solid material; such an additive can optionally be in an aqueous liquid or non-aqueous liquid. An additive can have neutral, negative (anionic), or positive (cationic) charge, for example. An additive can be any ingredient/component disclosed herein of a personal care product, pharmaceutical product, household care product, industrial product, ingestible product, film/coating, composite, latex/dispersion/emulsion, encapsulant, detergent composition (e.g., fabric care, dish care), oral care, or builder composition, for example. Merely as examples, an additive herein can be an oil such as mineral oil, silicone oil (e.g., dimethicone/polydimethylsiloxane, hexamethyldisiloxane), paraffin oil, or plant/vegetable oil (e.g., linseed oil, soybean oil, palm oil, coconut oil, canola oil, corn oil, sunflower oil, grape seed oil, cocoa butter, olive oil, rice bran oil, rapeseed oil, peanut oil, sesame oil, cottonseed oil, palm kernel oil); shortening (e.g., vegetable shortening); lipid; fat (e.g., lard, tallow, animal fat); glyceride (e.g., tri-, di- and/or mono-glyceride; e.g., caprylic/capric triglyceride); glycerol (or other polyol such as low molecular weight polyol); fatty acid; fatty aldehyde, fatty alcohol, fatty acid ester (e.g., sorbitan oleate); fatty acid amide; wax (e.g., paraffin wax, caranuba wax); phospholipid; sterol; alkane; alkene/olefin; petrolatum (i.e., petroleum jelly); grease; anionic detergent (e.g., lauryl sulfate, alkylbenzene sulfonate); cationic detergent; non-ionic or zwitterionic detergent (e.g., polyoxyethylene-based detergent such as Tween or Triton [ethoxylates], glycoside-based detergents such as octyl thioglucoside maltoside, CHAPS); or any epoxidized versions of these; or any similar compound such as disclosed in U.S. Patent Appl. Publ. Nos. 2009/0093543 (e.g., Table 2 therein) or 2019/0144897, which are incorporated herein by reference. Merely as examples, an additive herein can be a sugar alcohol (e.g., mannitol, sorbitol, xylitol, lactitol, isomalt, maltitol, hydrogenated starch hydrolysate), polymeric polyol (e.g., polyether polyol, polyester polyol, polyethylene glycol, polyvinyl alcohol), aprotic solvent (e.g., a polar aprotic solvent such as acetone or propylene carbonate), protic solvent (e.g., isopropanol, ethanol, methanol), hardener (e.g., active halogen compound, vinylsulfone, epoxy), resin (typically uncured) (e.g., synthetic resin such as epoxy or acetal resin; natural resin such as plant resin [e.g., pine resin], insect resin [e.g., shellac], or bitumen), or propanediol (1,3-propanediol). Merely as examples, an additive herein can be a fragrance/scent (e.g., hydrophobic aroma compound, or any as disclosed in U.S. Pat. No. 7,196,049, which is incorporated herein by reference), ingestible product, food, beverage, flavor (e.g., any as disclosed in U.S. Pat. No. 7,022,352, which is incorporated herein by reference), or hydrophobic flavorant or nutrient, or dye (e.g., oil-soluble dye such as Sudan red). Merely as examples, an additive herein can be polyurethane, polyvinyl acetate, poly acrylate (i.e., acrylic), poly lactic acid, polyvinylamine, polycarboxylate, a polysaccharide (e.g., glucan such as cellulose, starch, beta-1,3-glucan; fructan; xylan; arabinan; mannan; galactan) other than an insoluble alpha-glucan having at least 50% alpha-1,3 glycosidic linkages, gelatin, melamine, inorganic filler material (e.g., carbon black, a silicate such as sodium silicate, talk, chalk, a clay such as bentonite clay, or a carbonate such as calcium carbonate, calcium-magnesium carbonate, sodium percarbonate, sodium carbonate, sodium bicarbonate, ammonium bicarbonate, barium carbonate, magnesium carbonate, potassium carbonate, or iron[II] carbonate), penetrant (e.g., 1,2-propanediol, triethyleneglycol butyl ether, 2-pyrrolidone), biocide (e.g., metaborate, thiocyanate, sodium benzoate, benzisothiazolin-3-one), yellowing inhibitor (e.g., sodium hydroxymethyl sulfonate, sodium p-toluenesulfonate), ultraviolet absorbers (e.g., benzotriazole compound), antioxidant (e.g., sterically hindered phenol compound), water-resistance agent (e.g., ketone resin, anionic latex, glyoxal), or binder (e.g., polyvinyl alcohol, polyvinyl acetate, partially saponified polyvinyl acetate, silanol-modified polyvinyl alcohol, polyurethane, starch, corn dextrin, carboxymethyl cellulose, cellulose ether, hydroxyethyl cellulose, hydroxypropyl cellulose, ethylhydroxyethyl cellulose, methyl cellulose, alginate, sodium alginate, xanthan, carrageenan, casein, soy protein, guar gum, styrene butadiene latex, styrene acrylate latex). Merely as examples, an additive herein can be a bleaching agent (e.g., chlorine-based bleach such as sodium hypochlorite or chlorinated lime; peroxide-based bleach such as hydrogen peroxide, sodium percarbonate, peracetic acid, benzoyl peroxide, or potassium permanganate). Yet, in some aspects, an additive herein can be characterized/categorized as follows: amphiphilic material (e.g., surfactants such as lauryl sulfate; polymeric surfactants such as polyethylene glycol or polyvinyl alcohol; particles such as silica), physically adsorbed aqueous-insoluble small molecules (e.g., mineral oil; silicone oil; natural oil such as linseed, soybean, palm, or coconut oil), physically adsorbed aqueous-insoluble polymeric molecules (e.g., polyacrylate, polyvinylacetate, poly lactic acid), physically adsorbed aqueous-miscible small molecules (e.g., protic solvents such as isopropanol, ethanol, or methanol; polar aprotic solvents such as acetone or propylene carbonate; low molecular weight polyols such as glycerol; sugar alcohols), physically adsorbed water-miscible polymeric molecules (e.g., a polyol), chemically adsorbed/reacted material (e.g., alkyl ketene dimer; an alkenyl succinic anhydride such as octenyl succinic anhydride; epoxy compounds such as epoxidized linseed oil or a di-epoxy). In some aspects, an additive can be an alkyl ketene dimer (AKD), alkenyl succinic anhydride (e.g., octenyl succinic anhydride), epoxy compound (e.g., epoxidized linseed oil or a di-epoxy), phenethyl alcohol, undecyl alcohol, or tocopherol. An additive in some aspects can be a rubber or any other diene-based elastomer. Examples of rubber herein include natural rubber (NR) (e.g., NR latex) and synthetic rubber. Examples of synthetic rubber herein include synthetic polyisoprene, polybutadiene, styrene-butadiene copolymer, styrene-isoprene copolymer, butadiene-isoprene copolymer, styrene-butadiene-isoprene terpolymer, ethylene propylene diene monomer rubber, hydrogenated nitrile butadiene rubber, silicone rubber, and neoprene, which are also examples of diene-based elastomers. Rubber is not diene-based in some aspects, such as silicone rubber. In some aspects, an additive comprises an oil or any other hydrophobic solvent herein in which a hydrophobic substance (e.g., any as disclosed herein such as a hydrophobic fragrance, flavor, nutrient, or dye) has been dissolved. An additive herein typically is not only a salt (salt ion) or buffer such as $Na^+$, $Cl^-$, NaCl, phosphate, tris, or any other salt/buffer such as disclosed in U.S. Patent Appl. Publ. Nos. 2014/179913, 2016/0304629, 2016/0311935, 2015/0239995, 2018/0230241, or 2018/0237816, which are incorporated herein by reference. An additive can be any as disclosed in U.S. Patent Appl. Publ. No. 2019/0153674 (incorporated herein by reference), for example.

An additive is hydrophobic in some aspects (e.g., any of the above that are hydrophobic/apolar/non-polar). A hydrophobic additive is a liquid (e.g., at a temperature disclosed herein, e.g., 10-60, 15-60, 20-60, 25-60, 30-60, 10-55, 15-55, 20-55, 25-55, 30-55, 10-50, 15-50, 20-50, 25-50, 30-50, 10-45, 15-45, 20-45, 25-45, 30-45, 10-40, 15-40, 20-40, 25-40, or 30-40° C.) and not miscible in an aqueous composition (i.e., aqueous-insoluble) (e.g., in caustic or non-caustic aqueous conditions herein), for example. A liquid hydrophobic additive can be oil, for example, such as an oil disclosed herein. In some aspects, a hydrophobic additive is a solid (e.g., at a temperature disclosed herein) and not dissolvable in an aqueous composition (e.g., caustic or non-caustic aqueous conditions herein). A solid hydrophobic additive can be wax or grease, for example. In some aspects, a solid hydrophobic additive has a melting point of about, or at least about, 45, 46, 48, 50, 52, 54, 56, 58, 60, 62, 64, 66, 68, 70, 75, 80, 85, 90, 95, 100, 45-70, 45-65, 50-70, or 50-65° c.

If desired, any additive as disclosed herein can be included in a composition of the present disclosure comprising insoluble alpha-glucan and a soluble alpha-glucan derivative, and/or in a method of production thereof.

In some aspects, a composition comprising insoluble alpha-glucan that has been surface-exchanged with a soluble alpha-glucan derivative and/or additive herein does not comprise an antimicrobial agent, or comprises less than 0.001, 0.0005, or 0.0001 wt % of an antimicrobial agent. An antimicrobial agent can be comprised of one or more agents having antibacterial, antifungal, and/or antiprotozoal activity, for example.

Some aspects of the present disclosure concern a method of producing a composition comprising at least insoluble alpha-glucan and an additive. Such a method can comprise: (a) blending (i) an additive and (ii) a composition comprising about 10 to 80 wt % (or 5 to 80 wt %) of insoluble alpha-glucan and a balance of water or aqueous solution up to 100 wt %, thereby providing a blended product, optionally wherein the mass of the additive is within about 25% of the mass of the water or aqueous solution (optionally, the additive does not chemically react with insoluble alpha-glucan), and wherein at least about 50% of the glycosidic linkages of the insoluble alpha-glucan are alpha-1,3 glycosidic linkages, and the weight-average degree of polymerization (DPw) of the insoluble alpha-glucan is at least (or at least 10), and (b) drying the blended product, wherein most of (e.g., ≥90 wt %), or all of, the water that was present in the composition of (ii) is replaced with the additive. Such a method can optionally be characterized as a method or process of surface-exchanging insoluble alpha-glucan with at least one additive.

Insoluble alpha-glucan of a surface-exchange with additive method herein can be as disclosed elsewhere herein, for example. Thus, insoluble alpha-glucan can be in the form of, and/or have one or more features of (e.g., glycosidic linkage profile, molecular weight, and/or production method), insoluble alpha-glucan as comprised in a composition herein comprising insoluble alpha-glucan and a soluble alpha-glucan derivative. An additive of a surface-exchange with additive method herein can be as disclosed elsewhere herein, for example, such as for a composition comprising insoluble alpha-glucan that is coated by at least one additive.

In some aspects, blending step (a) of a surface-exchange with additive method herein can be performed by blending (i) an additive ("component i") and (ii) a composition comprising about 10 to 80 wt % (or 5 to 80 wt %) of the insoluble alpha-glucan and a balance of water or aqueous solution up to 100 wt % ("component ii"). The composition of (ii) can comprise about 5, 7.5, 10, 15, 20, 25, 30, 35, 40, 45, 50, 55, 60, 65, 70, 75, 80, 10-50, 10-45, 10-40, 20-50, 20-45, 20-40, or 5-15 wt % of the insoluble glucan, for example, where the balance is of water or aqueous solution up to 100 wt %. The composition of (ii) can optionally be characterized as a wet cake, and/or be never-dried. However, in some aspects, the insoluble alpha-glucan of the composition of (ii) may have been dried at least once since its synthesis. The resulting blend can comprise, for example, about 5, 10, 15, 20, 25, 30, 40, 50, 60, 70, 80, 10-80, 10-70, 10-60, 20-80, 20-70, 20-60, 30-80, 30-70, or 30-60 wt % solids. The mass of the additive in the blend can be the same as, or within about 1%, 2%, 3%, 4%, 5%, 10%, 15%, 20%, or 25% of, the mass of the water or aqueous solution in the blend in some aspects. An additive can be added in dry form, or as comprised in a liquid such as an aqueous liquid. Blending of components i and ii in a surface-exchange with additive method herein can be performed as described above for a surface-exchange method using soluble alpha-glucan derivative.

A surface-exchange with additive method herein comprises a step (b) of drying the blended product resulting from step (a). Such drying can be performed as described above for a surface-exchange method using soluble alpha-glucan derivative, for example.

In some aspects, such as those in which an additive is flowable at room temperature, water-miscible, and/or comprises a chain of two or more carbons (e.g., as disclosed herein such as glycerol, 1,3-propanediol, 1,2-propanediol, ethylene glycol, or propylene glycol, or a compound with a carbon chain having at least one, two, three or more substitutions [of hydrogen] with oxygen [e.g., hydroxyl]), a method herein of blending and drying produces a composition that is not flowable at room temperature. Such a composition can be in the form of (visually and/or haptically) an ointment, non-flowable lotion, or any other non-flowable material that has the consistency of an ointment, for example. However, in some aspects, a product can remain flowable, albeit less (e.g., ~25%, 50% or 75% less) flowable than the additive as it existed before performing the blending method.

A composition herein comprising insoluble alpha-glucan and at least one additive, such as a composition (e.g., particles) comprising insoluble alpha-glucan coated by at least one additive, can be as produced by a method herein for producing such a composition, for example.

A composition as presently disclosed—such as a composition comprising (i) insoluble alpha-glucan and soluble alpha-glucan derivative, or (ii) insoluble alpha-glucan and additive (e.g., particles of [i] or [ii])—can be an aqueous composition (e.g., dispersion such as colloidal dispersion) or a dry composition, for example. In some aspects, a composition herein can comprise about, at least about, or less than about, 0.01, 0.05, 0.1, 0.2, 0.25, 0.3, 0.4, 0.5, 0.6, 0.7, 0.75, 0.8, 0.9, 1.0, 1.2, 1.25, 1.4, 1.5, 1.6, 1.75, 1.8, 2.0, 2.25, 2.5, 3.0, 3.5, 4.0, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 99.5 wt % or w/v % of a composition of (i) and/or (ii) above. A composition can comprise a range between any two of these values of a composition of (i) and/or (ii) above (e.g., 5-50, 5-45, 5-40, 5-35, 5-30, 5-25, 5-20, 5-15, 5-10, or 10-20 wt %), for example. The liquid component of an aqueous composition can be an aqueous fluid such as water or aqueous solution, for instance. The solvent of an aqueous solution typically is water, or can comprise about, or at least about, 10, 20, 30, 40, 50, 60, 70, 80, 90, 95, 98, or 99 wt % water, for example. In some aspects, a composition herein can comprise, or be in the form of, a dispersion (e.g., emulsion), wet cake or wet powder (e.g., particles of average diameter/size of about 0.1-10, 0.1-5, 1-10, 1-5, 2-10, or 2-5 millimeters [mm] having 50%-90% by weight water and 10-50% by weight solids), dry powder, extrusion, composite, film/coating, or encapsulant. A composition herein most typically does not comprise (i) insoluble alpha-glucan and soluble alpha-glucan derivative, or (ii) insoluble alpha-glucan and additive, dissolved in a solution, which could occur, for example, under caustic conditions (e.g., pH≥11); also, a composition herein most typically is not a product of a process that employed such a solution.

An aqueous composition herein can have a viscosity of about, at least about, or less than about, 1, 5, 10, 100, 200, 300, 400, 500, 600, 700, 1000, 2000, 3000, 4000, 5000, 6000, 7000, 8000, 9000, 10000, 15000, 1-300, 10-300, 25-300, 50-300, 1-250, 10-250, 25-250, 50-250, 1-200, 10-200, 25-200, 50-200, 1-150, 10-150, 25-150, 50-150, 1-100, 10-100, 25-100, or 50-100 centipoise (cps), for example. Viscosity can be as measured with an aqueous composition herein at any temperature between about 3° C. to about 80° C., for example (e.g., 4-30° C., 15-30° C., 15-25° C.). Viscosity typically is as measured at atmospheric pressure (about 760 torr) or a pressure that is ±10% thereof. Viscosity can be measured using a viscometer or rheometer, for example, and can optionally be as measured at a shear rate (rotational shear rate) of about 0.1, 0.5, 1.0, 5, 10, 50, 100, 500, 1000, 0.1-500, 0.1-100, 1.0-500, 1.0-1000, or 1.0-100 $s^1$ (1/s), for example.

The aqueous solution component of an aqueous composition in some aspects has no (detectable) dissolved sugars, or about 0.1-1.5, 0.1-1.25, 0.1-1.0, 0.1-.75, 0.1-0.5, 0.2-0.6, 0.3-0.5, 0.2, 0.3, 0.4, 0.5, or 0.6 wt % dissolved sugars. Such dissolved sugars can include sucrose, fructose, leucrose, and/or soluble gluco-oligosaccharides, for example. The aqueous solution component of an aqueous composition in some aspects can have one or more salts/buffers (e.g., $Na^+$, $Cl^-$, NaCl, phosphate, tris, citrate) (e.g., s 0.1, 0.5, 1.0, 2.0, or 3.0 wt %), and/or a pH of about 4.0, 4.5, 5.0, 5.5, 6.0, 6.5, 7.0, 7.5, 8.0, 8.5, 9.0, 9.5, 10.0, 10.5, 4.0-10.0, 4.0-9.0, 4.0-8.0, 5.0-10.0, 5.0-9.0, 5.0-8.0, 6.0-10.0, 6.0-9.0, or 6.0-8.0, for example.

In some aspects, with an aqueous composition that is an aqueous dispersion (e.g., emulsion) of particles of the present disclosure (e.g., particles comprising [i] insoluble alpha-glucan and soluble alpha-glucan derivative, or [ii] insoluble alpha-glucan and additive), the particles are dispersed through about, or at least about, 30%, 40%, 50%, 60%, 70%, 80%, 85%, 90%, 95%, 98%, 99%, or 100% of the volume of the dispersion. In some aspects, such a level of dispersion (e.g., emulsion) is contemplated to be for a time (typically beginning from initial preparation of the dispersion) of about, at least about, or up to about, 0.5, 1, 2, 4, 6, 8, 10, 20, 30, 60, 90, 120, 150, 180, 210, 240, 270, 300, 330, or 360 days, or 1, 2, or 3 years.

The temperature of a composition herein can be about, or up to about, 0, 5, 10, 15, 20, 25, 30, 35, 40, 45, 50, 55, 60, 65, 70, 75, 80, 85, 90, 95, 100, 105, 110, 115, 120, 125, 130, 5-50, 20-25, 20-30, 20-40, 30-40, 40-130, 40-125, 40-120, 70-130, 70-125, 70-120, 80-130, 80-125, 80-120, 60-100, 60-90, 70-100, 70-90, 75-100, 75-90, or 75-85° C., for example.

A composition herein can, in some aspects, be non-aqueous (e.g., a dry composition). Examples of such embodiments include powders, granules, microcapsules, flakes, or any other form of particulate matter. Other examples include larger compositions such as pellets, bars, kernels, beads, tablets, sticks, or other agglomerates, or ointment or lotion (or any other form herein of a non-aqueous or dry composition). A non-aqueous or dry composition typically has about, or no more than about, 12, 10, 8, 6, 5, 4, 3, 2, 1.5, 1.0, 0.5, 0.25, 0.10, 0.05, or 0.01 wt % water comprised therein. In some aspects (e.g., those directed to laundry or dish washing detergents), a dry composition herein can be provided in a sachet or pouch.

A composition herein can, in some aspects, comprise one or more salts such as a sodium salt (e.g., NaCl, $Na_2SO_4$). Other non-limiting examples of salts include those having (i) an aluminum, ammonium, barium, calcium, chromium (II or III), copper (I or II), iron (II or III), hydrogen, lead (11), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in a composition, for example. A salt can be present in an aqueous composition herein at a wt % of about, or at least about, 0.01, 0.025, 0.05, 0.075, 0.1, 0.25, 0.5, 0.75, 1.0, 1.25, 1.5, 1.75, 2.0, 2.5, 3.0, 3.5, 0.01-3.5, 0.5-3.5, 0.5-2.5, or 0.5-1.5 wt % (such wt % values typically refer to the total concentration of one or more salts), for example.

A composition herein can optionally contain one or more enzymes (active enzymes). Examples of suitable enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, arabinofuranosidases, phytases, isomerases, transferases, nucleases, and amylases. If an enzyme(s) is included, it may be comprised in a composition herein at about 0.0001-0.1 wt % (e.g., 0.01-0.03 wt %) active enzyme (e.g., calculated as pure enzyme protein), for example. In fabric care or automatic dishwashing applications, an enzyme herein (e.g., any of the above such as cellulase, protease, amylase, and/or lipase) can be present in an aqueous composition in which a fabric or dish is treated (e.g., wash liquor, grey water) at a concentration that is minimally about 0.01-0.1 ppm total enzyme protein, or about 0.1-10 ppb total enzyme protein (e.g., less than 1 ppm), to maximally about 100, 200, 500, 1000, 2000, 3000, 4000, or 5000 ppm total enzyme protein, for example.

A composition of the present disclosure is biodegradable in some aspects. Such biodegradability can be, for example, as determined by the Carbon Dioxide Evolution Test Method (OECD Guideline 301B, incorporated herein by reference), to be about, at least about, or at most about, 5%, 10%, 15%, 20%, 25%, 30%, 35%, 40%, 45%, 50%, 55%, 60%, 65%, 70%, 75%, 80%, 85%, 90%, 5-60%, 5-80%, 5-90%, 40-70%, 50-70%, 60-70%, 40-75%, 50-75%, 60-75%, 70-75%, 40-80%, 50-80%, 60-80%, 70-80%, 40-85%, 50-85%, 60-85%, 70-85%, 40-90%, 50-90%, 60-90%, or 70-90%, or any value between 5% and 90%, after 15, 30, 45, 60, 75, or 90 days of testing. Biodegradability in some aspects can be with respect to an incumbent material such as a polyacrylate. It is contemplated that the biodegradability of a composition herein can be about, at least about, or at most about, 10%, 25%, 50%, 75%, 100%, 150%, 200%, 250%, 500%, 750%, or 1000% higher than the biodegradability of an incumbent material; such biodegradability can be as determined above, for example.

A composition as presently disclosed—such as a composition comprising (i) insoluble alpha-glucan and soluble alpha-glucan derivative, or (ii) insoluble alpha-glucan and additive (e.g., particles of [i] or [ii])—can be in the form of a household care product, personal care product, industrial product, ingestible product (e.g., food product), medical product, or pharmaceutical product, for example, such as described in any of U.S. Patent Appl. Publ. Nos. 2018/0022834, 2018/0237816, 2018/0230241, 20180079832, 2016/0311935, 2016/0304629, 2015/0232785, 2015/0368594, 2015/0368595, 2016/0122445, 2019/0202942, or 2019/0309096, or International Patent Appl. Publ. No. WO2016/133734, which are all incorporated herein by reference. In some aspects, a composition can comprise at least one component/ingredient of a household care product, personal care product, industrial product, pharmaceutical product, or ingestible product (e.g., food product) as disclosed in any of the foregoing publications and/or as presently disclosed.

A composition in some aspects is believed to be useful for providing one or more of the following physical properties to a personal care product, pharmaceutical product, household product, industrial product, or ingestible product (e.g., food product): thickening, freeze/thaw stability, lubricity, moisture retention and release, texture, consistency, shape retention, emulsification, binding, suspension, dispersion, gelation, reduced mineral hardness, for example.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient, if desired. An active ingredient is generally recognized as an ingredient that causes an intended pharmacological effect.

In some aspects, a skin care product can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil. A skin care product can be an ointment, lotion, or sanitizer (e.g., hand sanitizer) in some aspects.

A personal care product herein can also be in the form of makeup, lipstick, mascara, rouge, foundation, blush, eyeliner, lip liner, lip gloss, other cosmetics, sunscreen, sun block, nail polish, nail conditioner, bath gel, shower gel, body wash, face wash, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, after-shaving product, cleanser, skin gel, rinse, dentifrice composition, toothpaste, or mouthwash, for example. An example of a personal care product (e.g., a cleanser, soap, scrub, cosmetic) comprises a carrier or exfoliation agent (e.g., jojoba beads [jojoba ester beads]) (e.g., about 1-10, 3-7, 4-6, or 5 wt %); such an agent may optionally be dispersed within the product.

A personal care product in some aspects can be a hair care product. Examples of hair care products herein include shampoo, hair conditioner (leave-in or rinse-out), cream rinse, hair dye, hair coloring product, hair shine product, hair serum, hair anti-frizz product, hair split-end repair product, mousse, hair spray, and styling gel. A hair care product can be in the form of a liquid, paste, gel, solid, or powder in some embodiments. A hair care product as presently disclosed typically comprises one or more of the following ingredients, which are generally used to formulate hair care products: anionic surfactants such as polyoxyethylenelauryl ether sodium sulfate; cationic surfactants such as stearyltrimethylammonium chloride and/or distearyltrimethylammonium chloride; nonionic surfactants such as glyceryl monostearate, sorbitan monopalmitate and/or polyoxyethylenecetyl ether; wetting agents such as propylene glycol, 1,3-butylene glycol, glycerin, sorbitol, pyroglutamic acid salts, amino acids and/or trimethylglycine; hydrocarbons such as liquid paraffins, petrolatum, solid paraffins, squalane and/or olefin oligomers; higher alcohols such as stearyl alcohol and/or cetyl alcohol; superfatting agents; antidandruff agents; disinfectants; anti-inflammatory agents; crude drugs; water-soluble polymers such as methyl cellulose, hydroxycellulose and/or partially deacetylated chitin; antiseptics such as paraben; ultra-violet light absorbers; pearling agents; pH adjustors; perfumes; and pigments.

A pharmaceutical product herein can be in the form of an emulsion, liquid, elixir, gel, suspension, solution, cream, or ointment, for example. Also, a pharmaceutical product herein can be in the form of any of the personal care products disclosed herein, such as an antibacterial or antifungal composition. A pharmaceutical product can further comprise one or more pharmaceutically acceptable carriers, diluents, and/or pharmaceutically acceptable salts. A composition herein can also be used in capsules, encapsulants, tablets, tablet coatings, and as an excipients for medicaments and drugs.

A composition herein can be an encapsulant, for instance. An encapsulant can be used for controlling the release of, and/or protecting, the material and/or active agent(s)/compound(s) held within the encapsulant, for instance. An encapsulant herein can encapsulate a fragrance (e.g., any as disclosed in U.S. Pat. No. 7,196,049, which is incorporated herein by reference), ingestible product (e.g., food, beverage, a flavor such as disclosed in U.S. Pat. No. 7,022,352, which is incorporated herein by reference), pharmaceutical or health product (e.g., liquid drug, prebiotic, probiotic), personal care product (e.g., toothpaste, mouth wash, face/body cream), household care product (e.g., dry or liquid detergent, bleach). Any suitable composition/product disclosed elsewhere herein, or as disclosed in U.S. Patent Appl. Publ. Nos. 2009/0209661 or 2007/0148105 (each incorporated herein by reference, e.g., consumer product) can be encapsulated, for example. In some aspects, an encapsulant herein can encapsulate a hydrophobic or non-polar composition; a hydrophobic or non-polar composition can comprise a lipid (e.g., oil, essential oil, fat, wax, free fatty acids, glycerol, phospholipids, sterols, triglycerides, diglycerides, monoglycerides), alkane, alkene/olefin, a hydrophobic aromatic or cyclic compound, a hydrophobic aroma compound, and/or a hydrophobic flavorant or nutrient, for example. An encapsulated product herein can be in a dry form in some aspects. An encapsulant in some cases can have a composition/formulation, and/or thickness, that is the same as, or similar to, that of a film or coating herein, where such film or coating is suitable for use as an encapsulant. An encapsulant can comprise about, or at least about, 50, 60, 70, 80, 90, 91, 92, 93, 94, 95, 96, 97, 98, 99, or 100 wt % of a composition herein comprising (i) insoluble alpha-glucan and soluble alpha-glucan derivative, or (ii) insoluble alpha-glucan and additive, for example. This and/or other encapsulants herein can further comprise, in some aspects, polyurethane, polyvinyl acetate, poly acrylate, poly lactic acid, polysaccharide (in addition to insoluble alpha-glucan herein), gelatin, melamine, and/or formaldehyde. One or more additional additives can optionally be included that alter the mechanical, thermal, and/or degradation profile of an encapsulant herein.

In some aspects, an encapsulated composition as presently disclosed can be produced by a method comprising: (a) providing a liquid emulsion comprising at least a composition herein comprising (i) insoluble alpha-glucan and soluble alpha-glucan derivative, or (ii) insoluble alpha-glucan and additive, water and a liquid/compound that is immiscible in water (e.g., any hydrophobic or non-polar substance disclosed herein), and (b) removing all or most of (≥88%, 90%, 95%, 98%, 99%, 99.5%, 99.9% by weight) the water from the emulsion. Such removal can comprise drying such as by freeze-drying or spray-drying. A liquid emulsion can be provided in an encapsulation method, for example, by mixing and/or homogenizing the foregoing emulsion components. In some aspects, the temperature of the mixture to be emulsified is increased to aid emulsification. For example, the temperature can be raised in order to liquefy/melt a non-water component (immiscible component), such as a component that is solid at room temperature (e.g., the temperature is raised at least 1 or 2° C. above the melting point of the immiscible component), thereby providing the liquid/compound that is immiscible in water. The increased temperature of the emulsification is typically maintained until the point of entering the emulsification to the drying step. In an encapsulation method herein, it should be understood that, regarding the product of the method, the liquid/compound (or solid, as the case may be, depending on melting point) that is immiscible in water is encapsulated by a composition herein comprising (i) insoluble alpha-glucan and soluble alpha-glucan derivative, or (ii) insoluble alpha-glucan and additive. In some alternative aspects of an encapsulant or encapsulation method of the present disclosure, an insoluble alpha-glucan as disclosed herein can be used instead of, or in addition to, a composition comprising (i) insoluble alpha-glucan and soluble alpha-glucan derivative, or (ii) insoluble alpha-glucan and additive.

A household and/or industrial product herein can be in the form of drywall tape-joint compounds; mortars; grouts; cement plasters; spray plasters; cement stucco; adhesives; pastes; wall/ceiling texturizers; binders and processing aids for tape casting, extrusion forming, injection molding and ceramics; spray adherents and suspending/dispersing aids for pesticides, herbicides, and fertilizers; fabric care products such as fabric softeners and laundry detergents; hard surface cleaners; air fresheners; polymer emulsions; latex; gels such as water-based gels; surfactant solutions; paints such as water-based paints; protective coatings; adhesives; sealants and caulks; inks such as water-based ink; metal-working fluids; films or coatings; or emulsion-based metal cleaning fluids used in electroplating, phosphatizing, galvanizing and/or general metal cleaning operations, for example. In some aspects, a composition herein is comprised in a fluid as a viscosity modifier and/or friction reducer; such uses include downhole operations/fluids (e.g., in hydraulic fracturing and enhanced oil recovery).

Examples of ingestible products herein include a food, beverage, animal feed, an animal health and/or nutrition product, and/or pharmaceutical product. The intended use of a composition as presently disclosed in an ingestible product can be to provide texture, add volume, and/or thicken, for example.

Further examples of using a composition of the present disclosure for ingestible products include use as: a bulking, binding and/or coating ingredient; a carrier for coloring agents, flavors/fragrances, and/or high intensity sweeteners; a spray drying adjunct; a bulking, bodying, dispersing and/or emulsification agent; and an ingredient for promoting moisture retention (humectant). Illustrative examples of products that can be prepared having a composition herein include food products, beverage products, pharmaceutical products, nutritional products, and sports products. Examples of beverage products herein include concentrated beverage mixes, carbonated beverages, non-carbonated beverages, fruit-flavored beverages, fruit juices, teas, coffee, milk nectars, powdered drinks, liquid concentrates, milk drinks, ready-to-drink (RTD) products, smoothies, alcoholic beverages, flavored waters and combinations thereof. Examples of food products herein include baked goods (e.g., breads), confectioneries, frozen dairy products, meats, artificial/synthetic/cultured meat, cereal products (e.g., breakfast cereals), dairy products (e.g., yogurt), condiments (e.g., mustard, ketchup, mayonnaise), snack bars, soups, dressings, mixes, prepared foods, baby foods, diet preparations, peanut butter, syrups, sweeteners, food coatings, pet food, animal feed, animal health and nutrition products, dried fruit, sauces, gravies, jams/jellies, dessert products, spreads, batters, breadings, spice mixes, frostings and the like. In some aspects, a composition herein can provide or enhance the foaming of beverages such as dairy beverages, non-dairy alternative beverages (e.g., "vegan" milk such as soy milk, almond milk, or coconut milk), dairy creamers, and/or non-dairy creamers (e.g., for a hot beverage such as coffee [e.g., cappuccino], tea [e.g., chai tea]).

A composition herein (comprising [i] insoluble alpha-glucan and soluble alpha-glucan derivative, or [ii] insoluble alpha-glucan and additive) can be comprised in a personal care product, pharmaceutical product, household product, industrial product, or ingestible product (e.g., food product) in an amount that provides a desired degree of thickening and/or dispersion, for example. Examples of a concentration or amount of a disclosed composition in a product are any of the weight percentages provided above.

In some aspects, a composition herein comprising (i) insoluble alpha-glucan and soluble alpha-glucan derivative, or (ii) insoluble alpha-glucan and additive (e.g., particles of [i] or [ii]) can be in the form of a fabric care composition. A fabric care composition can be used for hand wash, machine wash and/or other purposes such as soaking and/or pretreatment of fabrics, for example. A fabric care composition may take the form of, for example, a laundry detergent; fabric conditioner; any wash-, rinse-, or dryer-added product; unit dose or spray. Fabric care compositions in a liquid form may be in the form of an aqueous composition. In other embodiments, a fabric care composition can be in a dry form such as a granular detergent or dryer-added fabric softener sheet. Other non-limiting examples of fabric care compositions can include: granular or powder-form all-purpose or heavy-duty washing agents; liquid, gel or paste-form all-purpose or heavy-duty washing agents: liquid or dry fine-fabric (e.g. delicates) detergents; cleaning auxiliaries such as bleach additives, "stain-stick", or pre-treatments; substrate-laden products such as dry and wetted wipes, pads, or sponges; sprays and mists; water-soluble unit dose articles. As further examples, a composition herein can be in the form of a liquid, a gel, a powder, a hydrocolloid, an aqueous solution, a granule, a tablet, a capsule, a bead or pastille, a single compartment sachet, a multi-compartment sachet, a single compartment pouch, or a multi-compartment pouch.

A detergent composition herein may be in any useful form, e.g., as powders, granules, pastes, bars, unit dose, or liquid. A liquid detergent may be aqueous, typically containing up to about 70 wt % of water and 0 wt %/o to about 30 wt % of organic solvent. It may also be in the form of a compact gel type containing only about 30 wt % water.

A detergent composition herein (e.g., of a fabric care product or any other product herein) typically comprises one or more surfactants, wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the detergent composition. A detergent will usually contain 0 wt % to about 50 wt %/o of an anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. In addition, a detergent composition may optionally contain 0 wt % to about 40 wt % of a nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO92/06154, which is incorporated herein by reference).

A detergent composition herein can optionally comprise one or more detergent builders or builder systems. In some aspects, oxidized alpha-1,3-glucan can be included as a co-builder; oxidized alpha-1,3-glucan compounds for use herein are disclosed in U.S. Patent Appl. Publ. No. 2015/0259439. In some aspects incorporating at least one builder, the cleaning compositions comprise at least about 1%, from about 3% to about 60%, or even from about 5% to about 40%, builder by weight of the composition. Examples of builders include alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Additional examples of a detergent builder or complexing agent include zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst).

In some embodiments, builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present disclosure, including those known in the art (See, e.g., EP2100949).

In some embodiments, suitable builders can include phosphate builders and non-phosphate builders. In some embodiments, a builder is a phosphate builder. In some embodiments, a builder is a non-phosphate builder. A builder can be used in a level of from 0.1% to 80%, or from 5% to 60%, or from 10% to 50%, by weight of the composition. In some embodiments, the product comprises a mixture of phosphate and non-phosphate builders. Suitable phosphate builders include mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include ammonium and/or alkali metal salts, i.e., lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

A detergent composition herein can comprise at least one chelating agent. Suitable chelating agents include, but are not limited to copper, iron and/or manganese chelating agents and mixtures thereof. In embodiments in which at least one chelating agent is used, the composition comprises from about 0.1% to about 15%, or even from about 3.0% to about 10%, chelating agent by weight of the composition.

A detergent composition herein can comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

A detergent composition herein can comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Additional dye transfer inhibiting agents include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetraacetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethyl ethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof, which can be used alone or in combination with any of the above. In embodiments in which at least one dye transfer inhibiting agent is used, a composition herein may comprise from about 0.0001% to about 10%, from about 0.01% to about 5%, or even from about 0.1% to about 3%, by weight of the composition.

A detergent composition herein can comprise silicates. In some of these embodiments, sodium silicates (e.g., sodium disilicate, sodium metasilicate, and/or crystalline phyllosilicates) find use. In some embodiments, silicates are present at a level of from about 1% to about 20% by weight of the composition. In some embodiments, silicates are present at a level of from about 5% to about 15% by weight of the composition.

A detergent composition herein can comprise dispersants. Suitable water-soluble organic materials include, but are not limited to the homo- or co-polymeric acids or their salts, in which the polycarboxylic acid comprises at least two carboxyl radicals separated from each other by not more than two carbon atoms.

A detergent composition herein may additionally comprise one or more enzymes as disclosed above, for example. In some aspects, a detergent composition can comprise one or more enzymes, each at a level from about 0.00001% to about 10% by weight of the composition and the balance of cleaning adjunct materials by weight of composition. In some other aspects, a detergent composition can also comprise each enzyme at a level of about 0.0001% to about 10%, about 0.001% to about 5%, about 0.001% to about 2%, or about 0.005% to about 0.5%, by weight of the composition. Enzymes comprised in a detergent composition herein may be stabilized using conventional stabilizing agents, e.g., a polyol such as propylene glycol or glycerol; a sugar or sugar alcohol; lactic acid; boric acid or a boric acid derivative (e.g., an aromatic borate ester).

A detergent composition in some aspects may comprise one or more other types of polymer in addition to those (insoluble alpha-glucan, soluble alpha-glucan derivative) as disclosed herein. Examples of other types of polymers useful herein include carboxymethyl cellulose (CMC), dextran, poly(vinylpyrrolidone) (PVP), polyethylene glycol (PEG), poly(vinyl alcohol) (PVA), polycarboxylates such as polyacrylates, maleic/acrylic acid copolymers and lauryl methacrylate/acrylic acid copolymers.

A detergent composition herein may contain a bleaching system. For example, a bleaching system can comprise an $H_2O_2$ source such as perborate or percarbonate, which may be combined with a peracid-forming bleach activator such as tetraacetylethylenediamine (TAED) or nonanoyloxybenzenesulfonate (NOBS). Alternatively, a bleaching system may comprise peroxyacids (e.g., amide, imide, or sulfone type peroxyacids). Alternatively still, a bleaching system can be an enzymatic bleaching system comprising perhydrolase, for example, such as the system described in WO2005/056783.

A detergent composition herein may also contain conventional detergent ingredients such as fabric conditioners, clays, foam boosters, suds suppressors, anti-corrosion agents, soil-suspending agents, anti-soil redeposition agents, dyes, bactericides, tarnish inhibiters, optical brighteners, or perfumes. The pH of a detergent composition herein (measured in aqueous solution at use concentration) is usually neutral or alkaline (e.g., pH of about 7.0 to about 11.0).

Examples of suitable anti-redeposition and/or clay soil removal agents for a fabric care product herein include polyethoxy zwitterionic surfactants, water-soluble copolymers of acrylic or methacrylic acid with acrylic or methacrylic acid-ethylene oxide condensates (e.g., U.S. Pat. No. 3,719,647), cellulose derivatives such as carboxymethylcellulose and hydroxypropylcellulose (e.g., U.S. Pat. Nos. 3,597,416 and 3,523,088), and mixtures comprising nonionic alkyl polyethoxy surfactant, polyethoxy alkyl quaternary cationic surfactant and fatty amide surfactant (e.g., U.S. Pat. No. 4,228,044). Non-limiting examples of other suitable anti-redeposition and clay soil removal agents are disclosed in U.S. Pat. Nos. 4,597,898 and 4,891,160, and International Patent Appl. Publ. No. WO95/32272, all of which are incorporated herein by reference.

Particular forms of detergent compositions that can be adapted for purposes disclosed herein are disclosed in, for example, US2009/0209445A1, US2010/0081598A1, U.S. Pat. No. 7,001,878B2, EP1504994B1, WO2001/085888A2, WO2003/089562A1, WO2009/098659A1, WO2009/098660A1, WO2009/112992A1, WO2009/124160A1, WO2009/152031A1, WO2010/059483A1, WO2010/088112A1, WO2010/090915A1, WO2010/135238A1, WO2011/094687A1, WO2011/094690A1, WO2011/127102A1, WO2011/163428A1, WO2008/000567A1, WO2006/045391A1, WO2006/007911A, WO2012/027404A1, EP1740690B1, WO2012/059336A1, U.S. 67/306,4681, WO2008/087426A1, WO2010/116139A1, and WO2012/104613A1, all of which are incorporated herein by reference.

Laundry detergent compositions herein can optionally be heavy duty (all purpose) laundry detergent compositions. Exemplary heavy duty laundry detergent compositions comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, e.g., C8-C18 alkyl ethoxylated alcohols and/or C6-C12 alkyl phenol alkoxylates), where the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof): zwitterionic and/or amphoteric detersive surfactants (selected from a group of alkanolamine sulpho-betaines); ampholytic surfactants; semi-polar non-ionic surfactants and mixtures thereof.

A detergent herein such as a heavy duty laundry detergent composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated $C_1$-C6 mono-carboxylic acid, $C_1$-C6 alkyl ester of acrylic or methacrylic acid, and mixtures thereof.

A detergent herein such as a heavy duty laundry detergent composition may optionally include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example REPEL-O-TEX SF, SF-2 AND SRP6, TEXCARE SRA100, SRA300, SRN100, SRN170, SRN240, SRN300 AND SRN325, MARLOQUEST SL), anti-redeposition agent(s) herein (0.1 wt % to 10 wt %), include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); and polymeric carboxylate (such as maleate/acrylate random copolymer or polyacrylate homopolymer).

A detergent herein such as a heavy duty laundry detergent composition may optionally further include saturated or unsaturated fatty acids, preferably saturated or unsaturated C12-C24 fatty acids (0 wt/o to 10 wt/o); deposition aids (examples for which include polysaccharides, cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic starch, cationic polyacrylamides, and mixtures thereof.

A detergent herein such as a heavy duty laundry detergent composition may optionally further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetraacetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

A detergent herein such as a heavy duty laundry detergent composition may optionally include silicone or fatty-acid based suds suppressors; hueing dyes, calcium and magnesium cations, visual signaling ingredients, anti-foam (0.001 wt % to about 4.0 wt %), and/or a structurant/thickener (0.01 wt % to 5 wt %) selected from the group consisting of diglycerides and triglycerides, ethylene glycol distearate, microcrystalline cellulose, microfiber cellulose, biopolymers, xanthan gum, gellan gum, and mixtures thereof). A structurant can also be referred to as a structural agent.

A detergent herein can be in the form of a heavy duty dry/solid laundry detergent composition, for example. Such a detergent may include: (i) a detersive surfactant, such as any anionic detersive surfactant disclosed herein, any non-ionic detersive surfactant disclosed herein, any cationic detersive surfactant disclosed herein, any zwitterionic and/or amphoteric detersive surfactant disclosed herein, any ampholytic surfactant, any semi-polar non-ionic surfactant, and mixtures thereof; (ii) a builder, such as any phosphate-free builder (e.g., zeolite builders in the range of 0 wt % to less than 10 wt %), any phosphate builder (e.g., sodium tri-polyphosphate in the range of 0 wt % to less than 10 wt %), citric acid, citrate salts and nitrilotriacetic acid, any silicate salt (e.g., sodium or potassium silicate or sodium meta-silicate in the range of 0 wt % to less than 10 wt %); any carbonate salt (e.g., sodium carbonate and/or sodium bicarbonate in the range of 0 wt % to less than 80 wt %), and mixtures thereof; (iii) a bleaching agent, such as any photobleach (e.g., sulfonated zinc phthalocyanines, sulfonated aluminum phthalocyanines, xanthenes dyes, and mixtures thereof), any hydrophobic or hydrophilic bleach activator (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), any source of hydrogen peroxide (e.g., inorganic perhydrate salts, examples of which include mono or tetra hydrate sodium salt of perborate, percarbonate, persulfate, perphosphate, or persilicate), any preformed hydrophilic and/or hydrophobic peracids (e.g., percarboxylic acids and salts, percarbonic acids and salts, perimidic acids and salts, peroxymonosulfuric acids and salts, and mixtures thereof); and/or (iv) any other components such as a bleach catalyst (e.g., imine bleach boosters examples of which include iminium cations and polyions, iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof), and a metal-containing bleach catalyst (e.g., copper, iron, titanium, ruthenium, tungsten, molybdenum, or manganese cations along with an auxiliary metal cations such as zinc or aluminum and a sequestrate such as EDTA, ethylenediaminetetra(methylenephosphonic acid).

A detergent herein such as that for fabric care (e.g., laundry) can be comprised in a unit dose (e.g., sachet or pouch), for example. A unit dose form can comprise a water-soluble outer film that completely envelopes a liquid or solid detergent composition. A unit dose can comprise a single compartment, or at least two, three, or more (multiple) compartments. Multiple compartments can be arranged in a superposed orientation or a side-by-side orientation. A unit dose herein is typically a closed structure of any form/shape suitable for holding and protecting its contents without allowing contents release prior to contact with water.

Compositions disclosed herein comprising (i) insoluble alpha-glucan and soluble alpha-glucan derivative, or (ii) insoluble alpha-glucan and additive (e.g., particles of [i] or [ii]) can be in the form of, or comprise, a fabric softener (liquid fabric softener), for example. An example of such a composition is a rinse used in laundering a fabric-comprising material herein typically following cleaning of the fabric-comprising material with a laundry detergent composition (e.g., laundry rinse such as used in a laundry rinse cycle in a washing machine). The concentration of a composition of (i) or (ii) (above) in a composition comprising fabric softener (e.g., a rinse) can be about, or at least about, 20, 30, 40, 50, 60, 70, 80, 20-80, 20-70, 20-60, 30-80, 30-70, 30-60, 40-80, 40-70, or 40-60 ppm, for example. The concentration of a fabric softener in a composition (e.g., a rinse) can be about, or at least about, 50, 75, 100, 150, 200, 300, 400, 500, 600, 50-600, 50-500, 50-400, 50-300, 50-200, 100-600, 100-500, 100-400, 100-300, 100-200, 10-600, 50-500, 50-400, 50-300, 50-200, 200-600, 200-500, 200-400, or 200-300 ppm, for example. Fabric softener concentration can be based on the total fabric softener composition added (not necessarily based on an individual component of the fabric softener), or based on one or more fabric softening agents(s) in the fabric softener formulation. A fabric softener herein can further comprise, for example, one or more of a fabric softening agent (e.g., diethyl ester dimethyl ammonium chloride), anti-static agent, perfume, wetting agent, viscosity modifier (e.g., calcium chloride), pH buffer/buffering agent (e.g., formic acid), antimicrobial agent, anti-oxidant, radical scavenger (e.g., ammonium chloride), chelant/builder (e.g., diethylenetriamine pentaacetate), anti-foaming agent/lubricant (e.g., polydimethylsiloxane), preservative (e.g., benzisothiazolinone) and colorant. In some aspects, a fabric softener can further comprise one or more of a fabric softening agent, viscosity modifier, pH buffer/buffering agent, radical scavenger, chelant/builder and anti-foaming agent/lubricant. A fabric softener can be perfume-free and/or dye-free, or have less than about 0.1 wt % of a perfume and/or dye in some aspects. In some aspects, a fabric softener that can be adapted for use herein can be as disclosed in any of U.S. Patent Appl. Publ. Nos. 2014/0366282, 2001/0018410, 2006/0058214, 2021/0317384, or 2006/0014655, or Int. Patent Appl. Publ. Nos. WO2007/078782, WO1998/016538, WO1998/012293, WO1998007920, WO2000/070004, WO2009/146981, WO2000/170005, or WO2013087366. Some brands of fabric softeners that can be adapted for use herein, if desired, include DOWNY, DOWNY ULTRA, DOWNY INFUSIONS, ALL, SNUGGLE, LENOR and GAIN. A liquid fabric softener product (e.g., as it exists before being used in a laundry rinse cycle) can be formulated to include at least a composition of (i) or (ii) (above) in some aspects.

Compositions disclosed herein comprising (i) insoluble alpha-glucan and soluble alpha-glucan derivative, or (ii) insoluble alpha-glucan and additive (e.g., particles of [i] or [ii]) can be in the form of a dishwashing detergent composition, for example. Examples of dishwashing detergents include automatic dishwashing detergents (typically used in dishwasher machines) and hand-washing dish detergents. A dishwashing detergent composition can be in any dry or liquid/aqueous form as disclosed herein, for example. Components that may be included in some aspects of a dishwashing detergent composition include, for example, one or more of a phosphate: oxygen- or chlorine-based bleaching agent; non-ionic surfactant; alkaline salt (e.g., metasilicates, alkali metal hydroxides, sodium carbonate); any active enzyme disclosed herein; anti-corrosion agent (e.g., sodium silicate); anti-foaming agent; additives to slow down the removal of glaze and patterns from ceramics; perfume; anti-caking agent (in granular detergent); starch (in tablet-based detergents); gelling agent (in liquid/gel based detergents); and/or sand (powdered detergents).

Dishwashing detergents such as an automatic dishwasher detergent or liquid dishwashing detergent can comprise (i) a non-ionic surfactant, including any ethoxylated non-ionic surfactant, alcohol alkoxylated surfactant, epoxy-capped poly(oxyalkylated) alcohol, or amine oxide surfactant present in an amount from 0 to 10 wt %; (ii) a builder, in the range of about 5-60 wt %, including any phosphate builder (e.g., mono-phosphates, di-phosphates, tri-polyphosphates, other oligomeric-polyphosphates, sodium tripolyphosphate-STPP), any phosphate-free builder (e.g., amino acid-based compounds including methyl-glycine-diacetic acid [MGDA] and salts or derivatives thereof, glutamic-N,N-diacetic acid [GLDA] and salts or derivatives thereof, iminodisuccinic acid (IDS) and salts or derivatives thereof, carboxy methyl inulin and salts or derivatives thereof, nitrilotriacetic acid [NTA], diethylene triamine penta acetic acid [DTPA], B-alaninediacetic acid [B-ADA] and salts thereof), homopolymers and copolymers of poly-carboxylic acids and partially or completely neutralized salts thereof, monomeric polycarboxylic acids and hydroxycarboxylic acids and salts thereof in the range of 0.5 wt % to 50 wt %, or sulfonated/carboxylated polymers in the range of about 0.1 wt % to about 50 wt %; (iii) a drying aid in the range of about 0.1 wt % to about 10 wt % (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds thereof, particularly of the reactive cyclic carbonate and urea type); (iv) a silicate in the range from about 1 wt % to about 20 wt % (e.g., sodium or potassium silicates such as sodium disilicate, sodium meta-silicate and crystalline phyllosilicates); (v) an inorganic bleach (e.g., perhydrate salts such as perborate, percarbonate, perphosphate, persulfate and persilicate salts) and/or an organic bleach (e.g., organic peroxyacids such as diacyl- and tetraacylperoxides, especially diperoxydodecanedioic acid, diperoxytetradecanedioic acid, and diperoxyhexadecanedioic acid); (vi) a bleach activator (e.g., organic peracid precursors in the range from about 0.1 wt % to about 10 wt %) and/or bleach catalyst (e.g., manganese triazacyclononane and related complexes; Co, Cu, Mn, and Fe bispyridylamine and related complexes; and pentamine acetate cobalt(III) and related complexes); (vii) a metal care agent in the range from about 0.1 wt % to 5 wt % (e.g., benzatriazoles, metal salts and complexes, and/or silicates); (viii) a glass corrosion inhibitor in the range of about 0.1 wt % to 5 wt % (e.g., a salt and/or complex of magnesium, zinc, or bismuth); and/or (ix) any active enzyme disclosed herein in the range from about 0.01 to 5.0 mg of active enzyme per gram of automatic dishwashing detergent composition, and an enzyme stabilizer component (e.g., oligosaccharides, polysaccharides, and inorganic divalent metal salts). In some aspects, a dishwashing detergent ingredient or entire composition (but adapted accordingly to comprise a composition herein) can be as disclosed in U.S. Pat. No. 8,575,083 or 9,796,951, or U.S. Pat. Appl. Publ. No. 2017/0044468, which are each incorporated herein by reference.

A detergent herein such as that for dish care can be comprised in a unit dose (e.g., sachet or pouch) (e.g., water-soluble unit dose article), for example, and can be as described above for a fabric care detergent, but rather comprise a suitable dish detergent composition.

It is believed that numerous commercially available detergent formulations can be adapted to include a composition herein comprising (i) insoluble alpha-glucan and soluble alpha-glucan derivative, or (ii) insoluble alpha-glucan and additive (e.g., particles of [i] or [ii]). Examples of commercially available detergent formulations include PUREX® ULTRAPACKS (Henkel), FINISH® QUANTUM (Reckitt Benckiser), CLOROX™ 2 PACKS (Clorox), OXICLEAN MAX FORCE POWER PAKS (Church & Dwight), TIDE® STAIN RELEASE, CASCADE® ACTIONPACS, and TIDE® PODS™ (Procter & Gamble).

Compositions disclosed herein comprising (i) insoluble alpha-glucan and soluble alpha-glucan derivative, or (ii) insoluble alpha-glucan and additive (e.g., particles of [i] or [ii]) can be in the form of an oral care composition, for example. Examples of oral care compositions include dentifrices, toothpaste, mouth wash, mouth rinse, chewing gum, and edible strips that provide some form of oral care (e.g., treatment or prevention of cavities [dental caries], gingivitis, plaque, tartar, and/or periodontal disease). An oral care composition can also be for treating an "oral surface", which encompasses any soft or hard surface within the oral cavity including surfaces of the tongue, hard and soft palate, buccal mucosa, gums and dental surfaces. A "dental surface" herein is a surface of a natural tooth or a hard surface of artificial dentition including a crown, cap, filling, bridge, denture, or dental implant, for example.

An oral care composition herein can comprise about 0.01-15.0 wt % (e.g., ~0.1-10 wt % or ~0.1-5.0 wt %, ~0.1-2.0 wt %) of a composition as disclosed herein, for example. A composition herein as comprised in an oral care composition can sometimes be provided therein as a thickening agent and/or dispersion agent, which may be useful to impart a desired consistency and/or mouth feel to the composition. One or more other thickening or dispersion agents can also be provided in an oral care composition herein, such as a carboxyvinyl polymer, carrageenan (e.g., L-carrageenan), natural gum (e.g., karaya, xanthan, gum arabic, tragacanth), colloidal magnesium aluminum silicate, or colloidal silica, for example.

An oral care composition herein may be a toothpaste or other dentifrice, for example. Such compositions, as well as any other oral care composition herein, can additionally comprise, without limitation, one or more of an anticaries agent, antimicrobial or antibacterial agent, anticalculus or tartar control agent, surfactant, abrasive, pH-modifying agent, foam modulator, humectant, flavorant, sweetener, pigment/colorant, whitening agent, and/or other suitable components. Examples of oral care compositions to which a composition herein can be added are disclosed in U.S. Patent Appl. Publ. Nos. 2006/0134025, 2002/0022006 and 2008/0057007, which are incorporated herein by reference.

An anticaries agent herein can be an orally acceptable source of fluoride ions. Suitable sources of fluoride ions include fluoride, monofluorophosphate and fluorosilicate salts as well as amine fluorides, including olaflur (N'-octadecyltrimethylendiamine-N,N,N'-tris(2-ethanol)-dihydrofluoride), for example. An anticaries agent can be present in an amount providing a total of about 100-20000 ppm, about 200-5000 ppm, or about 500-2500 ppm, fluoride ions to the composition, for example. In oral care compositions in which sodium fluoride is the sole source of fluoride ions, an amount of about 0.01-5.0 wt %, about 0.05-1.0 wt %, or about 0.1-0.5 wt %, sodium fluoride can be present in the composition, for example.

An antimicrobial or antibacterial agent suitable for use in an oral care composition herein includes, for example, phenolic compounds (e.g., 4-allylcatechol; p-hydroxybenzoic acid esters such as benzylparaben, butylparaben, ethylparaben, methylparaben and propylparaben; 2-benzylphenol; butylated hydroxyanisole; butylated hydroxytoluene; capsaicin; carvacrol; creosol; eugenol; guaiacol; halogenated bisphenolics such as hexachlorophene and bromochlorophene; 4-hexylresorcinol; 8-hydroxyquinoline and salts thereof; salicylic acid esters such as menthyl salicylate, methyl salicylate and phenyl salicylate; phenol; pyrocatechol; salicylanilide; thymol; halogenated diphenylether compounds such as triclosan and tricosan monophosphate), copper (11) compounds (e.g., copper (II) chloride, fluoride, sulfate and hydroxide), zinc ion sources (e.g., zinc acetate, citrate, gluconate, glycinate, oxide, and sulfate), phthalic acid and salts thereof (e.g., magnesium monopotassium phthalate), hexetidine, octenidine, sanguinarine, benzalkonium chloride, domiphen bromide, alkylpyridinium chlorides (e.g. cetylpyridinium chloride, tetradecylpyridinium chloride, N-tetradecyl-4-ethylpyridinium chloride), iodine, sulfonamides, bisbiguanides (e.g., alexidine, chlorhexidine, chlorhexidine digluconate), piperidino derivatives (e.g., delmopinol, octapinol), *magnolia* extract, grapeseed extract, rosemary extract, menthol, geraniol, citral, eucalyptol, antibiotics (e.g., augmentin, amoxicillin, tetracycline, doxycycline, minocycline, metronidazole, neomycin, kanamycin, clindamycin), and/or any antibacterial agents disclosed in U.S. Pat. No. 5,776,435, which is incorporated herein by reference. One or more antimicrobial agents can optionally be present at about 0.01-10 wt % (e.g., 0.1-3 wt %), for example, in the disclosed oral care composition.

An anticalculus or tartar control agent suitable for use in an oral care composition herein includes, for example, phosphates and polyphosphates (e.g., pyrophosphates), polyaminopropanesulfonic acid (AMPS), zinc citrate trihydrate, polypeptides (e.g., polyaspartic and polyglutamic acids), polyolefin sulfonates, polyolefin phosphates, diphosphonates (e.g.,azacycloalkane-2,2-diphosphonates such as azacycloheptane-2,2-diphosphonic acid), N-methyl azacyclopentane-2,3-diphosphonic acid, ethane-1-hydroxy-1,1-diphosphonic acid (EHDP), ethane-1-amino-1,1-diphosphonate, and/or phosphonoalkane carboxylic acids and salts thereof (e.g., their alkali metal and ammonium salts). Useful inorganic phosphate and polyphosphate salts include, for example, monobasic, dibasic and tribasic sodium phosphates, sodium tripolyphosphate, tetrapolyphosphate, mono-, di-, tri- and tetra-sodium pyrophosphates, disodium dihydrogen pyrophosphate, sodium trimetaphosphate, sodium hexametaphosphate, or any of these in which sodium is replaced by potassium or ammonium. Other useful anticalculus agents in certain embodiments include anionic polycarboxylate polymers (e.g., polymers or copolymers of acrylic acid, methacrylic, and maleic anhydride such as polyvinyl methyl ether/maleic anhydride copolymers). Still other useful anticalculus agents include sequestering agents such as hydroxycarboxylic acids (e.g., citric, fumaric, malic, glutaric and oxalic acids and salts thereof) and aminopolycarboxylic acids (e.g., EDTA). One or more anticalculus or tartar control agents can optionally be present at about 0.01-50 wt % (e.g., about 0.05-25 wt % or about 0.1-15 wt %), for example, in the disclosed oral care composition.

A surfactant suitable for use in an oral care composition herein may be anionic, non-ionic, or amphoteric, for example. Suitable anionic surfactants include, without limitation, water-soluble salts of $C_{8-20}$ alkyl sulfates, sulfonated monoglycerides of $C_{8-20}$ fatty acids, sarcosinates, and taurates. Examples of anionic surfactants include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable non-ionic surfactants include, without limitation, poloxamers, polyoxyethylene sorbitan esters, fatty alcohol ethoxylates, alkylphenol ethoxylates, tertiary amine oxides, tertiary phosphine oxides, and dialkyl sulfoxides. Suitable amphoteric surfactants include, without limitation, derivatives of $C_{8-20}$ aliphatic secondary and tertiary amines having an anionic group such as a carboxylate, sulfate, sulfonate, phosphate or phosphonate. An example of a suitable amphoteric surfactant is cocoamidopropyl betaine. One or more surfactants are optionally present in a total amount of about 0.01-10 wt % (e.g., about 0.05-5.0 wt % or about 0.1-2.0 wt %), for example, in the disclosed oral care composition.

An abrasive suitable for use in an oral care composition herein may include, for example, silica (e.g., silica gel, hydrated silica, precipitated silica), alumina, insoluble phosphates, calcium carbonate, and resinous abrasives (e.g., a urea-formaldehyde condensation product). Examples of insoluble phosphates useful as abrasives herein are orthophosphates, polymetaphosphates and pyrophosphates, and include dicalcium orthophosphate dihydrate, calcium pyrophosphate, beta-calcium pyrophosphate, tricalcium phosphate, calcium polymetaphosphate and insoluble sodium polymetaphosphate. One or more abrasives are optionally present in a total amount of about 5-70 wt % (e.g., about 10-56 wt % or about 15-30 wt %), for example, in the disclosed oral care composition. The average particle size of an abrasive in certain embodiments is about 0.1-30 microns (e.g., about 1-20 microns or about 5-15 microns).

An oral care composition in certain embodiments may comprise at least one pH-modifying agent. Such agents may be selected to acidify, make more basic, or buffer the pH of a composition to a pH range of about 2-10 (e.g., pH ranging from about 2-8, 3-9, 4-8, 5-7, 6-10, or 7-9). Examples of pH-modifying agents useful herein include, without limitation, carboxylic, phosphoric and sulfonic acids; acid salts (e.g., monosodium citrate, disodium citrate, monosodium malate); alkali metal hydroxides (e.g. sodium hydroxide, carbonates such as sodium carbonate, bicarbonates, sesquicarbonates); borates; silicates; phosphates (e.g., monosodium phosphate, trisodium phosphate, pyrophosphate salts); and imidazole.

A foam modulator suitable for use in an oral care composition herein may be a polyethylene glycol (PEG), for example. High molecular weight PEGs are suitable, including those having an average molecular weight of about 200000-7000000 (e.g., about 500000-5000000 or about 1000000-2500000), for example. One or more PEGs are optionally present in a total amount of about 0.1-10 wt % (e.g. about 0.2-5.0 wt % or about 0.25-2.0 wt %), for example, in the disclosed oral care composition.

An oral care composition in certain embodiments may comprise at least one humectant. A humectant in certain embodiments may be a polyhydric alcohol such as glycerin, sorbitol, xylitol, or a low molecular weight PEG. Most suitable humectants also may function as a sweetener herein. One or more humectants are optionally present in a total amount of about 1.0-70 wt % (e.g., about 1.0-50 wt %, about 2-25 wt %, or about 5-15 wt %), for example, in the disclosed oral care composition.

A natural or artificial sweetener may optionally be comprised in an oral care composition herein. Examples of suitable sweeteners include dextrose, sucrose, maltose, dextrin, invert sugar, mannose, xylose, ribose, fructose, levulose, galactose, corn syrup (e.g., high fructose corn syrup or corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, and cyclamates. One or more sweeteners are optionally present in a total amount of about 0.005-5.0 wt %, for example, in the disclosed oral care composition.

A natural or artificial flavorant may optionally be comprised in an oral care composition herein. Examples of suitable flavorants include vanillin; sage; marjoram; parsley oil; spearmint oil; cinnamon oil; oil of wintergreen (methylsalicylate); peppermint oil; clove oil; bay oil; anise oil; *eucalyptus* oil; citrus oils; fruit oils; essences such as those derived from lemon, orange, lime, grapefruit, apricot, banana, grape, apple, strawberry, cherry, or pineapple; bean- and nut-derived flavors such as coffee, cocoa, cola, peanut, or almond; and adsorbed and encapsulated flavorants. Also encompassed within flavorants herein are ingredients that provide fragrance and/or other sensory effect in the mouth, including cooling or warming effects. Such ingredients include, without limitation, menthol, menthyl acetate, menthyl lactate, camphor, *eucalyptus* oil, eucalyptol, anethole, eugenol, *cassia*, oxanone, Irisone®, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), and menthone glycerol acetal (MGA). One or more flavorants are optionally present in a total amount of about 0.01-5.0 wt % (e.g., about 0.1-2.5 wt %), for example, in the disclosed oral care composition.

An oral care composition in certain embodiments may comprise at least one bicarbonate salt. Any orally acceptable bicarbonate can be used, including alkali metal bicarbonates such as sodium or potassium bicarbonate, and ammonium bicarbonate, for example. One or more bicarbonate salts are optionally present in a total amount of about 0.1-50 wt % (e.g., about 1-20 wt %), for example, in the disclosed oral care composition.

An oral care composition in certain embodiments may comprise at least one whitening agent and/or colorant. A suitable whitening agent is a peroxide compound such as any of those disclosed in U.S. Pat. No. 8,540,971, which is incorporated herein by reference. Suitable colorants herein include pigments, dyes, lakes and agents imparting a particular luster or reflectivity such as pearling agents, for example. Specific examples of colorants useful herein include talc; mica; magnesium carbonate; calcium carbonate; magnesium silicate; magnesium aluminum silicate; silica; titanium dioxide; zinc oxide; red, yellow, brown and black iron oxides; ferric ammonium ferrocyanide; manganese violet; ultramarine; titaniated mica; and bismuth oxychloride. One or more colorants are optionally present in a total amount of about 0.001-20 wt % (e.g., about 0.01-10 wt % or about 0.1-5.0 wt %), for example, in the disclosed oral care composition.

Additional components that can optionally be included in an oral composition herein include one or more enzymes (above), vitamins, and anti-adhesion agents, for example. Examples of vitamins useful herein include vitamin C, vitamin E, vitamin B5, and folic acid. Examples of suitable anti-adhesion agents include solbrol, ficin, and quorum-sensing inhibitors.

Additional examples of personal care, household care, and other products and ingredients herein can be any as disclosed in U.S. Pat. No. 8,796,196, which is incorporated herein by reference. Examples of personal care, household care, and other products and ingredients herein include perfumes, fragrances, air odor-reducing agents, insect repellents and insecticides, bubble-generating agents such as surfactants, pet deodorizers, pet insecticides, pet shampoos, disinfecting agents, hard surface (e.g., floor, tub/shower, sink, toilet bowl, door handle/panel, glass/window, car/automobile exterior or interior) treatment agents (e.g., cleaning, disinfecting, and/or coating agents), wipes and other non-woven materials, colorants, preservatives, antioxidants, emulsifiers, emollients, oils, medicaments, flavors, and suspending agents.

The present disclosure also concerns a method of treating a material. This method comprises contacting a material with an aqueous composition comprising (i) an insoluble alpha-glucan and soluble alpha-glucan derivative, or (ii) an insoluble alpha-glucan and additive (e.g., particles of [i] or [ii]) as disclosed herein.

A material contacted with an aqueous composition in a contacting method herein can comprise a fabric in some aspects. A fabric herein can comprise natural fibers, synthetic fibers, semi-synthetic fibers, or any combination thereof. A semi-synthetic fiber herein is produced using naturally occurring material that has been chemically derivatized, an example of which is rayon. Non-limiting examples of fabric types herein include fabrics made of (i) cellulosic fibers such as cotton (e.g., broadcloth, canvas, chambray, chenille, chintz, corduroy, cretonne, damask, denim, flannel, gingham, jacquard, knit, matelasse, oxford, percale, poplin, plisse, sateen, seersucker, sheers, terry cloth, twill, velvet), rayon (e.g., viscose, modal, lyocell), linen, and Tencel®; (ii) proteinaceous fibers such as silk, wool and related mammalian fibers; (iii) synthetic fibers such as polyester, acrylic, nylon, and the like; (iv) long vegetable fibers from jute, flax, ramie, coir, kapok, sisal, henequen, abaca, hemp and sunn; and (v) any combination of a fabric of (i)-(iv). Fabric comprising a combination of fiber types (e.g., natural and synthetic) include those with both a cotton fiber and polyester, for example. Materials/articles containing one or more fabrics herein include, for example, clothing, curtains, drapes, upholstery, carpeting, bed linens, bath linens, tablecloths, sleeping bags, tents, car interiors, etc. Other materials comprising natural and/or synthetic fibers include, for example, non-woven fabrics, paddings, paper, and foams.

An aqueous composition that is contacted with a fabric can be, for example, a fabric care composition (e.g., laundry detergent, fabric softener). Thus, a treatment method in certain embodiments can be considered a fabric care method or laundry method if employing a fabric care composition therein. A fabric care composition herein is contemplated to effect one or more of the following fabric care benefits (i.e., surface substantive effects): wrinkle removal, wrinkle reduction, wrinkle resistance, fabric wear reduction, fabric wear resistance, fabric pilling reduction, extended fabric life, fabric color maintenance, fabric color fading reduction, reduced dye transfer, fabric color restoration, fabric soiling reduction, fabric soil release, fabric shape retention, fabric smoothness enhancement, anti-redeposition of soil on fabric, anti-greying of laundry, improved fabric hand/handle, and/or fabric shrinkage reduction.

Examples of conditions (e.g., time, temperature, wash/rinse volumes) for conducting a fabric care method or laundry method herein are disclosed in WO1997/003161 and U.S. Pat. Nos. 4,794,661, 4,580,421 and 5,945,394, which are incorporated herein by reference. In other examples, a material comprising fabric can be contacted with an aqueous composition herein: (i) for at least about 5, 10, 20, 30, 40, 50, 60, 70, 80, 90, 100, 110, or 120 minutes; (ii) at a temperature of at least about 10, 15, 20, 25, 30, 35, 40, 45, 50, 55, 60, 65, 70, 75, 80, 85, 90, or 95° C. (e.g., for laundry wash or rinse: a "cold" temperature of about 15-30° C., a "warm" temperature of about 30-50° C., a "hot" temperature of about 50-95° C.); (iii) at a pH of about 2, 3, 4, 5, 6, 7, 8, 9, 10, 11, or 12 (e.g., pH range of about 2-12, or about 3-11); (iv) at a salt (e.g., NaCl) concentration of at least about 0.5, 1.0, 1.5, 2.0, 2.5, 3.0, 3.5, or 4.0 wt %; or any combination of (i)-(iv).

The contacting step in a fabric care method or laundry method can comprise any of washing, soaking, and/or rinsing steps, for example. Contacting a material or fabric in still further embodiments can be performed by any means known in the art, such as dissolving, mixing, shaking, spraying, treating, immersing, flushing, pouring on or in, combining, painting, coating, applying, affixing to, and/or communicating an effective amount of a composition herein with the fabric or material. In still further embodiments, contacting may be used to treat a fabric to provide a surface substantive effect. As used herein, the term "fabric hand" or "handle" refers to a person's tactile sensory response towards fabric which may be physical, physiological, psychological, social or any combination thereof. In one embodiment, the fabric hand may be measured using a PhabrOmeter® System for measuring relative hand value (available from Nu Cybertek, Inc. Davis, CA) (American Association of Textile Chemists and Colorists [AATCC test method "202-2012, Relative Hand Value of Textiles: Instrumental Method" ]).

In some aspects of treating a material comprising fabric, the (i) insoluble alpha-glucan and soluble alpha-glucan derivative, or (ii) insoluble alpha-glucan and additive of the aqueous composition adsorb to the fabric. This feature is believed to render compositions herein useful as anti-redeposition agents and/or anti-greying agents in fabric care compositions (in addition to their viscosity-modifying and/or builder effects). An anti-redeposition agent or anti-greying agent herein helps keep soil from redepositing onto clothing in wash water after the soil has been removed.

Other materials that can be contacted in the above treatment method include surfaces that can be treated with a dish detergent (e.g., automatic dishwashing detergent or hand dish detergent). Examples of such materials include surfaces of dishes, glasses, pots, pans, baking dishes, utensils and flatware made from ceramic material, china, metal, glass, plastic (e.g., polyethylene, polypropylene, polystyrene, melamine, etc.) and wood (collectively referred to herein as "tableware"). Thus, the treatment method in certain embodiments can be considered a dishwashing method or tableware washing method, for example. Examples of conditions (e.g., time, temperature, wash volume) for conducting a dishwashing or tableware washing method herein are disclosed herein and in U.S. Pat. No. 8,575,083 and U.S. Pat. Appl. Publ. No. 2017/0044468, which are incorporated herein by reference. In some aspects, a tableware article can be contacted with an aqueous composition herein under a suitable set of conditions such as any of those disclosed above with regard to contacting a fabric-comprising material.

Other materials that can be contacted in the above treatment method include oral surfaces such as any soft or hard surface within the oral cavity including surfaces of the tongue, hard and soft palate, buccal mucosa, gums and dental surfaces (e.g., natural tooth or a hard surface of artificial dentition such as a crown, cap, filling, bridge, denture, or dental implant). Thus, a treatment method in certain embodiments can be considered an oral care method or dental care method, for example. Conditions (e.g., time, temperature) for contacting an oral surface with an aqueous composition herein should be suitable for the intended purpose of making such contact. Other surfaces that can be contacted in a treatment method also include a surface of the integumentary system such as skin, hair or nails.

Thus, some aspects of the present disclosure concern material (e.g., fabric, or a fiber-comprising product as disclosed herein) that comprises a composition of the present disclosure. Such material can be produced following a material treatment method as disclosed herein, for example. A material may comprise a composition herein if the composition is adsorbed to, or otherwise in contact with, the surface of the material, for example.

Some aspects of a method of treating a material herein further comprise a drying step, in which a material is dried after being contacted with the aqueous composition. A drying step can be performed directly after the contacting step, or following one or more additional steps that might follow the contacting step (e.g., drying of fabric or tableware after being rinsed, in water for example, following a wash in an aqueous composition herein). Drying can be performed by any of several means known in the art, such as air drying (e.g., ~20-25° C.), or at a temperature of at least about 30, 40, 50, 60, 70, 80, 90, 100, 120, 140, 160, 170, 175, 180, or 200° C., for example. A material that has been dried herein typically has less than 3, 2, 1, 0.5, or 0.1 wt % water comprised therein. Fabric is a preferred material for conducting an optional drying step.

An aqueous composition used in a treatment method herein can be any aqueous composition disclosed herein. Examples of aqueous compositions include detergents (e.g., laundry detergent or dish detergent), fabric softeners, and water-containing dentifrices such as toothpaste.

In some aspects, a material that can be treated with an aqueous composition (e.g., dispersion/emulsion) herein is a non-woven product. This treatment, which can involve application of an aqueous composition herein (at any concentration disclosed herein) typically followed by a drying step (e.g., air drying, heated drying, vacuum drying; drying temperature can be any suitable temperature disclosed herein, for example), can strengthen (i.e., act as a binder for) a non-woven product. In some aspects, particles as presently disclosed can increase the dry or wet tensile strength (measured in N/5 cm) of a non-woven by about, or at least about, 1000%, 10000%, 100000%, or 1000000%, for example. Thus, further provided herein are non-woven products containing a binder/strengthening agent that comprises particles of the present disclosure. In some aspects, the dry or wet tensile strength of a non-woven comprising particles herein can be about, or at least about, 10, 15, 20, 25, 50, 75, 100, 125, 130, 135, 140, 145, 150, 10-150, 15-150, 20-150, 25-150, 10-140, 15-140, 20-140, or 25-140 N/5 cm. On a basis of the total weight of non-woven material and particles in a non-woven product, the content of the particles therein can be about 5, 10, 15, 20, 25, 5-25, 5-20, 10-25, or 10-20 wt %. A non-woven product herein can be, for example, air-laid, dry-laid, wet-laid, carded, electrospun, spun-lace, spun-bond, or melt-blown. In some aspects, a non-woven product can be an abrasive or scouring sheet, agricultural covering, agricultural seed strip, apparel lining, automobile headliner or upholstery, bib, cheese wrap, civil engineering fabric, coffee filter, cosmetic remover or applicator, detergent pouch/sachet, fabric softener sheet, envelope, face mask, filter, garment bag, heat or electricity conductive fabric, household care wipe (e.g., for floor care, hard surface cleaning, pet care etc.), house wrap, hygiene product (e.g., sanitary pad/napkin, underpad), insulation, label, laundry aid, medical care or personal injury care product (e.g., bandage, cast padding or cover, dressing, pack, sterile overwrap, sterile packaging, surgical drape, surgical gown, swab), mop, napkin or paper towel, paper, personal wipe or baby wipe, reusable bag, roofing undercovering, table linen, tag, tea or coffee bag, upholstery, vacuum cleaning bag, or wallcovering. The fiber of a non-woven product can comprise cellulose and/or alpha-1,3-glucan in some aspects, or can comprise one or more other materials disclosed herein that can be used to form a fiber. Examples of non-woven products herein, non-woven product materials, and/or methods of production of non-woven products and materials, can be as disclosed in Int. Pat. Appl. Publ. No. WO2019055397 or U.S. Pat. Appl. Publ. Nos. 2018/0282918, 2017/0167063, 2018/0320291, or 2010/0291213, which are each incorporated herein by reference.

In some aspects, an aqueous composition herein comprising (i) an insoluble alpha-glucan and soluble alpha-glucan derivative, or (ii) an insoluble alpha-glucan and additive (e.g., particles of [i] or [ii]) further comprises (e.g., is bound to) at least one cation. Such binding is typically via ionic bonding. Examples of a cation include one or more hard water cations such as $Ca^{2+}$ and/or $Mg^{2+}$. The binding of a composition herein to a cation in an aqueous composition/system can act to soften the water (act as a builder) of the aqueous composition/system. Typically, a composition herein having this applicability comprises particles having a negative surface charge (e.g., insoluble alpha-glucan coated with a negatively charged soluble alpha-glucan derivative such as a carboxymethyl alpha-glucan or alpha-glucan substituted with carboxylic groups).

An aqueous composition/system in which a composition herein can bind to at least one cation can be wash liquor/grey water being used to wash dishware herein (e.g., in an automatic dishwashing machine) or fabric-containing articles herein (e.g., clothes, such as in a laundry machine), or any other aqueous composition/system to which a detergent has been added for washing and/or providing maintenance, for example; such an aqueous composition/system typically can benefit from the ability of a composition herein to prevent/reduce negative effects (e.g., scale deposition and/or scum formation) caused by the presence of one or more cations. In some aspects, an aqueous composition/system in which a composition herein can bind to at least one cation can be any system disclosed herein in which water or an aqueous solution is circulated, transited, and/or stored (a detergent does not necessarily need to be present); such a system typically can also benefit for the same reasons as disclosed above. Typically, a composition in some aspects can act as a builder/softener by sequestering/chelating and/or precipitating cations. The binding (or other interaction, whatever the case may be) between a composition herein with a cation can prevent/reduce formation (e.g., by about, or at least about 10%, 20%, 30%, 40%, 50%, 60%, 70%, or 80%, as compared to not using the composition) of undesired insoluble salts (e.g., carbonates such as $CaCO_3$ or $MgCO_3$, hydroxides such as $Mg(OH)_2$ or $Ca(OH)_2$, sulfates such a $CaSO_4$) and/or other insoluble compounds (e.g., calcium and/or magnesium salts of fatty acids such as stearate), and/or their deposits (e.g., scale, scum such as soap scum) that can form in aqueous systems having hard water cations. In some aspects, scale can comprise $CaCO_3$, $MgCO_3$, $CaSO_4$, $Fe_2O_3$, FeS, and/or $FeS_2$.

In addition to those mentioned above, some examples of aqueous systems herein that can be treated with a composition herein include those of an industrial setting. Examples of industrial settings herein include those of an energy (e.g., fossil fuel such as petroleum or natural gas), water (e.g., water treatment and/or purification, industrial water, wastewater treatment), agriculture (e.g., grain, fruits/vegetables, fishing, aquaculture, dairy, animal farming, timber, plants), chemical (e.g., pharmaceutical, chemical processing), food processing/manufacturing, mining, or transportation (e.g., fresh water and/or maritime shipping, train or truck container) industry. Further examples of aqueous systems herein that can be treated with a composition herein include those for water treatment, water storage, and/or other water-bearing system (e.g., piping/conduits, heat exchangers, condensers, filters/filtration systems, storage tanks, water cooling towers, water cooling systems/apparati, pasteurizers, boilers, sprayers, nozzles, ship hull, ballast water). Further examples of aqueous systems herein that can be treated with a composition herein include those of a medical/dental/healthcare setting (e.g., hospital, clinic, examination room, nursing home), food service setting (e.g., restaurant, commissary kitchen, cafeteria), retail setting (e.g., grocery, soft drink machine/dispenser), hospitality/travel setting (e.g., hotel/motel), sports/recreational setting (e.g., aquatics/tubs, spa), or office/home setting (e.g., bathroom, tub/shower, kitchen, appliances [e.g., laundry machine, automatic dishwashing machine, fridge, freezer], sprinkler system, home/building water piping, water storage tank, water heater). Further examples of aqueous systems herein that can be treated with a composition herein include those as disclosed in any of U.S. Patent Appl. Publ. Nos. 2013/0029884, 2005/0238729, 2010/0298275, 2016/0152495, 2013/0052250, 2015/009891, 2016/0152495, 2017/0044468, 2012/0207699, or 2020/0308592, or U.S. Pat. Nos. 4,552,591, 4,925,582, 6,478,972, 6,514,458, 6,395,189, 7,927,496, or 8784659, which are all incorporated herein by reference. In some aspects, an aqueous system that can be treated herein comprises (i) salt water such as seawater, or (ii) an aqueous solution having about 2.0, 2.25, 2.5, 2.75, 3.0, 3.25, 3.5, 3.75, 4.0, 2.5-4.0, 2.75-4.0, 3.0-4.0, 2.5-3.5, 2.75-3.5, 3.0-3.5, 3.0-4.0, or 3.0-3.5 wt % of one or a combination of salts (e.g., including at least NaCl).

A composition herein comprising (i) an insoluble alpha-glucan and soluble alpha-glucan derivative, or (ii) an insoluble alpha-glucan and additive (e.g., particles of [i] or [ii]) can be a film or coating, for example. A film or coating can be a dried film or coating in some aspects, comprising less than about 3, 2, 1, 0.5, or 0.1 wt % water, for example. In some aspects, a film or coating can comprise about 20-40, 20-35, 20-30, 25-40, 25-35, or 25-30 wt % a composition herein, where the balance of material in the film or coating optionally is water, an aqueous solution, and/or a plasticizer. The amount a composition as presently disclosed in a film or coating herein can be about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, or 99.9 wt %, for example. A film or coating herein can be produced, for example, by providing a layer of an aqueous dispersion/emulsion of particles of the disclosed composition ([i] an insoluble alpha-glucan and soluble alpha-glucan derivative, [ii] an insoluble alpha-glucan and additive) onto a surface/object/material, and then removing all of, or most of (≥90, 95, 98, 99 wt %), the water from the dispersion/emulsion, thereby producing a film or coating. Methodology similar to, or as disclosed in, U.S. Pat. Appl. Publ. No. 2018/0258590 (incorporated herein by reference) can be used to produce a film or coating, for example.

A film or coating herein can have a thickness of about, at least about, or up to about, 0.5, 0.6, 0.7, 0.8, 0.9, 1.0, 1.1, 1.2, 1.3, 1.4, 1.5, 2, 2.5, 5, 7.5, 10, 15.5, 15, 17.5, 20, 22.5, 25, 30, 35, 40, 45, 50, 75, 100, 150, 200, 0.5-1.5, 0.8-1.5, 1.0-1.5, 0.5-1.4, 0.8-1.4, or 1.0-1.4 mil (1 mil=0.001 inch), for instance. In some aspects, such thickness is uniform, which can be characterized by having a contiguous area that (i) is at least 20%, 30%, 40%, or 50% of the total film/coating area, and (ii) has a standard deviation of thickness of less than about 0.06, 0.05, or 0.04 mil. A film or coating herein can be characterized as thin (e.g., <2 mil) in some aspects. A film herein is typically a cast film.

A film or coating herein can exhibit various degrees of transparency as desired. For example, a film/coating can be highly transparent (e.g., high light transmission, and/or low haze). Optical transparency as used herein can, for example, refer to a film or coating allowing at least about 10-99% light transmission, or at least about 50%, 60%, 70%, 80%, 90%, 95%, 96%, 97%, 98%, or 99% light transmission, and/or less than 30%, 25%, 20%, 15%, 10%, 5%, 2.5%, 2%, or 1% haze. High optical transparency can optionally refer to a film/coating having at least about 90% light transmittance and/or a haziness of less than 10%. Light transmittance of a film/coating herein can be measured following test ASTM D1746 (2009, Standard Test Method for Transparency of Plastic Sheeting, ASTM International, West Conshohocken, PA), for example, which is incorporated herein by reference. Haze of a film/coating herein can be measured following test ASTM D1003-13 (2013, Standard Test Method for Haze and Luminous Transmittance of Transparent Plastics, ASTM International, West Conshohocken, PA), for example, which is incorporated herein by reference.

A film or coating herein can optionally further comprise a plasticizer such as glycerol, propylene glycol, ethylene glycol, and/or polyethylene glycol. In some aspects, other film components (in addition to a composition herein) can be as disclosed in U.S. patent. Appl. Publ. No. 2011/0151224, 2015/0191550, or 20190153674, U.S. Pat. No. 9,688,035 or 3,345,200, or International Patent Appl. Publ. No. WO2018/200437, all of which are incorporated herein by reference.

A film or coating, or any suitable solid composition herein (e.g., composite), in some aspects can further comprise at least one crosslinking agent. Particles of the present disclosure can be crosslinked (covalently) to each other and/or to at least one other component (e.g., polymer, active agent) of the composition, or to a component of a substrate if the composition is applied to the substrate. Yet, in some aspects, particles herein are not crosslinked in any manner, but one or more other components of the composition are crosslinked. Crosslinking can (i) enhance the tensile strength of, and/or (ii) plasticize, a film or coating composition, for example. Crosslinking can link a film or coating to a substrate in some aspects. In some cases, a crosslinking agent such as a di- or poly-carboxylic acid, aldehyde, or polyphenol can be used to impart both plasticity and linking-to-substrate features. Suitable crosslinking agents for preparing a composition herein with crosslinking as above are contemplated to include phosphoryl chloride ($POCl_3$), polyphosphate, sodium trimetaphosphate (STMP), boron-containing compounds (e.g., boric acid, diborates, tetraborates such as tetraborate decahydrate, pentaborates, polymeric compounds such as PolyborS, alkali borates), polyvalent metals (e.g., titanium-containing compounds such as titanium ammonium lactate, titanium triethanolamine, titanium acetylacetonate, or polyhydroxy complexes of titanium; zirconium-containing compounds such as zirconium lactate, zirconium carbonate, zirconium acetylacetonate, zirconium triethanolamine, zirconium diisopropylamine lactate, or polyhydroxy complexes of zirconium), glyoxal, glutaraldehyde, aldehyde, polyphenol, divinyl sulfone, epichlorohydrin, polyamide-epichlorohydrin (PAE), di- or poly-carboxylic acids (e.g., citric acid, malic acid, tartaric acid, succinic acid, glutaric acid, adipic acid), dichloro acetic acid, polyamines, and diglycidyl ether (e.g., diglycidyl ether itself, diethylene glycol dimethyl ether [diglyme], ethylene glycol diglycidyl ether [EGDE], 1,4-butanediol diglycidyl ether [BDDGE], polyethylene glycol diglycidyl ether [PEGDE, such as PEG2000DGE], bisphenol A diglycidyl ether [BADGE]). Still other examples of suitable crosslinking agents are described in U.S. Pat. Nos. 4,462,917, 4,464,270, 4,477,360 and 4,799,550, and U.S. Patent Appl. Publ. No. 2008/0112907, which are all incorporated herein by reference. Yet, in some aspects, a crosslinking agent is not a boron-containing compound (e.g., as described above). Particles herein can be crosslinked, such as with any crosslinker as presently disclosed, in other contexts besides a film or coating (e.g., in a dispersion or other composition disclosed herein).

One or more conditioning agents can be comprised in a film of coating, for example, to enhance the haptics of the film or coating. A conditioning agent can be an anionic softener such as sulphated oil, soap, sulphated alcohol, and/or oil emulsion; a cationic softener such as a quaternary ammonium compound; a nonionic softener such as a polyoxyethylene derivative, polyethylene emulsion, wax emulsion, and/or silicon softener; natural fatty acid; oil; monoglyceride; diglyceride; polyglyceride; citric acid ester; lactic acid ester; and/or sugar ester such as a sucrose ester and/or sorbitan ester.

Also disclosed are articles comprising an adhesive, film, coating, or binder comprising particles herein in a dry form. Such articles (optionally, "coated articles") comprise a substrate having at least one surface on which is disposed/deposited the coating, adhesive, film, or binder, in a substantially continuous or discontinuous manner. In some aspects, an article comprises paper, leather, wood, metal, polymer, fibrous material, masonry, drywall, plaster, and/or an architectural surface. An "architectural surface" herein is an external or internal surface of a building or other man-made structure. In some aspects, an article comprises a porous substrate such as in paper, cardboard, paperboard, corrugated board, a cellulosic substrate, a textile, or leather. Yet, in some aspects, an article can comprise a polymer such as polyamide, polyolefin, polylactic acid, polyethylene terephthalate (PET), poly(trimethylene terephthalate) (PTT), aramid, polyethylene sulfide (PES), polyphenylene sulfide (PPS), polyimide (PI), polyethylene imine (PEI), polyethylene naphthalate (PEN), polysulfone (PS), polyether ether ketone (PEEK), polyethylene, polypropylene, poly(cyclic olefins), poly(cyclohexylene dimethylene terephthalate), poly(trimethylene furandicarboxylate) (PTF), or cellophane. In some aspects, an article comprising a fibrous substrate is a fiber, yarn, fabric, fabric blend, textile, non-woven, paper, or carpet. A fibrous substrate can contain natural and/or synthetic fibers, such as cotton, cellulose, wool, silk, rayon, nylon, aramid, acetate, polyurethane urea, acrylic, jute, sisal, sea grass, coir, polyamide, polyester, polyolefin, polyacrylonitrile, polypropylene, polyaramid, or blends thereof.

A film, coating, or other composition (e.g. composite) herein can have grease/oil and/or oxygen barrier properties in some aspects. Such a composition can comprise, along with particles herein, one or more components as disclosed in U.S. patent. Appl. Publ. No. or International Patent Appl. Publ. No. WO2018/200437, which are each incorporated herein by reference. For example, a film, coating, or other composition herein can comprise, optionally as a binder, one or more of polyvinyl alcohol, polyvinyl acetate, partially saponified polyvinyl acetate, silanol-modified polyvinyl alcohol, butenediol vinyl alcohol co-polymer (BVOH), polyurethane, starch, corn dextrin, carboxymethyl cellulose, cellulose ethers, hydroxyethyl cellulose, hydroxypropyl cellulose, ethyl hydroxyethyl cellulose, methyl cellulose, alginates, sodium alginate, xanthan, carrageenan, casein, soy protein, guar gums, synthetic polymers, styrene butadiene latex, and/or styrene acrylate latex. A composition for preparing a film, coating, or other composition in some aspects can comprise about 50, 55, 60, 65, 70, 75, 80, 85, 90, 95, 65-85, 65-80, 70-85, or 70-80 wt % of a binder or compound such as polyvinyl alcohol (or any other of the above-referenced compounds), and about 50, 45, 40, 35, 30, 25, 20, 15, 10, 5, 2.5, 15-35, 20-35, 15-30, or 20-30 wt % particles as presently disclosed. In some aspects, a composition for preparing a film, coating, or other composition can comprise a ratio of binder or compound (e.g., any of the above-referenced compounds such as polyvinyl alcohol or starch) to particles herein of about 7:3, 7.5:2.5, 8:2, 8.5:1.5, or 9:1, based on the wt % of each of these components in the composition. In some aspects, a film, coating, or other composition does not comprise starch, while in other aspects such as an oxygen barrier, starch can be included (e.g., as disclosed in U.S. Patent Appl. Publ. No. 2011/0135912 or U.S. Pat. No. 5,621,026 or 6,692,801, which are incorporated herein by reference). Grease/oil barrier properties of a coating or film composition herein can be evaluated using a standard "KIT" type test following Technical Association of the Pulp and Paper Industry (TAPPI) Test Method T-559 cm-02 (Grease resistance test for paper and paperboard, TAPPI Press, Atlanta, GA, USA; incorporated herein by reference), for example. Good grease/oil barrier/resistance function is indicated in this test by values closer to 12 on a scale of 1 to 12. Grease/oil barrier properties, as well as water/aqueous liquid barrier properties, can be evaluated by a Cobb test, if desired. A barrier herein can have a Cobb index value of less than 20, 17.5, 15, 12.5, 10, 7.5, or 5, for example. Oxygen barrier properties of a coating or film composition herein can be evaluated by measuring the oxygen transmission rate (OTR) of the coating; OTR can be determined, for example, according to ASTM F-1927-07 (2007, Standard Test Method for Determination of Oxygen Gas Transmission Rate, Permeability and Permeance at Controlled Relative Humidity Through Barrier Materials Using a Coulometric Detector, ASTM International, West Conshohocken, PA), which is incorporated herein by reference. OTR can be determined under relative humidity conditions of about 50%-80%, 30%-55%, 35%-50%, or 30%-80%, and/or a temperature of about, or at least about, 15, 20, 25, 30, 35, 40, 45, 15-40, 15-35, 15-30, 15-25, 20-40, 20-35, 20-30, or 20-25° C., for example. Examples of substrates herein that can take advantage of a grease/oil and/or oxygen barrier coating include any of the foregoing substrates/surfaces, including a substrate comprising cellulose (e.g., paper, paperboard, cardboard, corrugated board, textile), polyethylene, polypropylene, poly lactic acid, poly(ethylene terephthalate) (e.g., MYLAR), poly(trimethylene terephthalate), polyamide, polybutylene succinate, polybutylene adipate terephthalate, polybutylene succinate adipate, poly(trimethylene furandicarboxylate), a synthetic and/or petrol-based substrate, or a bio-based substrate. Any of the foregoing film, coating, or other compositions can be in the form of a laminate or extruded product, for example, and that is optionally situated on any of the foregoing substrates.

A film, coating, or other composition (e.g., dispersion, foam, masterbatch, composite) comprising particles herein can further comprise polyurethane (e.g., any as disclosed herein) in some aspects. Such a composition can comprise about 1, 5, 10, 15, 20, 35, 30, 35, 40, 45, 50, 55, 60, 5-60, 5-50, 5-45, 5-40, 5-35, 5-30, 10-60, 10-50, 10-45, 10-40, 10-35, or 10-30 wt % of particles herein, for example; the balance can be comprised all or mostly of (e.g., be over 90% or 95% of) one or more polyurethanes. Such a composition can be wet (e.g., a dispersion of particles and polyurethane) or dry (e.g., a masterbatch, film/coating, laminate, foam, or extruded composite of particles and polyurethane). A polyurethane herein can be of a molecular weight that is about, or at least about, 1000, 1500, 2000, 2500, 3000, 3500, 4000, 1000-3000, 1500-3000, 1000-2500, or 1500-2500, for example. Such a composition can, in some instances, be hydrolytically aged (e.g., exposed to 45-55 or ~50° C., and/or 90-98% or ~95% relative humidity, for a period of 2-4 or 3 days). In some aspects, a polyurethane composition with particles herein can be heat- and/or pressure-processable; application of heat and/or pressure for pressing, molding, extruding, or any other related processing step can be at about, or at least about, 90, 95, 100, 105, 110, 115, 120, 130, 140, 95-115, or 100-110° C., and/or at a pressure of at least about 5000, 10000, 15000, 20000, or 25000 psi, for example. Such application of heat and/or pressure can be for a time of at least about 1, 2, 3, 4, 5, 6, 7, 8, 9, 10, 15, or 30 minutes, for example. A pressed polyurethane composition in some aspects such as a film can be about, or at least about, 70%, 75%, 80%, 85%, 90%, 95%, 98%, 99%, or 100% transparent or translucent. In some aspects, any polyurethane composition presently disclosed can be made by a process that comprises providing an aqueous polyurethane dispersion, and mixing particles herein with the polyurethane dispersion (e.g., by adding an aqueous dispersion of the glucan particles). The resulting aqueous dispersion can be used directly to make a composition (e.g., a film or coating), or it can be dried to a masterbatch that is then used to prepare a composition (e.g., by melt-processing).

A film or coating in some aspects can be in the form of an edible film or coating. Such a material can, in some aspects, comprise particles herein and one or more components as described in U.S. Pat. Nos. 4,710,228, 4,543,370, 4,820,533, 4,981,707, 5,470,581, 5,997,918, 8,206,765, or 8999413, or U.S. Patent Appl. Publ. No. 2005/0214414, which are incorporated herein by reference. In some aspects, particles herein replace starch and/or starch derivatives in an edible film or coating, optionally as disclosed in any of the foregoing references. An edible film or coating can be on potato products (e.g., potato strips such as French fries), other vegetables or vegetable products (e.g., zucchini, squash, sweet potatoes, onions, okra, peppers, string beans, tomatoes, cucumbers, lettuce, cabbage, carrots, broccoli, cauliflower, brussels sprouts, bean sprouts, onions, any fresh cut version of a vegetable), mushrooms, fruits (e.g., berries such as raspberries, strawberries, or blue berries, avocados, kiwis, kumquats, oranges, tangerines, apples, pears, bananas, grapefruit, cherries, *papaya*, lemons, limes, mangos, peaches, cantaloupe, any fresh cut version of a fruit), and/or nuts (peanuts, walnuts, almonds, pecans, cashews, filberts/hazel nuts, Brazil nuts, macadamias), for example. Any other food disclosed herein, as appropriate, can have an edible coating, for example. These and other food products having an edible film or coating herein can be fried or baked in some aspects, and/or the film or coating provides tenderness, moisture retention, protection from moisture, crispness, dietary fiber (in place of digestible starch), oxygen barrier, freshness, and/or anti-ripening. Anti-ripening in some aspects can be measured by the degree to which a coating lowers (e.g., by at least 25%, 50%, 75%, 80%, 85%, or 90%) the emission of a gaseous ripening hormone, such as ethylene, by a plant-based product (e.g., at 15-30, 15-25, or 20-25° C.), and/or by the degree to which plant product softening and/or sweetening is decreased by a coating. An edible coating in some aspects can be prepared by applying an aqueous dispersion comprising particles herein (e.g., at 5-15, 5-12, 5-10, 7.5-15, 7.5-12, or 7.5-10 wt % in water or aqueous solution) to a food product and drying the dispersion (e.g., by air drying, forced air drying, vacuum drying, and/or heating).

A coating composition in some aspects, which can be used to prepare a coating herein, can comprise any of the foregoing components/ingredients/formulations. In some aspects, a coating composition is a latex composition, such as described below.

A composition herein comprising (i) an insoluble alpha-glucan and soluble alpha-glucan derivative, or (ii) an insoluble alpha-glucan and additive (e.g., particles of [i] or [ii]) can be a latex composition in some aspects. Examples of latex compositions herein include paint (e.g., primer, finishing/decorative), adhesives, films, coatings, and binders. Formulations and/or components (in addition to a composition herein) of a latex composition herein can be as described in, for example, U.S. Pat. Nos. 6,881,782, 3,440,199, 3,294,709, 5,312,863, 4,069,186, or 6297296, or U.S. Patent Appl. Publ. No. 2020/0263026, which are all incorporated herein by reference.

A composition as presently disclosed can be present in a latex composition in any useful amount, such as at about, or at least about, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 40%, 45%, 50%, 55%, 60%, 65%, 70%, 75%, 0.01%-75% 0.01%-5%, 5%-20%, 20%-50%, or 50%-75% based on the weight of all the dispersed solids of the latex.

A latex composition in some aspects can comprise a polymer polymerized from at least one ethylenically unsaturated monomer (e.g., monoethylenically unsaturated monomer); polyurethane; epoxy, and/or a rubber elastomer. Examples of monoethylenically unsaturated monomers herein include vinyl monomers, acrylic monomers, allylic monomers, acrylamide monomers, monocarboxylic unsaturated acids and dicarboxylic unsaturated acids.

Examples of suitable vinyl monomers of a polymer in a latex composition herein include any compound having vinyl functionality (i.e., ethylenic unsaturation) such as vinyl esters (e.g., vinyl acetate, vinyl propionate, vinyl laurate, vinyl pivalate, vinyl nonanoate, vinyl decanoate, vinyl neodecanoate, vinyl butyrates, vinyl benzoates, vinyl isopropyl acetates), vinyl aromatic hydrocarbons (e.g., styrene, methyl styrenes and similar lower alkyl styrenes, chlorostyrene, vinyl toluene, vinyl naphthalene, divinyl benzene), vinyl aliphatic hydrocarbons (e.g., vinyl chloride; vinylidene chloride; alpha olefins such as ethylene, propylene and isobutylene; conjugated dienes such as 1,3-butadiene, methyl-2-butadiene, 1,3-piperylene, 2,3-dimethyl butadiene, isoprene, cyclohexene, cyclopentadiene, and dicyclopentadiene) and vinyl alkyl ethers (e.g., methyl vinyl ether, isopropyl vinyl ether, n-butyl vinyl ether, isobutyl vinyl ether), but excluding compounds having acrylic functionality (e.g., acrylic acid, methacrylic acid, esters of such acids, acrylonitrile, acrylamides). In some aspects, a latex composition herein comprises a vinyl acetate-ethylene copolymer, carboxylated vinyl acetate-ethylene copolymer, and/or or polyvinyl acetate.

Examples of suitable acrylic monomers of a polymer in a latex composition herein include alkyl acrylates, alkyl methacrylates, acrylate acids, methacrylate acids, aromatic derivatives of acrylic and methacrylic acid, acrylamides, and acrylonitrile. Typically, alkyl acrylate and methacrylic monomers (also referred to as alkyl esters of acrylic or methacrylic acid) have an alkyl ester portion containing from 1 to about 18 carbon atoms per molecule, or from 1 to about 8 carbon atoms per molecule. Suitable acrylic monomers include, for example, methyl acrylate and methacrylate, ethyl acrylate and methacrylate, butyl acrylate and methacrylate, propyl acrylate and methacrylate, 2-ethyl hexyl acrylate and methacrylate, cyclohexyl acrylate and methacrylate, decyl acrylate and methacrylate, isodecyl acrylate and methacrylate, benzyl acrylate and methacrylate, isobornyl acrylate and methacrylate, neopentyl acrylate and methacrylate, and 1-adamantyl methacrylate. If acid functionality is desired, acids such as acrylic acid or methacrylic acid can also be used.

A latex composition in some aspects comprises a polyurethane polymer. Examples of suitable polyurethane polymers are those comprising polysaccharides as disclosed in U.S. Patent Appl. Publ. No. 2019/0225737, which is incorporated herein by reference. A latex comprising a polyurethane can be prepared, for example, as disclosed in U.S.

Patent Appl. Publ. No. 2016/0347978, which is incorporated herein by reference, and/or comprise the reaction product of one or more polyisocyanates with one or more polyols. Useful polyols include polycarbonate polyols, polyester polyols and polyether polyols, for example. Polycarbonate polyurethane herein can be formed as the reaction product of a polyol such as 1,3-propanediol, 1,4-butanediol, 1,6-hexanediol, diethylene glycol, or tetraethylene glycol, with a diaryl carbonate such as diphenyl carbonate or phosgene. At least one polyisocyanate herein can be an aliphatic polyisocyanate, aromatic polyisocyanate, or polyisocyanate that has both aromatic and aliphatic groups. Examples of polyisocyanates include 1,6-hexamethylene diisocyanate, isophorone diisocyanate, 2,4-toluene diisocyanate, 2,6-toluene diisocyanate, mixtures of 2,4- and 2,6-toluene diisocyanate, bis(4-isocyanatocyclohexyl) methane, 1,3-bis(1-isocyanato-1-methylethyl)benzene, bis(4-isocyanatophenyl) methane, 2,4'-diphenylmethane diisocyanate, 2,2'-diphenylmethane diisocyanate, 2,4-diisocyanatotoluene, bis (3-isocyanatophenyl)methane, 1,4-diisocyanatobenzene, 1,3-diisocyanato-o-xylene, 1,3-diisocyanato-p-xylene, 1,3-diisocyanato-m-xylene, 2,4-diisocyanato-1-chlorobenzene, 2,4-diisocyanato-1-nitrobenzene, 2,5-diisocyanato-1-nitrobenzene, m-phenylene diisocyanate, hexahydrotoluene diisocyanate, 1,5-naphthalene diisocyanate, 1-methoxy-2,4-phenylene diisocyanate, 4,4'-biphenylmethane diisocyanate, 4,4'-biphenylene diisocyanate, 3,3'-dimethyl-4,4'-diphenylmethane, diisocyanate, 3,3'-4,4'-diphenylmethane diisocyanate, and 3,3'-dimethyldiphenylmethane-4,4'-diisocyanate. Also useful herein are polyisocyanate homopolymers comprising allophanate, biuret, isocyanurate, iminooxadiazinedione, or carbodiimide groups, for example. A polyol herein can be any polyol comprising two or more hydroxyl groups, for example, a C2 to C12 alkane diol, ethylene glycol, 1,2-propylene glycol, 1,3-propylene glycol, isomers of butane diol, pentane diol, hexane diol, heptane diol, octane diol, nonane diol, decane diol, undecane diol, dodecane diol, 2-methyl-1,3-propane diol, 2,2-dimethyl-1,3-propane diol (neopentyl glycol), 1,4-bis(hydroxymethyl)cyclohexane, 1,2,3-propane triol (glycerol), 2-hydroxymethyl-2-methyl-1,3-propanol (trimethylolethane), 2-ethyl-2-hydroxymethyl-1,3-propanediol (trimethylolpropane), 2,2-bis(hydroxymethyl)-1,3-propane diol (pentaerythritol); 1,4, 6-octanetriol; chloropentanediol; glycerol monoalkyl ether; glycerol monoethyl ether; diethylene glycol; 1,3,6-hexanetriol; 2-methylpropanediol; 2,2,4-trimethyl-1,3-pentanediol, cyclohexanedimethanol, polymeric polyols, for example, polyether polyols or polyester polyols. In some aspects, a polyol herein can be poly(oxytetramethylene) glycol, polyethylene glycol, or poly 1,3-propane diol. A polyol in some aspects can be polyester polyol, such as one produced by transesterification of aliphatic diacids with aliphatic diols. Suitable aliphatic diacids include, for example, C3 to C10 diacids, malonic acid, succinic acid, glutaric acid, adipic acid, pimelic acid, suberic acid, azelic acid, sebacic acid. In some aspects, aromatic and/or unsaturated diacids can be used to form a polyester polyol.

A latex composition in some aspects comprises an epoxy polymer/resin (polyepoxide), such as bisphenol A epoxy resin, bisphenol F epoxy resin, Novolac epoxy resin, aliphatic epoxy resin, or glycidylamine epoxy resin.

A latex composition in some aspects comprises a rubber elastomer. In some aspects, a rubber elastomer can include one or more diene-based sulfur-vulcanizable elastomers having a glass transition temperature (Tg) below −30° C., as determined, for example, by dynamic mechanical analysis. In further examples, a rubber elastomer herein includes natural rubber, synthetic polyisoprene, polybutadiene rubber, styrene/butadiene copolymer rubber, ethylene propylene diene monomer rubber, hydrogenated nitrile butadiene rubber, neoprene, styrene/isoprene/butadiene terpolymer rubber, butadiene/acrylonitrile rubber, polyisoprene rubber, isoprene/butadiene copolymer rubber, nitrile rubber, ethylene-acrylic rubber, butyl and halobutyl rubber, chlorosulfonated polyethylene, fluoroelastomer, hydrocarbon rubber, polybutadiene, or silicone rubber.

The liquid component of a latex composition herein can be water or an aqueous solution. An aqueous solution of a latex in some aspects can comprise an organic solvent that is either miscible or immiscible with water. Suitable organic solvents herein include acetone, methyl ethyl ketone, butyl acetate, tetrahydrofuran, methanol, ethanol, isopropanol, diethyl ether, glycerol ethers, hexane, toluene, dimethyl acetamide, dimethylformamide, and dimethyl sulfoxide.

A latex composition herein can further comprise one or more additives in some aspects. Examples of additives herein include dispersants, rheological aids, antifoams, foaming agents, adhesion promoters, flame retardants, bactericides, fungicides, preservatives, optical brighteners, fillers, anti-settling agents, coalescing agents, humectants, buffers, pigments/colorants (e.g., metallic oxides, synthetic organic pigments, carbon black), viscosity modifiers, antifreeze, surfactants, binders, crosslinking agents, anticorrosion agents, hardeners, pH regulators, salts, thickeners, plasticizers, stabilizers, extenders, and matting agents. Examples of pigments herein include titanium dioxide ($TiO_2$), calcium carbonate, diatomaceous earth, mica, hydrated aluminum oxide, barium sulfate, calcium silicate, clay, silica, talc, zinc oxide, aluminum silicate, nepheline syenite, and mixtures thereof. In some aspects, a latex composition is essentially free from (e.g., less than 1, 0.5, 0.1, or 0.01 wt % of component) starch, starch derivative (e.g., hydroxyalkyl starch), cellulose, and/or cellulose derivative (e.g., carboxymethyl cellulose).

A latex composition in the form of a paint or other coloring agent herein can have a pigment volume concentration (PVC) of about 3% to about 80% in some aspects. As examples, a flat paint can have a PVC in the range of about 55-80%, a primer or undercoat can have a PVC in the range of about 30-50%, and/or a gloss colored paint can have a PVC in the range of about 3-20%. A paint or other coloring agent in some aspects can have a PVC of about 55%, 60%, 65%, 70%, 75%, 80%, 55-80%, 55-75%, 55-70%, 60-80%, 60-75%, 60-70%, 63-67%, 64-66%, 65-80%, 65-75%, or 65-70%. A PVC value herein can be that of a particular pigment (or mix of pigments) such as those disclosed above (e.g., titanium dioxide), for instance. A composition of the present disclosure is believed to provide one or more physical properties to a latex composition (e.g., for use as a paint or other coloring agent): opacity, less pigment needed, increased hardness, reduced tackiness, decreased gloss (i.e., providing a matte effect), increased shear strength, better abrasion resistance, improved dry time, improved fade resistance, lower blistering, and/or improved hand (a less tacky feel), for example, as compared to a latex composition that only differs by not comprising the disclosed composition.

A latex composition herein can be applied to the substrate of an article (above) using any method known in the art. Typically, after application of the latex composition, at least a portion of the aqueous solution is removed, for example by drying, to provide an adhesive, film, coating, or binder comprising the latex composition in a dry or semi-dry form. Suitable application methods include air knife coating, rod coating, bar coating, wire bar coating, spray coating, brush coating, cast coating, flexible blade coating, gravure coating, jet applicator coating, short dwell coating, slide hopper coating, curtain coating, flexographic coating, size-press coating, reverse roll coating, and transfer roll coating. A latex composition can be applied on at least a portion of a substrate, and can be in one or more coats/applications, for example.

Some aspects herein are drawn to a pigment-comprising composition. A pigment-comprising composition can be in a liquid form (e.g., an aqueous or non-aqueous composition herein) or solid form (e.g., a dry composition herein). Examples of a pigment-comprising composition herein include any of such compositions disclosed elsewhere herein (e.g., paint, primer, stain), ink, dye (e.g., food-coloring dye, fabric-coloring dye), resin, sunscreen, and cosmetics (e.g., mascara, blush, nail varnish/polish, lipstick, gloss, eyeliner, foundation, eye shadow, skin decoration composition). A pigment in a pigment-comprising composition can be any pigment herein, for example. Examples of a pigment for these and/or other aspects herein include oxides of titanium (e.g., titanium dioxide), zinc, iron, zirconium, cerium, and chromium; manganese violet; ultramarine blue; chromium hydrate; Prussian Blue; zinc sulfide; nitroso, nitro, azo, xanthene, quinoline, anthraquinone and/or phthalocyanine compounds; metal complex compounds; and isoindolinone, isoindoline, quinacridone, perinone, perylene, diketopyrrolopyrrole, thioindigo, dioxazine, triphenylmethane and/or quinophthalone compounds. Further pigment examples useful herein are disclosed in U.S. patent. Appl. Publ. No. 2006/0085924, which is incorporated herein by reference.

A composition herein comprising (i) an insoluble alpha-glucan and soluble alpha-glucan derivative, or (ii) an insoluble alpha-glucan and additive (e.g., particles of [i] or [ii]) can be in the form of a composite (e.g., rubber composite or polyurethane composite) such as disclosed in U.S. Patent Appl. Publ. Nos. 2019/0225737, 2017/0362345, or 2020/0181370, all of which are incorporated herein by reference. It can optionally be stated that a composite as presently disclosed comprises at least one polymer in addition to a composition of the disclosure. One or more of the above components (e.g., a rubber or polyurethane) of a latex composition can optionally be an additional polymer in such a composite. An additional polymer of a composite herein can be rubber, polyurethane, thermoplastic polymer, polyethylene, polypropylene, ethylene copolymer, polyvinyl butyrate, polylactic acid, polyvinyl alcohol, polyamide, polyether thermoplastic elastomer, polyester, polyether ester, ethylene vinyl alcohol copolymer, starch, cellulose, or any suitable polymer as disclosed above for latex components.

Rubber in some aspects can be one or more of natural rubber, synthetic rubber, polyisoprene, polybutadiene, styrene-butadiene copolymer, styrene-isoprene copolymer, butadiene-isoprene copolymer, styrene-butadiene-isoprene terpolymer, ethylene propylene diene monomer rubber, hydrogenated nitrile butadiene rubber, silicone rubber, or neoprene, for instance. Examples of composites herein comprising rubber include tires (e.g., auto/bicycle; pneumatic tire; including tire treads and/or sidewalls), belts (e.g., conveyor belts, power transmission belts), hoses, gaskets, footwear (e.g., shoes, sneakers, boots; soles, cushioning, and/or aesthetic features), coatings, films, and adhesives. Rubber composites herein typically are vulcanized. It is contemplated that, in some aspects, inclusion of a composition herein in a composite comprising rubber can provide advantages such as lower cost, lower density, lower energy consumption during processing, and/or better or equal performance as compared to use of an incumbent filler such as carbon black or silica (e.g., increased wet traction, reduced rolling resistance, lighter weight, and/or mechanical strength); such performance enhancements can be with tires in some aspects. In some aspects, a composition herein replaces about, or at least about, 25, 30, 35, 40, 45, 50, 55, 60, 65, 70, 75, 80, 85, 90, 95, or 100 wt % of an incumbent filler (e.g., carbon black, or silica) that is typically used in a rubber composite such as a tire. It is noted that rubber composite tires currently on the market (that do not comprise a composition herein) typically comprise up to about 30 wt % of an incumbent filler such as carbon black. Thus, a rubber composite herein such as a tire can comprise about, or at least about, 5, 10, 15, 20, 25, or 30 wt % a composition as presently disclosed, for example. A rubber composition herein can have a low minimum elastic torque ($M_L$) (e.g., less than, or about, 0.10, 0.08, 0.06, 0.04, 0.03, or 0.02 dNm [deciNewton-meter]) in some aspects, and so a method of mixing a rubber composition during its preparation is disclosed.

Non-limiting examples of compositions and methods disclosed herein include:

1. A composition comprising insoluble alpha-glucan and a soluble alpha-glucan derivative, wherein at least about 50% of the glycosidic linkages of the insoluble alpha-glucan are alpha-1,3 glycosidic linkages, and the weight-average degree of polymerization (DPw) of the insoluble alpha-glucan is at least 15 (or at least 10), wherein at least about 50% of the glycosidic linkages of the soluble alpha-glucan derivative are alpha-1,3 glycosidic linkages, and the DPw of the alpha-glucan portion of the soluble alpha-glucan derivative is at least 15 (or at least 10).
2. The composition of embodiment 1, 16, 17, or 18, wherein at least about 90% of the glycosidic linkages of the insoluble alpha-glucan are alpha-1,3 glycosidic linkages, and/or wherein at least about 90% of the glycosidic linkages of the soluble alpha-glucan derivative are alpha-1,3 glycosidic linkages.
3. The composition of embodiment 1, 2, 16, 17, or 18, wherein the insoluble alpha-glucan: (i) has a DPw over 100, (ii) is in the form of fibrids, or (iii) has a DPw of about 15 to and/or is in the form of particles having a degree of crystallinity of at least about 0.65.
4. The composition of embodiment 1, 2, or 3, wherein the soluble alpha-glucan derivative has a degree of substitution (DoS) up to about 3.0 with at least one organic group that has a positive charge or a negative charge.
5. The composition of embodiment 4, wherein the DoS with the organic group is at least about 0.3.
6. The composition of embodiment 4 or 5, wherein the organic group is in ether linkage to the soluble alpha-glucan derivative.
7. The composition of embodiment 1, 2, 3, 4, 5, or 6, wherein the insoluble alpha-glucan is coated by the soluble alpha-glucan derivative, optionally wherein the composition comprises particles of the insoluble alpha-glucan coated by the soluble alpha-glucan derivative.
8. The composition of embodiment 7, wherein the composition comprises the particles, and the particles have a negative surface charge or positive surface charge.
9. The composition of embodiment 1, 2, 3, 4, 5, 6, 7, or 8, wherein the composition further comprises an additive that does not chemically react with insoluble alpha-glucan or the soluble alpha-glucan derivative.
10. The composition of embodiment 1, 2, 3, 4, 5, 6, 7, 8, 9, 16, 17, or 18, wherein the composition is in the form of a dispersion, wet cake or wet powder, dry powder, extrusion, composite, film/coating, or encapsulant.

11. The composition of embodiment 1, 2, 3, 4, 5, 6, 7, 8, 9, or 10, comprising about 0.1 to about 50 wt % (or about 1 to about 30 wt %) of the soluble alpha-glucan derivative, wherein the wt % is based on the weight of the insoluble alpha-glucan in the composition.
12. A method of producing a composition according to embodiment 1, 2, 3, 4, 5, 6, 7, 8, 9, 10, or 11, the method comprising: (a) blending together at least water, the insoluble alpha-glucan, and the soluble alpha-glucan derivative (in a suitable container) to provide a blended product, and (b) optionally drying the blended product.
13. The method of embodiment 12, wherein: step (a) is performed by blending (i) a dry powder of the soluble alpha-glucan derivative and (ii) a composition comprising about 10 to 80 wt % of the insoluble alpha-glucan and a balance of water or aqueous solution up to 100 wt %; or step (a) is performed by blending (i) a dry powder of the soluble alpha-glucan derivative, (ii) a composition comprising about 10 to 80 wt % of the insoluble alpha-glucan and a balance of water or aqueous solution up to 100 wt %, and (iii) water or aqueous solution, wherein the total solids of the blended product is about 1 to 30 wt %.
14. A method of producing a composition (e.g., according to embodiment 17 or 18) comprising at least insoluble alpha-glucan and an additive, the method comprising: (a) blending (i) an additive and (ii) a composition comprising about 10 to 80 wt % (or 5 to 80 wt %) of insoluble alpha-glucan and a balance of water or aqueous solution up to 100 wt %, thereby providing a blended product, optionally wherein the mass of the additive is within about 25% of the mass of the water or aqueous solution (and optionally wherein the additive does not chemically react with insoluble alpha-glucan), and wherein at least about 50% of the glycosidic linkages of the insoluble alpha-glucan are alpha-1,3 glycosidic linkages, and the weight-average degree of polymerization (DPw) of the insoluble alpha-glucan is at least (or at least 10), and (b) drying the blended product, wherein most of (e.g., ≥90 wt %), or all of, the water that was present in the composition of (ii) is replaced with the additive.
15. The method of embodiment 14, wherein the additive comprises a non-aqueous liquid.
16. A composition produced by the method of embodiment 14 or 15.
17. A composition comprising insoluble alpha-glucan that is coated by at least one additive (optionally wherein the additive does not chemically react with the insoluble alpha-glucan), wherein at least about 50% of the glycosidic linkages of the insoluble alpha-glucan are alpha-1,3 glycosidic linkages, and the weight-average degree of polymerization (DPw) of the insoluble alpha-glucan is at least 15 (or at least 10).
18. The composition of embodiment 16 or 17, wherein the composition comprises particles of the insoluble alpha-glucan coated by the additive.
19. The composition of embodiment 17 or 18, wherein the additive comprises a non-aqueous liquid.
20. The composition of embodiment 1, 2, 3, 4, 5, 6, 7, 8, 9, 10, 11, 16, 17, 18, or 19, wherein the composition is a household care product, personal care product, industrial product, ingestible product (e.g., food product), medical product, or pharmaceutical product.
21. The composition of embodiment 1, 2, 3, 4, 5, 6, 7, 8, 9, 10, 11, 16, 17, 18, 19, or 20, wherein the composition is an aqueous composition.

EXAMPLES

The present disclosure is further exemplified in the following Examples. It should be understood that these Examples, while indicating certain aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Materials/Methods

Representative Solid State Method to Surface-Exchange Insoluble Alpha-Glucan

Starting materials: Alpha-1,3-glucan wet cake (10-80 wt % solids) (e.g., DPw ~800, ~100% alpha-1,3 linkages, dispersion particle size $D_{50}$ 1-20 microns [i.e., particle size when dispersed in water]; the glucan was "never-dried", meaning that the glucan had never been dried since its enzymatic synthesis with glucansucrase) and surface-modifier dry powder (e.g., a water-soluble alpha-1,3-glucan derivative). When the wet cake and dry powder are blended, the total solids should be between 10-80 wt/o (preferably between 30-70 wt %).

Blending ratio: Addition of the dry powder, relative to the mass (dry weight basis) of the wet cake, can be from 0.1-50 wt % (preferably between 1-30 wt %).

Surface-exchange (surface modification) process: Apply shear to the blended mix using a extruder type device. Multiple passes can be used ranging from 1-20 (preferably between 1-10).

Final product form: The product can be a wet cake, dried (e.g., 80° C., 24 hours) to a dry powder, and/or dispersed (e.g., aqueous dispersion).

Representative Dispersion Method to Surface-Exchange Insoluble Alpha-Glucan

Starting materials and blending ratio: Same as for solid state method (above).

Surface modification process: Add starting materials, and then add water to render the total solids in the range of 1-30 wt/o (preferably between 2-20 wt %). Use a high shear mixer (e.g., Waring® blender, inline rotor stator, inline pressure homogenizer) to apply shear. For batch-time or continuous-passes, apply shear until change in properties such as surface zeta potential, dispersion viscosity, etc., is/are observed.

Final product form: The product can be dried (e.g., 80° C., 24 hours) to a dry powder, kept as the prepared dispersion, and/or re-dispersed (e.g., aqueous dispersion).

Representative Preparation of Highly Crystalline Insoluble Alpha-Glucan

Insoluble alpha-1,3-glucan was first prepared by enzymatic synthesis in a manner similar to what is described in U.S. Patent Appl. Publ. Nos. 2018/0340199 and 2019/0078063, which are both incorporated herein by reference. In general, a glucan synthesis reaction was performed comprising water, sucrose, buffer, filtrate from an earlier glucan synthesis reaction (contains, e.g., gluco-oligosaccharide byproducts of the earlier glucan synthesis reaction), and an amino acid-modified, high product-yielding glucosyltransferase enzyme. Following the reaction, the alpha-1,3-glucan product (insoluble, ~100% alpha-1,3 linkages, DPw of about 800) was filtered and washed to remove most fructose and other residual soluble sugars (e.g., glucose, sucrose, leucrose, DP2-DP8 gluco-oligosaccharides). Samples of the washed product were then either collected into wet cakes (never-dried) of about 20-40 wt % solids or dried in a rotary dryer to powders of about 88-95 wt % solids.

Samples of both never-dried and dried insoluble alpha-1,3-glucan were then subjected to hydrochloric acid hydrolysis procedures at a pH of almost 0 at 80° C. to produce reduced molecular weight insoluble alpha-1,3-glucan. Each hydrolysis reaction as initiated contained 8 wt % alpha-1,3-glucan. Procedures disclosed in U.S. Patent Appl. Publ. No. 2013/0244287 (incorporated herein by reference), which describes mineral acid hydrolysis of insoluble alpha-1,3-glucan to soluble alpha-1,3-glucan, can be applied with appropriate modification to hydrolyze alpha-1,3-glucan to a lower molecular weight, but insoluble, form. Hydrolysis reactions were allowed to proceed for 1 hour, 8 hours, 1 day, or 3 days before being neutralized. Each hydrolyzed, insoluble alpha-1,3-glucan product was then analyzed for molecular weight. Insoluble alpha-1,3-glucan with a weight-average degree of polymerization (DPw) of roughly 40-60 was produced after one day of hydrolysis of either never-dried or dried insoluble alpha-1,3-glucan. This molecular weight was stable, remaining at a similar DPw for the duration of hydrolysis under the very low pH conditions. In a separate hydrolysis, insoluble alpha-1,3-glucan with a DPw of about 39 was produced.

Crystallinity (or crystallinity index [CI]) of the alpha-1,3-glucan samples was measured by wide-angle X-ray scattering (WAXS) as follows. Glucan powder samples were dried for a minimum of two hours or overnight (but sometimes over the weekend) in a vacuum oven set at 60° C. Immediately before starting the diffraction scan, each sample was removed from the oven and transferred into a stainless steel holder with a well of about 1.5 cm wide by 4 cm long by 4 mm deep. The well was open at the side such that powder could be poured in through the side, with a glass plate clipped onto the top of the holder. The powder was packed down several times throughout the filling process by hitting the opposite side of the holder against the table repeatedly. Finally, the holder was turned right-side-up, the glass plate was removed, and the holder was loaded into a diffractometer. The time from the opening of the oven to the start of the scan was five minutes or less. An X'PERT MPD POWDER diffractometer (PANalytical B.V., The Netherlands) in reflection mode was used to measure the X-ray diffraction pattern of each powder sample. The X-ray source was a Cu X-ray tube line source with an optical focusing mirror and a 1/16° narrowing slit. X-rays were detected with a 1-D detector and an anti-scatter slit set at 1/8°. Data were collected in the range of 4 to 60 degrees of two-theta at 0.1 degrees per step. The scan took about 46 minutes in total. The resulting X-ray pattern was then analyzed by subtracting a linear baseline from 7.2 to 30.5 degrees, subtracting the XRD pattern of a known amorphous alpha-1,3-glucan sample that had been scaled to fit the current data, and then fitting the remaining crystal peaks in that range with a series of Gaussian curves corresponding to known dehydrated alpha-1,3-glucan crystal reflections. The area corresponding to the crystal peaks was then divided by the total area under the baseline-subtracted curve to yield a crystallinity index.

The crystallinity of the alpha-1,3-glucan samples prepared above by hydrolysis was compared to the crystallinity of enzymatically polymerized alpha-1,3-glucan that was not subjected to hydrolysis. The hydrolyzed alpha-1,3-glucan had substantially greater crystallinity (over 0.65) compared to non-hydrolyzed alpha-1,3-glucan. In particular, hydrolyzed alpha-1,3-glucan with a DPw of 50 (made by acid-hydrolyzing, as above, wet cake for 48 hours at 40° C.) had a crystallinity of about 0.76. A sample of hydrolyzed alpha-1,3-glucan with a DPw of 94 (made by acid-hydrolyzing, as above, wet cake for 1 hour at 40° C.) had a crystallinity of about 0.69. However, samples of non-hydrolyzed alpha-1,3-glucan (~100% alpha-1,3 linkages) produced enzymatically and having DPw values ranging from −230 to ~830 had lower crystallinities (the molecular weight of alpha-1,3-glucan as produced enzymatically can be modulated to be within the range of DPw 230-830 using a technique as described in, for example, U.S. Patent Appl. Publ. No. 2015/0064748, which is incorporated herein by reference).

Using electron microscopy, the microstructure of hydrolyzed alpha-1,3-glucan (DPw 50, 0.76 Cl, 1.2 PDI) was compared to that of non-hydrolyzed alpha-1,3-glucan (DPw ~800) (as produced above). The glucan samples were imaged by dry-cast electron microscopy using phosphotungstate as a contrast agent, as follows. Slurries of DPw 50 and DPw ~800 alpha-1,3-glucan were purified by multiple rounds of centrifugation and redispersion into DI water. The final purified glucan samples were diluted 100-fold and then sonicated for 3 minutes. Once sonication was completed, supernatant from each preparation was isolated to prepare a dry-cast transmission electron microscopy (TEM) sample on a copper mesh TEM grid. Phosphotungstic acid was then used for negative contrast staining, after which TEM imaging was performed. The captured TEM images usually were from sections located at the edge of a larger thick sample deposited on the TEM grid. The hydrolyzed alpha-1,3-glucan (DPw 50) exhibited two-dimensional structures (>about 90 wt % of material that was not aggregated was in the form of plates), whereas the non-hydrolyzed alpha-1,3-glucan (DPw ~800) exhibited larger, three-dimensional fibrillar structures. TEM imaging of non-hydrolyzed alpha-1,3-glucan (~100% alpha-1,3 linkages) produced enzymatically and having a DPw of about 260 showed a microstructure very similar to that of non-hydrolyzed alpha-1,3-glucan (DPw ~800).

Example 1

Producinq Insoluble Alpha-Glucan that has been Surface-Exchanged with Soluble Alpha-Glucan Derivative Compositions were prepared in this Example comprising (i) insoluble alpha-1,3-glucan (DPw ~800, ~100% alpha-1,3 linkages, dispersion particle size $D_{50}$ 1-20 microns), (ii) carboxymethyl alpha-1,3-glucan (CMG) ether (~0.4-0.6 DoS, ~90-130 kDa), water-soluble cationic alpha-1,3-glucan (WSCG) ether (trimethylammonium hydroxypropyl alpha-1,3-glucan (~0.4-0.6 DoS, ~150-160 kDa), or (iii) carboxymethyl cellulose (CMC) ether (Aqualon™ 7LF, ~90 kDa, 0.7 DoS, Ashland Inc.) using a dispersion method (see Materials/Methods). Various amounts of CMG, WSCG, or CMC were added to individual aliquots of an 8 wt % alpha-1,3-glucan (never-dried) dispersion. Dispersions (200 mL) with each component (i and ii) were then blended at high RPM (i.e., high shear) for three minutes using a lab Waring® blender. All the blended samples were analyzed using an Anton Paar rheometer for steady shear viscosity using concentric cylinder geometry. Because all the samples exhibited non-Newtonian behavior, steady shear viscosity at 10 1/s shear rate was selected and represented in the data collected (Table 1).

TABLE 1

| Additive Level Relative to Alpha-1,3-Glucan Weight | Additive CMG | WSCG | CMC |
|---|---|---|---|
| 0 wt % | 329 cps | | |
| 0.1 wt % | 334 cps | 366 cps | 420 cps |
| 1 wt % | 228 cps | 242 cps | 449 cps |
| 4 wt % | 51.6 cps | 86.6 cps | 471 cps |
| 10 wt % | 47.5 cps | 22.6 cps | 446 cps |

Steady shear viscosity (centipoise [cps]) was measured at different loading levels of CMG, WSCG, and CMC additive as shown in the Table 1. The loading levels of CMG, WSCG, and CMC (Table 1) were with respect to the weight of insoluble alpha-1,3-glucan (dry weight basis) in the dispersion to which the CMG, WSCG, or CMC was added.

As shown in Table 1, the steady shear viscosity of the dispersion of alpha-1,3-glucan (8 wt %) in water was 329 cps. The steady shear viscosity results show that, when CMG and WSCG were used as additives, the viscosity was systematically lowered as the additive level is increased. This observation is due to the insoluble alpha-1,3-glucan surface being successfully exchanged with either negative (CMG) or positive (WSCG) surface charge (water is removed from the alpha-1,3-glucan surface); the alpha-1,3-glucan particles are coated with the additive. It is believed that the surface-exchanged (now "charged") alpha-1,3-glucan particles ($D_{50}$ 1-20 micron) now have some repulsion properties, and so particle agglomeration is reduced resulting in a decrease in steady shear viscosity. Strikingly, this decrease in viscosity occurred despite the total solids of the dispersion being increased by the CMG/WSCG additives. These results are in contrast to the observation that water-soluble derivatives of alpha-1,3-glucan (e.g., water-soluble ethers such as CMG and WSCG), when dissolved by themselves in water, typically increase the viscosity of the water (data not shown). Also noteworthy, when CMC was added, the opposite response was observed: the steady shear viscosity was increased by the addition of CMC. This suggests that CMC does not interact with the surface of the insoluble alpha-1,3-glucan particles, but rather is going into (dissolving in) the water phase, thereby increasing viscosity.

Thus, aqueous compositions were prepared having insoluble alpha-1,3-glucan that was surface-exchanged ("surface-modified") with a soluble glucan derivative. This surface-exchanged alpha-1,3-glucan had reduced viscosity, as compared to non-surface-exchanged alpha-1,3-glucan, when dispersed into non-caustic aqueous conditions.

Example 2

Further Production of Insoluble Alpha-Glucan that Has Been Surface-Exchanged with Soluble Alpha-Glucan Derivative This Example shows that surface-exchange using soluble alpha-glucan derivatives can be used to decrease the viscosity of insoluble alpha-1,3-glucan microparticles when dispersed in a non-caustic aqueous medium. These results are further to, and consistent with, the results disclosed in Example 1.

Materials referenced here were the same as disclosed in Example 1. Samples were prepared and analyzed similarly as described in Example 1. Table 2 below shows that the steady shear viscosity of insoluble alpha-1,3-glucan as dispersed in water at 10, 12 or 15 wt % was significantly lowered when WSCG (4 wt %, relative to alpha-1,3-glucan mass) was added.

TABLE 2

| Additive Level Relative to Alpha-1,3-Glucan Weight | Insoluble Alpha-1,3-Glucan Dispersed in Water 15 wt % | 12 wt % | 10 wt % |
|---|---|---|---|
| 0 wt % | 5840 cps | 1320 cps | 610 cps |
| 4 wt % WSCG | 3350 cps | 972 cps | 238 cps |

It was also observed that, while the 15 wt % alpha-1,3-glucan dispersion was not flowable, the addition of WSCG (4 wt % relative to alpha-1,3-glucan mass) caused the dispersion to become flowable.

Example 3

Surface-Exchange to Introduce Surface Charge to Insoluble Alpha-Glucan

This Example compares two different surface-exchange methods—solid state method and dispersion method (see Materials/Methods above)—for modifying the charge characteristics of insoluble alpha-1,3-glucan particles. Surface charge was determined by measuring zeta potential. It was found that surface charge can be imparted by these methodologies, and that surface charge can preserve microparticle structure and prevent drying-induced irreversible agglomeration of particles.

For comparison purposes, chemically derivatized dispersible cationic alpha-1,3-glucan (DCG) (trimethylammonium hydroxypropyl alpha-1,3-glucan, ~130 kDa, ~0.01-0.03 DoS) was used. Insoluble cationic alpha-1,3-glucan ether, which is dispersible and can have a DoS of less than 0.3, can be prepared, for example, by following the disclosure of U.S. Patent Appl. Publ. No. 2016/0311935 (incorporated herein by reference) and adjusting the ratio of alpha-1,3-glucan to cationic etherification agent accordingly.

Surface-exchanged insoluble alpha-1,3-glucan samples prepared in the above Examples by the dispersion method (see Materials/Methods) were used directly for zeta potential analysis, with no further modification.

Surface-exchanged insoluble alpha-1,3-glucan samples prepared using the solid state method (see Materials/Methods) were dried at 80° C. for 3 days to reach a solid content of >90 wt %. The resulting dry powder was dispersed into water, for zeta potential analysis, using the Waring® blender (high RPM, 3 min).

Zeta potential measurement of the samples (using a Malvern ZETASIZER) was used to assess if surface-exchange was successful. Zeta potential was measured with or without tip sonication pretreatment; no significant difference was observed with either measurement approach. The results (Table 3a) indicate that the surface-exchange of insoluble alpha-1,3-glucan with WSCG (same as used in above Examples) provided surface charge. This surface charge was generally constant, regardless of how the surface exchange was conducted (solid state or dispersion state).

TABLE 3a

| Composition Dispersed in Water | with sonication Zeta Potential (mV) | with sonication Error (mV) | without sonication Zeta Potential (mV) | without sonication Error (mV) |
|---|---|---|---|---|
| Ins. Alpha-1,3-Glucan | −1.56 | 7.43 | −0.663 | 7.75 |
| DCG | +26.6 | 4.86 | +26.2 | 6.35 |
| Ins. Alpha-1,3-Glucan + 15 wt %[a] WSCG via Solid State Method | +40.1 | 7.51 | +38.9 | 9.26 |
| Ins. Alpha-1,3-Glucan + 15 wt %[a] WSCG via Solid State Method (dried, resuspended) | +38.2 | 5.42 | +39.9 | 6.08 |
| Ins. Alpha-1,3-Glucan + 15 wt %[a] WSCG via Dispersion Method | +40.9 | 10.8 | +36.1 | 9.02 |
| Ins. Alpha-1,3-Glucan + 4 wt %[a] WSCG via Dispersion Method | +40.4 | 10.9 | +37.5 | 9.47 |

[a]WSCG wt % relative to the mass of the insoluble alpha-1,3-glucan in the composition.

Additional data were collected to determine if the presence of WSCG on the surface of insoluble alpha-1,3-glucan prevents the irreversible agglomeration of alpha-1,3-glucan particles that occurs with drying. Particle size was measured using a laser light diffraction particle size analyzer (Table 3b).

TABLE 3b

| row | Composition Dispersed in Water[a] | $D_{50}$ (μm) | $D_{90}$ (μm) |
|---|---|---|---|
| 1 | Ins. Alpha-1,3-Glucan (never-dried) | 10.66 | 17.31 |
| 2 | Ins. Alpha-1,3-Glucan (dried, resuspended)[c] | 8.82 | 101.5 |
| 3 | DCG | 18.66 | 129 |
| 4 | Ins. Alpha-1,3-Glucan + 15 wt %[b] WSCG via Dispersion Method | 9.98 | 21.04 |
| 5 | Ins. Alpha-1,3-Glucan + 15 wt %[b] WSCG via Dispersion Method (dried, resuspended)[c] | 9.67 | 21.47 |

[a]Each composition was dispersed at about 8 wt %.
[b]WSCG wt % relative to the mass of the insoluble alpha-1,3-glucan in the composition.
[c]Dried in a vacuum oven (80° C., 24 hr) and redispersed using a Waring ® blender (max RPM, 3 min).

The results in Table 3b indicate that the surface-exchange of insoluble alpha-1,3-glucan with WSCG preserved microparticle structure and prevented the irreversible agglomeration that is typically observed when insoluble alpha-1,3-glucan is dried. While non-surface-exchanged, dried and resuspended alpha-1,3-glucan (row 2) exhibited particles of larger size ($D_{90}$) as compared to non-surface-exchanged, never-dried dispersed alpha-1,3-glucan (row 1), both surface-exchanged alpha-1,3-glucan (row 4) (which was never-dried) and surface-exchanged, dried and resuspended alpha-1,3-glucan (row 5) exhibited almost the same particle size profile in dispersion. Interestingly, particles of insoluble alpha-1,3-glucan chemically derivatized with cationic groups (DCG, row 3) exhibited a particle size profile (e.g., much elevated $D_{90}$) in dispersion similar to the non-surface-exchanged, dried and resuspended alpha-1,3-glucan (row 2).

It is contemplated that, in view of the above observations, surface-exchanging insoluble alpha-1,3-glucan with negatively charged alpha-1,3-glucan derivative such as CMG (e.g., see above Examples) similarly preserves microparticle structure and prevents drying-induced irreversible agglomeration.

Example 4

Surface-Exchange to Introduce Surface Charge to Insoluble Microcrystalline Alpha-Glucan This Example describes surface-exchanging insoluble microcrystalline alpha-1,3-glucan (MCG) (DPw 40-50, ~100% alpha-1,3 linkages, 0.76 Cl [crystallinity index]) to provide surface charge to MCG. This surface charge increased the rheological properties of MCG: surface-exchanged MCG as dispersed in water brought about higher viscosity as compared to MCG that was not surface-exchanged.

MCG was prepared and analyzed following methodology similar to what is described above in the Materials/Methods. MCG was dried to >90 wt % solids in an oven at 80° C. for 3 days. The MCG dry powder was rehydrated in water and hand-mixed using a paddle to produce an MCG wet cake at 40 wt % solids. Particles of this MCG as dispersed in water had a particle size $D_{50}$ of about 200-500 microns; this size, which is larger than the typical sub-micron size of MCG, is believed to be due to particle aggregation.

The solid state method (Materials/Methods) was then used to prepare surface-exchanged MCG samples using CMC and WSCG (Example 1). CMC or WSCG dry powder (15 wt % each relative to the mass of CMG) was added to the MCG wet cake and mixed using a paddle mixer. Each sample preparation (MCG alone, MCG+CMC, MCG+WSCG) was then processed three consecutive times through an extrusion device. The extruded mixes were then individually dispersed in water at 10 wt % (dry weight basis) using a lab waring blender (high RPM, 3 min). Each dispersion was then analyzed for viscosity using an Anton Paar rheometer.

The results shown in Table 4 indicate that, when CMC was used to attempt surface-exchange of MCG, such treated MCG increased viscosity when dispersed in water. Similar to what was observed when attempting to surface-exchange insoluble alpha-1,3-glucan in Example 1, it is believed that the CMC did not maintain any interaction with the MCG, but rather occupied (dissolved in) the water phase thereby increasing viscosity.

MCG that was surface-exchanged with WSCG to have a positive surface charge brought about a significant increase in viscosity (1600 cps), which was about two orders of magnitude higher than the viscosity of dispersed, unmodified MCG (25.6 cps) (Table 4). This result was in contrast to what was observed in Examples 1 and 2 in which surface-exchange of ~DPw 800 insoluble alpha-1,3-glucan resulted in glucan particles that had reduced viscosity in water.

TABLE 4

| Composition | Viscosity of Aqueous Dispersion |
|---|---|
| MCG | 25.6 cps |
| MCG + 15 wt %[a] CMC | 1340 cps |
| MCG + 15 wt %[a] WSCG | 1600 cps |

[a]WSCG or CMC wt % relative to the mass of the MCG in the composition.

Example 5

Phase Exchange of Insoluble Alpha-Glucan

This Example shows that, using the solid state surface modification method (Materials/Methods, but with different phase modifiers), the phase of insoluble alpha-1,3-glucan can be modified. Following this process allows preservation of alpha-1,3-glucan particle structure.

Alpha-1,3-glucan wet cake with no additives can be 40 wt % solids (i.e., 40 wt % alpha-1,3-glucan), where the remaining 60 wt % is water. When the water is removed from the wet cake by drying, the alpha-1,3-glucan irreversibly forms agglomerates through hydrogen bonding, which collapses the microstructure of the original alpha-1,3-glucan particles. The surface-exchange work shown in Example 3 suggests that modifying the surface of insoluble alpha-1,3-glucan with charge prevents this hydrogen bond-induced irreversible agglomeration.

A similar approach was taken in this Example where, instead of surface-exchange with a soluble, charged alpha-1,3-glucan, the entire water phase was replaced with a different phase. Insoluble alpha-1,3-glucan as used in Example 1 was used in this Example (DPw ~800, ~100% alpha-1,3 linkages, dispersion particle size $D_{50}$ 1-20 microns).

Four different materials were tested for replacing water as a phase for insoluble alpha-1,3-glucan: pine resin (slash pine tree resin, Diamond G Forest Products, S. Georgia), refined linseed oil (US Art Suppliers), epoxidized linseed oil (EPLO, available as NatureFlex™ ELO, The Chemical Company), and glycerol (Sigma-Aldrich) for phase modification. For convenience, these materials are referred to herein as "phase modifiers" (examples of "additives" herein). The four different phase modifiers were individually added to alpha-1,3-glucan wet cake (40 wt % solids) at the same mass level of the water in the wet cake (i.e., 60 wt % of the wet cake), and then processed through an extrusion device as done in Example 4.

Each product collected after performing this solid state phase-exchange process was calculated to contain: 25 wt % insoluble alpha-1,3-glucan, 37.5 wt % water, and 37.5 wt % phase modifier. This state of wet cake was referred to as "intermediate phase-modified wet cake" for convenience. The texture and appearance of each intermediate phase-modified wet cake was influenced by its respective phase modifier. The intermediate phase-modified wet cakes were then dried at 85° C. for two days to remove water to produce completely phase-modified insoluble alpha-1,3-glucan. The texture and appearance of each phase-modified composition was influenced by its constituent phase modifier. For example, if a solid phase modifier was used such as pine resin, the resulting phase-modified composition had a solid texture. When an oil phase modifier was used such as linseed oil, the resulting phase-modified composition was oily in texture. Table 5 summarizes the visual and textural observations of the phase-modified alpha-1,3-glucan compositions.

TABLE 5

| | Phase | | | |
|---|---|---|---|---|
| | Pine Resin | Linseed Oil | EPLO | Glycerol |
| Phase state before being used to phase-modify alpha-1,3-glucan | Solid powder | Liquid | Liquid | Liquid |
| Characteristics of intermediate phase-modified alpha-1,3-glucan wet cake | Loosely agglomerated dry powder | Oily wet cake powder | Slightly oily, loosely agglomerated wet cake powder | Sticky wet cake powder |
| Characteristics of alpha-1,3-glucan composition after phase modification | Hard but moldable | Oily, soft wet cake powder | Slightly oily, hard powder | Soft wet cake powder |

The glycerol phase-modified alpha-1,3-glucan composition was analyzed for particle size to determine whether the irreversible agglomeration of insoluble alpha-1,3-glucan typically induced by water removal was prevented by the staged phase modification. Particle size was measured using a laser light diffraction particle size analyzer. The results (Table 6) show that the particle sizes associated with both intermediate phase-modified alpha-1,3-glucan wet cake and completely phase-modified alpha-1,3-glucan were generally unaltered as compared to the particle size associated with alpha-1,3-glucan wet cake prior to phase modification (control) processing.

TABLE 6

| Composition | Mean (μm) | $D_{10}$ (μm) | $D_{50}$ (μm) | $D_{90}$ (μm) |
|---|---|---|---|---|
| Alpha-1,3-glucan wet cake (control) | 8.150 | 3.930 | 7.400 | 13.34 |
| Glycerol intermediate phase-modified alpha-1,3-glucan wet cake | 8.410 | 4.440 | 8.570 | 12.66 |
| Glycerol phase-modified alpha-1,3-glucan | 8.800 | 4.150 | 8.080 | 14.84 |

Similar results of preserving particle size were observed with the other tested phases (data not shown). Thus, phase-modification of insoluble alpha-1,3-glucan can be used to prevent the irreversible agglomeration that is typically observed when insoluble (non-phase-modified) alpha-1,3-glucan is dried.

Example 6

Color Control of Insoluble Alpha-Glucan

To alter the color of insoluble alpha-glucan herein, an additive with bleaching activity (e.g., hydrogen peroxide or chlorine bleach) can be added to chemically deactivate the chromophores present in some preparations of insoluble alpha-glucan. This Example, in particular, shows that treatment of different grades of MCG with hydrogen peroxide can lighten the color of the material.

Samples of MCG were generally prepared as in Example 4 above and dispersed at 8-10 wt % in water (final dispersions of 1 L). One MCG sample (MCG-TG) as dispersed was expected to comprise 14-16 wt % water-soluble sugar impurities (e.g., glucose, fructose, gluco-oligosaccharides). Another MCG sample (MCG-SG) as dispersed was expected to have <0.4 wt % of such impurities. To each of the MCG-TG and MCG-SG dispersions, 1 mL of 30 wt % hydrogen peroxide solution (Sigma Aldrich) was added; another set of these dispersions did not receive hydrogen peroxide. The dispersions were then dried in a vacuum oven (130° C.) for 3 days to completely remove the water. The color of each dried product was then measured using image analysis (ImageJ, LOCI website, University of Wisconsin-Madison). The results (L, a, b) of this analysis are shown in Table 7 below.

TABLE 7

| Sample | Hydrogen Peroxide Treatment | |
|---|---|---|
| | No | Yes |
| MCG-TG | L: 63.87, a: −1.68, b: 15.21 | L: 68.38, a: −3.45, b: 13.63 |
| MCG-SG | L: 57.23, a: −0.14, b: 14.47 | L: 67.70, a: −0.73, b: 11.73 |

The three coordinates of the L a b color space in this Example represent, respectively, lightness of the color of a solid (L=0 indicates black and L=100 indicates diffuse white), the color of the object along a scale between red/magenta and green (a, negative values indicate green while positive values indicate magenta), and the color of the object along a scale between yellow and blue (b, negative values indicate blue and positive values indicate yellow).

Example 7

Insoluble Alpha-Glucan as a Rheology Modifier

This Example shows that insoluble alpha-1,3-glucan can be used as an agent for gelling, viscosifying, and/or solidifying otherwise liquid or non-solid chemical compounds. In particular, insoluble alpha-1,3-glucan was used as a gelling agent for each of glycerol, 1,3-propanediol, and petrolatum jelly.

MCG (Example 4, provided as 10 wt % dispersion in water) was blended with glycerol, propanediol, or petrolatum jelly at room temperature, followed by removal of all water by distillation or rotary evaporation. The final products had 10 or 15 wt % MCG. While glycerol with 10 wt % MCG was flowable, glycerol with 15 wt % MCG was not flowable (had the appearance and haptics of an ointment); similar results were observed with the propanediol-based products.

Table 8 shows the results of sensory assessments of petrolatum jelly (no MCG) and glycerol with 15 wt % MCG (sensory ratings: 1-low; 5-high). The glycerol-based sample had lower values for greasiness and gloss as compared to these features for petrolatum jelly, indicating better after-feel results. Another benefit of using glycerol with MCG is the possibility to further formulate the glycerol with polar and/or water-soluble additives; such additives would not be useful in petrolatum jelly due to solubility issues. Glycerol with 15 wt % MCG also had some appearance and rub-out features comparable to petrolatum jelly (Table 8). Similar sensory assessments were obtained with propanediol having 15 wt % MCG, while petrolatum jelly with 15 wt % MCG had improved touch, feel and haptics (data not shown).

TABLE 8

| Sensory Assessment | | Glycerol w/ 15 wt % MCG | Petrolatum Jelly |
|---|---|---|---|
| Gloss - Appearance | * | 4 | 4 |
| Firmness - Appearance | ** | 5 | 5 |
| Stringiness - Pick-up | lower is better | 3 | 2 |
| Stickiness - Pick-up | lower is better | 3 | 1 |
| Spreadability - Rub-out | higher is better | 2 | 2 |
| Sliminess - Rub-out | lower is better | 1 | 1 |
| Absorbency - Rub-out | higher is better | 3 | 1 |
| Gloss - After-feel | * | 3 | 5 |
| Stickiness - After-feel | lower is better | 2 | 1 |
| Greasiness - After-feel | lower is better | 2 | 5 |

* Some consumers consider higher to be better in applications such as lip care, where others prefer lower to be better such as for skin (non-lips) application.
** Consumers consider higher to be better for products intended to be firm/non-flowable.

Consumers will likely be accepting of, and appreciate the benefits of, personal care products (e.g., lotions/ointments, such as for skin treatment) containing insoluble alpha-1,3-glucan, which is a sustainable ingredient. Alpha-1,3-glucan can endow features to glycerol and similar sustainable materials (e.g., propanediol) to make products that are better than, or equal to, an otherwise non-sustainable (petroleum-derived) incumbent material (petrolatum jelly).

What is claimed is:

1. A composition comprising insoluble alpha-glucan and a soluble alpha-glucan derivative, wherein at least about 50% of the glycosidic linkages of the insoluble alpha-glucan are alpha-1,3 glycosidic linkages, and the weight-average degree of polymerization (DPw) of the insoluble alpha-glucan is at least 15, wherein at least about 50% of the glycosidic linkages of the soluble alpha-glucan derivative are alpha-1,3 glycosidic linkages, and the DPw of the alpha-glucan portion of the soluble alpha-glucan derivative is at least 15.

2. The composition of claim 1, wherein at least about 90% of the glycosidic linkages of the insoluble alpha-glucan are alpha-1,3 glycosidic linkages, and/or wherein at least about 90% of the glycosidic linkages of the soluble alpha-glucan derivative are alpha-1,3 glycosidic linkages.

3. The composition of claim 1, wherein the insoluble alpha-glucan:

(i) has a DPw over 100, (ii) is in the form of fibrids, or (iii) has a DPw of about 15 to 100 and/or is in the form of particles having a degree of crystallinity of at least about 0.65.

4. The composition of claim 1, wherein the soluble alpha-glucan derivative has a degree of substitution (DOS) up to about 3.0 with at least one organic group that has a positive charge or a negative charge.

5. The composition of claim 4, wherein the DoS with the organic group is at least about 0.3.

6. The composition of claim 4, wherein the organic group is ether-linked to the soluble alpha-glucan derivative.

7. The composition of claim 1, wherein the insoluble alpha-glucan is coated by the soluble alpha-glucan derivative.

8. The composition of claim 7, wherein the particles have a positive surface charge.

9. The composition of claim 7, wherein the composition comprises particles of the insoluble alpha-glucan coated by the soluble alpha-glucan derivative.

10. The composition of claim 9, wherein the particles have a negative surface charge.

11. The composition of claim 1, wherein the composition further comprises an additive that does not chemically react with the insoluble alpha-glucan or the soluble alpha-glucan derivative.

12. The composition of claim 1, wherein the composition is in the form of a dispersion, or wet cake or wet powder.

13. The composition of claim 1, comprising about 0.1 to about 50 wt % of the soluble alpha-glucan derivative, wherein said wt % is based on the weight of the insoluble alpha-glucan in the composition.

14. The composition of claim 1, wherein the soluble alpha-glucan derivative has a degree of substitution (DoS) up to about 3.0 with at least one organic group that has a negative charge.

15. The composition of claim 14, wherein the DoS with the organic group is at least about 0.3.

16. The composition of claim 1, comprising about 1 to about 30 wt % of the soluble alpha-glucan derivative, wherein said wt % is based on the weight of the insoluble alpha-glucan in the composition.

17. The composition of claim 1, wherein the composition is in the form of a dry powder.

18. The composition of claim 1, wherein the composition is in the form of an extrusion, composite, film, coating, or encapsulant.

19. A method of producing a composition according to claim 1, said method comprising:

(a) blending together at least water, said insoluble alpha-glucan, and said soluble alpha-glucan derivative to provide a blended product, and (b) optionally drying the blended product.

20. The method of claim 19, wherein:

step (a) is performed by blending (i) a dry powder of said soluble alpha-glucan derivative and (ii) a composition comprising about 10 to 80 wt % of said insoluble alpha-glucan and a balance of water or aqueous solution up to 100 wt %; or step (a) is performed by blending (i) a dry powder of said soluble alpha-glucan derivative, (ii) a composition comprising about 10 to 80 wt % of said insoluble alpha-glucan and a balance of water or aqueous solution up to 100 wt %, and (iii) water or aqueous solution, wherein the total solids of the blended product is about 1 to 30 wt %.

* * * * *